US010349824B2

(12) United States Patent
Claude et al.

(10) Patent No.: US 10,349,824 B2
(45) Date of Patent: Jul. 16, 2019

(54) TISSUE MAPPING AND VISUALIZATION SYSTEMS

(71) Applicant: Apama Medical, Inc., Campbell, CA (US)

(72) Inventors: John P. Claude, Redwood City, CA (US); Jonah Lepak, Santa Cruz, CA (US); Adnan Merchant, Fremont, CA (US); Amr Salahieh, Saratoga, CA (US); Tom Saul, Moss Beach, CA (US)

(73) Assignee: Apama Medical, Inc., Campbell, CA (US)

( * ) Notice: Subject to any disclaimer, the term of this patent is extended or adjusted under 35 U.S.C. 154(b) by 260 days.

(21) Appl. No.: 15/194,444

(22) Filed: Jun. 27, 2016

(65) Prior Publication Data

US 2017/0143201 A1    May 25, 2017

Related U.S. Application Data

(63) Continuation-in-part of application No. 14/248,288, filed on Apr. 8, 2014, now Pat. No. 9,717,557.
(Continued)

(51) Int. Cl.
*A61B 18/14* (2006.01)
*A61B 1/313* (2006.01)
(Continued)

(52) U.S. Cl.
CPC ........ *A61B 1/3137* (2013.01); *A61B 1/00045* (2013.01); *A61B 1/00082* (2013.01);
(Continued)

(58) Field of Classification Search
CPC ............ A61B 18/1492; A61B 18/1206; A61B 18/1815; A61B 2018/00285;
(Continued)

(56) References Cited

U.S. PATENT DOCUMENTS 4,448,188 A    5/1984  Loeb
4,547,193 A   10/1985  Rydell
(Continued)

FOREIGN PATENT DOCUMENTS

CN    1085416 A    4/1994
CN    1781161 A    5/2006
(Continued)

OTHER PUBLICATIONS

Extended European Search Report issued in EP App;lication 15811644. 2, dated Dec. 12, 2017, 8 pages.
(Continued)

*Primary Examiner* — Thomas A Giuliani

(57) ABSTRACT

Visualization and ablation systems and catheters. The systems can capture a plurality of different 2D images of the patient's anatomy adjacent an expandable member, each of which visualizes at least one part of the patient that is in contact with the expandable membrane, tag each of the plurality of different 2D images with information indicative of the position and orientation of a locational element when each of the plurality of different 2D images was captured, create a patient map, wherein creating the patient map comprises placing each of the plurality of different 2D images at the corresponding tagged position and orientation into a 3 space, and display the patient map.

20 Claims, 30 Drawing Sheets

Related U.S. Application Data

(60) Provisional application No. 62/185,356, filed on Jun. 26, 2015, provisional application No. 61/947,950, filed on Mar. 4, 2014, provisional application No. 61/945,005, filed on Feb. 26, 2014, provisional application No. 61/939,185, filed on Feb. 12, 2014, provisional application No. 61/934,640, filed on Jan. 31, 2014, provisional application No. 61/934,647, filed on Jan. 31, 2014, provisional application No. 61/895,880, filed on Oct. 25, 2013, provisional application No. 61/864,335, filed on Aug. 9, 2013, provisional application No. 61/829,985, filed on May 31, 2013, provisional application No. 61/821,014, filed on May 8, 2013, provisional application No. 61/821,001, filed on May 8, 2013, provisional application No. 61/820,992, filed on May 8, 2013, provisional application No. 61/809,629, filed on Apr. 8, 2013, provisional application No. 61/809,646, filed on Apr. 8, 2013, provisional application No. 61/809,636, filed on Apr. 8, 2013.

(51) Int. Cl.

| | | |
|---|---|---|
| *A61B 1/00* | (2006.01) | |
| *A61B 1/05* | (2006.01) | |
| *A61B 5/00* | (2006.01) | |
| *A61B 1/06* | (2006.01) | |
| *A61B 5/01* | (2006.01) | |
| *A61B 5/053* | (2006.01) | |
| *A61M 25/10* | (2013.01) | |
| *A61B 90/00* | (2016.01) | |
| *A61B 18/00* | (2006.01) | |
| *A61N 1/05* | (2006.01) | |
| *A61B 18/12* | (2006.01) | |
| *A61B 18/18* | (2006.01) | |
| *A61M 25/01* | (2006.01) | |
| *A61M 25/04* | (2006.01) | |
| *A61B 17/00* | (2006.01) | |
| *A61B 17/22* | (2006.01) | |
| *A61M 25/06* | (2006.01) | |
| *A61B 90/30* | (2016.01) | |
| *A61B 34/10* | (2016.01) | |
| *A61B 34/20* | (2016.01) | |

(52) U.S. Cl.
CPC ...... *A61B 1/00087* (2013.01); *A61B 1/00096* (2013.01); *A61B 1/05* (2013.01); *A61B 1/051* (2013.01); *A61B 1/0676* (2013.01); *A61B 1/313* (2013.01); *A61B 5/01* (2013.01); *A61B 5/0538* (2013.01); *A61B 5/6858* (2013.01); *A61B 18/1492* (2013.01); *A61B 90/361* (2016.02); *A61M 25/10* (2013.01); *A61M 25/1011* (2013.01); *A61B 5/6853* (2013.01); *A61B 5/6855* (2013.01); *A61B 18/1206* (2013.01); *A61B 18/1815* (2013.01); *A61B 90/30* (2016.02); *A61B 90/37* (2016.02); *A61B 2017/00831* (2013.01); *A61B 2017/22038* (2013.01); *A61B 2018/00011* (2013.01); *A61B 2018/0016* (2013.01); *A61B 2018/0022* (2013.01); *A61B 2018/00023* (2013.01); *A61B 2018/00029* (2013.01); *A61B 2018/00083* (2013.01); *A61B 2018/00214* (2013.01); *A61B 2018/00232* (2013.01); *A61B 2018/00238* (2013.01); *A61B 2018/00267* (2013.01); *A61B 2018/00285* (2013.01); *A61B 2018/00291* (2013.01); *A61B 2018/00351* (2013.01); *A61B 2018/00357* (2013.01); *A61B 2018/00375* (2013.01); *A61B 2018/00577* (2013.01); *A61B 2018/00642* (2013.01); *A61B 2018/00702* (2013.01); *A61B 2018/00744* (2013.01); *A61B 2018/00791* (2013.01); *A61B 2018/00797* (2013.01); *A61B 2018/00815* (2013.01); *A61B 2018/00839* (2013.01); *A61B 2018/00875* (2013.01); *A61B 2018/00898* (2013.01); *A61B 2018/00982* (2013.01); *A61B 2018/124* (2013.01); *A61B 2018/1435* (2013.01); *A61B 2018/1465* (2013.01); *A61B 2034/107* (2016.02); *A61B 2034/2048* (2016.02); *A61B 2034/2051* (2016.02); *A61B 2034/2055* (2016.02); *A61B 2034/2057* (2016.02); *A61B 2034/2065* (2016.02); *A61B 2090/0454* (2016.02); *A61B 2090/064* (2016.02); *A61B 2090/065* (2016.02); *A61B 2090/309* (2016.02); *A61B 2090/364* (2016.02); *A61B 2090/367* (2016.02); *A61B 2090/3614* (2016.02); *A61B 2090/371* (2016.02); *A61B 2090/373* (2016.02); *A61B 2090/395* (2016.02); *A61B 2090/3966* (2016.02); *A61B 2217/007* (2013.01); *A61B 2218/002* (2013.01); *A61B 2562/125* (2013.01); *A61B 2562/164* (2013.01); *A61M 25/0108* (2013.01); *A61M 25/0133* (2013.01); *A61M 25/0147* (2013.01); *A61M 25/04* (2013.01); *A61M 2025/0681* (2013.01); *A61N 1/05* (2013.01); *C08L 2201/12* (2013.01)

(58) Field of Classification Search
CPC A61B 2018/00291; A61B 2018/00351; A61B 2018/00375; A61B 2018/00244; A61B 2018/00011; A61B 2018/00023; A61B 2018/00029; A61B 2018/00083; A61B 2018/0016; A61B 2018/00214; A61B 2018/0022; A61B 2018/00232; A61B 2018/00238; A61B 2018/00267; A61B 2018/00273; A61B 2018/00279; A61B 2018/1435; A61B 2018/1465; A61B 2018/00797; A61B 2018/00642; A61B 2018/00815; A61B 2018/00744; A61B 2018/00839; A61B 2018/00702; A61B 2018/00875; A61B 2018/00791; A61B 2018/00898; A61B 2018/124; A61B 2018/00357; A61B 2018/00577; A61B 2018/00982; A61B 2034/107; A61B 2034/2048; A61B 2034/2051; A61B 2034/2055; A61B 2034/2057; A61B 2034/2065; A61B 90/361; A61B 90/30; A61B 90/37; A61B 2217/007; A61B 2218/002; A61B 1/00082; A61B 1/00087; A61B 1/00096; A61B 1/043; A61B 1/3137; A61B 1/051; A61B 1/00045; A61B 1/00041; A61B 1/05; A61B 1/0676; A61B 1/313; A61B 5/1032; A61B 5/6858; A61B 5/01; A61B 5/0538; A61B 5/6853; A61B 5/6855; A61B 2562/125; A61B 2562/164; A61B 2017/00831; A61B 2017/22038; A61B 2090/3614; A61B 2090/064; A61B 2090/309; A61B 2090/364; A61B 2090/0454; A61B 2090/065; A61B 2090/371; A61B 2090/373; A61B 2090/367; A61B 2090/395; A61M 25/10; A61M 25/1011;

A61M 25/0108; A61M 25/0133; A61M 25/04; A61M 25/0147; A61M 2025/0681; A61N 1/05; C08L 2201/12
USPC .................................... 606/34, 38, 41, 42
See application file for complete search history.

(56) References Cited

U.S. PATENT DOCUMENTS

| | | | |
|---|---|---|---|
| 4,602,281 A | 7/1986 | Nagasaki et al. |
| 4,611,888 A | 9/1986 | Prenovitz et al. |
| 4,633,879 A | 1/1987 | Ong |
| 4,634,432 A | 1/1987 | Kocak |
| 4,638,207 A | 1/1987 | Radice |
| 4,646,721 A | 3/1987 | Arakawa |
| 4,692,139 A | 9/1987 | Stiles |
| 4,726,382 A | 2/1988 | Boehmer et al. |
| 4,739,766 A | 4/1988 | Riederer |
| 4,784,133 A | 11/1988 | Mackin |
| 4,809,680 A | 3/1989 | Yabe |
| 4,827,907 A | 5/1989 | Tashiro |
| 4,832,003 A | 5/1989 | Yabe |
| 4,843,275 A | 6/1989 | Radice |
| 4,890,623 A | 1/1990 | Cook et al. |
| 4,961,738 A | 10/1990 | Mackin |
| 4,968,306 A | 11/1990 | Huss et al. |
| 5,010,895 A | 4/1991 | Maurer et al. |
| 5,029,574 A | 7/1991 | Shimamura et al. |
| 5,041,089 A | 8/1991 | Mueller et al. |
| 5,069,674 A | 12/1991 | Fearnot et al. |
| 5,090,959 A | 2/1992 | Samson et al. |
| 5,109,861 A | 5/1992 | Walinsky et al. |
| 5,115,472 A | 5/1992 | Park et al. |
| 5,135,001 A | 8/1992 | Sinofsky et al. |
| 5,180,376 A | 1/1993 | Fischell |
| 5,187,572 A | 2/1993 | Nakamura et al. |
| 5,209,741 A | 5/1993 | Spaeth |
| 5,213,576 A | 5/1993 | Abiuso et al. |
| 5,228,442 A | 7/1993 | Imran |
| 5,233,416 A | 8/1993 | Inoue |
| 5,301,090 A | 4/1994 | Hed |
| 5,306,250 A | 4/1994 | March et al. |
| 5,309,910 A | 5/1994 | Edwards et al. |
| 5,311,866 A | 5/1994 | Kagan et al. |
| 5,325,847 A | 7/1994 | Matsuno |
| 5,343,860 A | 9/1994 | Metzger et al. |
| 5,377,682 A | 1/1995 | Ueno et al. |
| 5,385,148 A | 1/1995 | Lesh et al. |
| 5,391,200 A | 2/1995 | KenKnight et al. |
| 5,409,000 A | 4/1995 | Imran |
| 5,411,016 A | 5/1995 | Kume et al. |
| 5,430,475 A | 7/1995 | Goto et al. |
| 5,443,470 A | 8/1995 | Stern et al. |
| 5,494,483 A | 2/1996 | Adair |
| 5,505,730 A | 4/1996 | Edwards |
| 5,515,843 A | 5/1996 | Chang |
| 5,515,848 A | 5/1996 | Corbett, III et al. |
| 5,524,338 A | 6/1996 | Martyniuk et al. |
| 5,540,679 A | 7/1996 | Fram et al. |
| 5,558,672 A | 9/1996 | Edwards et al. |
| 5,562,720 A | 10/1996 | Stern et al. |
| 5,569,241 A | 10/1996 | Edwards |
| 5,571,086 A | 11/1996 | Kaplan et al. |
| 5,571,088 A | 11/1996 | Lennox et al. |
| 5,573,520 A | 11/1996 | Schwartz et al. |
| 5,575,772 A | 11/1996 | Lennox |
| 5,575,788 A | 11/1996 | Baker et al. |
| 5,594,497 A | 1/1997 | Ahern et al. |
| 5,607,436 A | 3/1997 | Pratt et al. |
| 5,609,574 A | 3/1997 | Kaplan et al. |
| 5,609,606 A | 3/1997 | O'Boyle |
| 5,611,807 A | 3/1997 | O'Boyle |
| 5,626,564 A | 5/1997 | Zhan et al. |
| 5,630,837 A | 5/1997 | Crowley |
| 5,681,308 A | 10/1997 | Edwards et al. |
| 5,715,825 A | 2/1998 | Crowley |
| 5,718,701 A | 2/1998 | Shai et al. |
| 5,722,403 A | 3/1998 | McGee et al. |
| 5,735,846 A | 4/1998 | Panescu et al. |
| 5,769,846 A | 6/1998 | Edwards et al. |
| 5,769,880 A | 6/1998 | Truckai et al. |
| 5,779,698 A | 7/1998 | Clayman et al. |
| 5,795,325 A | 8/1998 | Valley et al. |
| 5,797,837 A | 8/1998 | Minami |
| 5,800,408 A | 9/1998 | Strauss et al. |
| 5,827,273 A | 10/1998 | Edwards |
| 5,830,213 A | 11/1998 | Panescu et al. |
| 5,836,874 A | 11/1998 | Swanson et al. |
| 5,846,196 A | 12/1998 | Siekmeyer et al. |
| 5,846,238 A | 12/1998 | Jackson et al. |
| 5,846,239 A | 12/1998 | Swanson et al. |
| 5,853,411 A | 12/1998 | Whayne et al. |
| 5,860,974 A | 1/1999 | Abele |
| 5,871,483 A | 2/1999 | Jackson et al. |
| 5,879,348 A | 3/1999 | Owens et al. |
| 5,881,727 A | 3/1999 | Edwards |
| 5,888,577 A | 3/1999 | Griffin, III et al. |
| 5,904,651 A | 5/1999 | Swanson et al. |
| 5,916,213 A | 6/1999 | Haissaguerre et al. |
| 5,935,075 A | 8/1999 | Casscells et al. |
| 5,938,660 A | 8/1999 | Swartz et al. |
| 5,940,126 A | 8/1999 | Kimura |
| 5,957,950 A | 9/1999 | Mockros et al. |
| 5,961,513 A | 10/1999 | Swanson et al. |
| 5,967,986 A | 10/1999 | Cimochowski et al. |
| 5,984,860 A | 11/1999 | Shan |
| 5,991,650 A | 11/1999 | Swanson et al. |
| 5,997,571 A | 12/1999 | Farr et al. |
| 6,004,269 A | 12/1999 | Crowley et al. |
| 6,006,119 A | 12/1999 | Soller et al. |
| 6,012,457 A | 1/2000 | Lesh |
| 6,024,740 A | 2/2000 | Lesh et al. |
| 6,052,607 A | 4/2000 | Edwards et al. |
| 6,071,302 A | 6/2000 | Sinofsky et al. |
| 6,102,905 A | 8/2000 | Baxter et al. |
| 6,117,101 A | 9/2000 | Diederich et al. |
| 6,123,718 A | 9/2000 | Tu et al. |
| 6,124,883 A | 9/2000 | Suzuki et al. |
| 6,134,463 A | 10/2000 | Wittkampf et al. |
| 6,142,993 A | 11/2000 | Whayne et al. |
| 6,159,203 A | 12/2000 | Sinofsky |
| 6,163,726 A | 12/2000 | Wolf |
| 6,164,283 A | 12/2000 | Lesh |
| 6,168,591 B1 | 1/2001 | Sinofsky |
| 6,178,346 B1 | 1/2001 | Amundson et al. |
| 6,205,361 B1 | 3/2001 | Kuzma et al. |
| 6,206,912 B1 | 3/2001 | Goldsteen et al. |
| 6,215,231 B1 | 4/2001 | Newnham et al. |
| 6,231,516 B1 | 5/2001 | Keilman et al. |
| 6,233,491 B1 | 5/2001 | Kordis et al. |
| 6,258,087 B1 | 7/2001 | Edwards et al. |
| 6,270,492 B1 | 8/2001 | Sinofsky |
| 6,292,689 B1 | 9/2001 | Wallace et al. |
| 6,315,712 B1 | 11/2001 | Rovegno |
| 6,375,654 B1 | 4/2002 | McIntyre |
| 6,384,915 B1 | 5/2002 | Everett et al. |
| 6,391,024 B1 | 5/2002 | Sun et al. |
| 6,402,746 B1 | 6/2002 | Whayne et al. |
| 6,416,463 B1 | 7/2002 | Tsuzuki et al. |
| 6,425,877 B1 | 7/2002 | Edwards |
| 6,460,545 B2 | 10/2002 | Kordis |
| 6,485,414 B1 | 11/2002 | Neuberger |
| 6,500,174 B1 | 12/2002 | Maguire et al. |
| 6,511,478 B1 | 1/2003 | Burnside et al. |
| 6,514,249 B1 | 2/2003 | Maguire et al. |
| 6,517,534 B1 | 2/2003 | McGovern et al. |
| 6,527,769 B2 | 3/2003 | Langberg et al. |
| 6,558,375 B1 | 5/2003 | Sinofsky et al. |
| 6,558,378 B2 | 5/2003 | Sherman et al. |
| 6,572,609 B1 | 6/2003 | Farr et al. |
| 6,572,612 B2 | 6/2003 | Stewart et al. |
| 6,579,285 B2 | 6/2003 | Sinofsky |
| 6,595,989 B1 | 7/2003 | Schaer |
| 6,599,288 B2 | 7/2003 | Maguire et al. |
| 6,605,055 B1 | 8/2003 | Sinofsky et al. |
| 6,605,084 B2 | 8/2003 | Acker et al. |

(56) References Cited

U.S. PATENT DOCUMENTS

| | | |
|---|---|---|
| 6,607,502 B1 | 8/2003 | Maguire et al. |
| 6,635,027 B1 | 10/2003 | Cragg et al. |
| 6,635,054 B2 | 10/2003 | Fjield et al. |
| 6,641,553 B1 | 11/2003 | Chee et al. |
| 6,652,515 B1 | 11/2003 | Maguire et al. |
| 6,659,940 B2 | 12/2003 | Adler |
| 6,659,953 B1 | 12/2003 | Smanaweera et al. |
| 6,660,002 B1 | 12/2003 | Edwards et al. |
| 6,676,656 B2 | 1/2004 | Sinofsky |
| 6,692,430 B2 | 2/2004 | Adler |
| 6,692,431 B2 | 2/2004 | Kazakevich |
| 6,692,455 B2 | 2/2004 | Goode et al. |
| 6,692,461 B2 | 2/2004 | Wantink |
| 6,692,462 B2 | 2/2004 | Mackenzie et al. |
| 6,692,463 B1 | 2/2004 | Marteau et al. |
| 6,692,464 B2 | 2/2004 | Graf |
| 6,692,490 B1 | 2/2004 | Edwards |
| 6,702,782 B2 | 3/2004 | Miller et al. |
| 6,736,811 B2 | 5/2004 | Panescu et al. |
| 6,743,226 B2 | 6/2004 | Cosman et al. |
| 6,752,805 B2 | 6/2004 | Maguire et al. |
| 6,771,996 B2 | 8/2004 | Bowe et al. |
| 6,780,183 B2 | 8/2004 | Jimenez, Jr. et al. |
| 6,808,524 B2 | 10/2004 | Lopath et al. |
| 6,814,730 B2 | 11/2004 | Li |
| 6,869,431 B2 | 3/2005 | Maguire et al. |
| 6,872,183 B2 | 3/2005 | Sampson et al. |
| 6,872,206 B2 | 3/2005 | Edwards et al. |
| 6,887,235 B2 | 5/2005 | O'Conner et al. |
| 6,911,027 B1 | 6/2005 | Edwards et al. |
| 6,932,809 B2 | 8/2005 | Sinofsky |
| 6,937,899 B2 | 8/2005 | Sheldon et al. |
| 6,942,657 B2 | 9/2005 | Sinofsky et al. |
| 6,949,072 B2 | 9/2005 | Furnish et al. |
| 6,955,173 B2 | 10/2005 | Lesh |
| 6,976,956 B2 | 12/2005 | Takahashi et al. |
| 6,978,174 B2 | 12/2005 | Gelfand et al. |
| 7,004,923 B2 | 2/2006 | Deniega et al. |
| 7,030,904 B2 | 4/2006 | Adair et al. |
| 7,048,733 B2 | 5/2006 | Hartley et al. |
| 7,115,122 B1 | 10/2006 | Swanson et al. |
| 7,137,395 B2 | 11/2006 | Fried et al. |
| 7,150,745 B2 | 12/2006 | Stern et al. |
| 7,162,303 B2 | 1/2007 | Levin et al. |
| 7,166,075 B2 | 1/2007 | Varghese et al. |
| 7,169,140 B1 | 1/2007 | Kume |
| 7,207,984 B2 | 4/2007 | Farr et al. |
| 7,226,448 B2 | 6/2007 | Bertolero et al. |
| 7,232,437 B2 | 6/2007 | Berman et al. |
| 7,238,179 B2 | 7/2007 | Brucker et al. |
| 7,238,180 B2 | 7/2007 | Mester et al. |
| 7,267,674 B2 | 9/2007 | Brucker et al. |
| 7,285,116 B2 | 10/2007 | de la Rama et al. |
| 7,286,866 B2 | 10/2007 | Okerlund et al. |
| 7,291,146 B2 | 11/2007 | Steinke et al. |
| 7,293,562 B2 | 11/2007 | Malecki et al. |
| 7,300,397 B2 | 11/2007 | Adler et al. |
| 7,310,150 B2 | 12/2007 | Guillermo et al. |
| 7,320,677 B2 | 1/2008 | Brouillette |
| 7,344,533 B2 | 3/2008 | Pearson et al. |
| 7,346,381 B2 | 3/2008 | Okerlund et al. |
| 7,357,796 B2 | 4/2008 | Farr et al. |
| 7,365,859 B2 | 4/2008 | Yun et al. |
| 7,366,376 B2 | 4/2008 | Shishkov et al. |
| 7,367,975 B2 | 5/2008 | Malecki et al. |
| 7,371,231 B2 | 5/2008 | Rioux et al. |
| 7,382,949 B2 | 6/2008 | Bouma et al. |
| 7,396,355 B2 | 7/2008 | Goldman et al. |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,427,265 B1 | 9/2008 | Keilman et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,473,251 B2 | 1/2009 | Knowlton et al. |
| 7,481,808 B2 | 1/2009 | Koyfman et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,517,346 B2 | 4/2009 | Sloan et al. |
| 7,519,096 B2 | 4/2009 | Bouma et al. |
| 7,529,393 B2 | 5/2009 | Peszynski et al. |
| 7,534,204 B2 | 5/2009 | Starksen et al. |
| 7,538,859 B2 | 5/2009 | Tearney et al. |
| 7,585,273 B2 | 9/2009 | Adler et al. |
| 7,588,535 B2 | 9/2009 | Adler et al. |
| 7,617,005 B2 | 11/2009 | Demarais et al. |
| 7,620,451 B2 | 11/2009 | Demarais et al. |
| 7,653,438 B2 | 1/2010 | Deem et al. |
| 7,669,309 B2 | 3/2010 | Johnson et al. |
| 7,683,323 B2 | 3/2010 | Kymissis |
| 7,756,583 B2 | 7/2010 | Demarais et al. |
| 7,758,499 B2 | 7/2010 | Adler |
| 7,853,333 B2 | 12/2010 | Demarais |
| 7,879,029 B2 | 2/2011 | Jimenez |
| 7,928,113 B2 | 4/2011 | Neamati et al. |
| 7,935,108 B2 | 5/2011 | Baxter et al. |
| 7,937,143 B2 | 5/2011 | Demarais et al. |
| 7,951,144 B2 | 5/2011 | Mahajan et al. |
| 8,007,440 B2 | 8/2011 | Magnin et al. |
| 8,025,661 B2 | 9/2011 | Arnold et al. |
| 8,078,266 B2 | 12/2011 | Saadat et al. |
| 8,167,805 B2 | 5/2012 | Emery et al. |
| 8,172,747 B2 | 5/2012 | Wallace et al. |
| 8,194,121 B2 | 6/2012 | Blumzvig et al. |
| 8,295,902 B2 | 10/2012 | Salahieh et al. |
| 8,323,241 B2 | 12/2012 | Salahieh et al. |
| 8,333,012 B2 | 12/2012 | Rothe et al. |
| 8,337,492 B2 | 12/2012 | Kunis et al. |
| 8,361,041 B2 | 1/2013 | Fang et al. |
| 8,369,921 B2 | 2/2013 | Tegg et al. |
| 8,417,321 B2 | 4/2013 | Saadat et al. |
| 8,419,613 B2 | 4/2013 | Saadat et al. |
| 8,465,421 B2 | 6/2013 | Finkman et al. |
| 8,479,585 B2 | 7/2013 | Shaw-Klein |
| 8,540,704 B2 | 9/2013 | Melsky et al. |
| 8,560,086 B2 | 10/2013 | Just et al. |
| 8,617,150 B2 | 12/2013 | Tsoref et al. |
| 8,702,682 B2 | 4/2014 | Atanasoska et al. |
| 8,708,953 B2 | 4/2014 | Salahieh et al. |
| 8,728,073 B2 | 5/2014 | McDaniel |
| 8,777,857 B2 | 7/2014 | Sliwa et al. |
| 8,805,466 B2 | 8/2014 | Salahieh et al. |
| 8,808,281 B2 | 8/2014 | Emmons et al. |
| 8,840,601 B2 | 9/2014 | Salahieh et al. |
| 8,894,643 B2 | 11/2014 | Watson et al. |
| 8,920,369 B2 | 12/2014 | Salahieh et al. |
| 8,939,970 B2 | 1/2015 | Stone et al. |
| 8,968,591 B2 | 3/2015 | Nishikubo et al. |
| 8,981,625 B2 | 3/2015 | Nishikubo et al. |
| 9,037,259 B2 | 5/2015 | Mathur |
| 9,174,050 B2 | 11/2015 | Mathur et al. |
| 9,333,031 B2 | 5/2016 | Salahieh et al. |
| 9,445,862 B2 | 9/2016 | Brewster et al. |
| 9,586,025 B2 | 3/2017 | Salahieh et al. |
| 9,610,006 B2 | 4/2017 | Salahieh et al. |
| 9,655,677 B2 | 5/2017 | Salahieh et al. |
| 10,098,694 B2 | 10/2018 | Salahieh et al. |
| 2002/0002384 A1 | 1/2002 | Gilson et al. |
| 2002/0068934 A1 | 6/2002 | Edwards et al. |
| 2002/0087208 A1 | 7/2002 | Koblish et al. |
| 2002/0095147 A1 | 7/2002 | Shadduck |
| 2002/0111548 A1 | 8/2002 | Swanson et al. |
| 2002/0154215 A1 | 10/2002 | Schechterman et al. |
| 2002/0165535 A1 | 11/2002 | Lesh et al. |
| 2002/0183623 A1 | 12/2002 | Tang et al. |
| 2003/0050637 A1 | 3/2003 | Maguire et al. |
| 2003/0065371 A1 | 4/2003 | Satake |
| 2003/0097121 A1 | 5/2003 | Jolly et al. |

(56) References Cited

U.S. PATENT DOCUMENTS

| | | |
|---|---|---|
| 2003/0097129 A1 | 5/2003 | Davison et al. |
| 2003/0135101 A1 | 7/2003 | Webler |
| 2003/0233099 A1 | 12/2003 | Danaek et al. |
| 2003/0236443 A1 | 12/2003 | Cespedes et al. |
| 2004/0054363 A1 | 3/2004 | Vaska et al. |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0167503 A1 | 8/2004 | Sinofsky |
| 2004/0243118 A1 | 12/2004 | Ayers et al. |
| 2005/0004440 A1 | 1/2005 | Vanney |
| 2005/0065504 A1 | 3/2005 | Melsky et al. |
| 2005/0171527 A1 | 8/2005 | Bhola |
| 2005/0203394 A1* | 9/2005 | Hauck ............... A61B 5/0422 600/437 |
| 2005/0203597 A1 | 9/2005 | Yamazaki et al. |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2005/0245892 A1 | 11/2005 | Elkins et al. |
| 2006/0041277 A1 | 2/2006 | Deem et al. |
| 2006/0089632 A1 | 4/2006 | Barthe et al. |
| 2006/0100618 A1 | 5/2006 | Chan et al. |
| 2006/0173300 A1 | 8/2006 | Oslund et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0241589 A1 | 10/2006 | Heim et al. |
| 2006/0247701 A1 | 11/2006 | Zacouto |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0032727 A1 | 2/2007 | Omata |
| 2007/0073135 A1 | 3/2007 | Lee et al. |
| 2007/0078507 A1 | 4/2007 | Zacouto |
| 2007/0112422 A1 | 5/2007 | Dehdashtian |
| 2007/0118094 A1 | 5/2007 | Bingham et al. |
| 2007/0129720 A1 | 6/2007 | Demarais et al. |
| 2007/0129760 A1 | 6/2007 | Demarais et al. |
| 2007/0135875 A1 | 6/2007 | Demarais et al. |
| 2007/0213616 A1 | 9/2007 | Anderson et al. |
| 2007/0213671 A1 | 9/2007 | Hiatt |
| 2007/0219451 A1 | 9/2007 | Kula et al. |
| 2007/0225634 A1 | 9/2007 | Ferren et al. |
| 2007/0233185 A1 | 10/2007 | Anderson et al. |
| 2007/0244501 A1 | 10/2007 | Horn et al. |
| 2007/0255097 A1 | 11/2007 | Jung et al. |
| 2007/0270686 A1 | 11/2007 | Ritter et al. |
| 2007/0287994 A1 | 12/2007 | Patel |
| 2008/0004652 A1 | 1/2008 | Abboud et al. |
| 2008/0058590 A1 | 3/2008 | Saadat et al. |
| 2008/0058591 A1 | 3/2008 | Saadat et al. |
| 2008/0058836 A1 | 3/2008 | Moll et al. |
| 2008/0071173 A1 | 3/2008 | Aldrich |
| 2008/0108867 A1 | 5/2008 | Zhou |
| 2008/0125772 A1 | 5/2008 | Stone et al. |
| 2008/0188912 A1 | 8/2008 | Stone et al. |
| 2008/0205481 A1 | 8/2008 | Faries, Jr. et al. |
| 2008/0262489 A1 | 10/2008 | Steinke |
| 2008/0275300 A1 | 11/2008 | Rothe et al. |
| 2008/0275445 A1 | 11/2008 | Kelly et al. |
| 2008/0281293 A1 | 11/2008 | Peh et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0030276 A1 | 1/2009 | Saadat et al. |
| 2009/0030412 A1 | 1/2009 | Willis et al. |
| 2009/0046171 A1 | 2/2009 | Kogan et al. |
| 2009/0051763 A1 | 2/2009 | Adler et al. |
| 2009/0054786 A1 | 2/2009 | Beckermus |
| 2009/0054787 A1 | 2/2009 | Adler et al. |
| 2009/0054803 A1 | 2/2009 | Saadat et al. |
| 2009/0076498 A1 | 3/2009 | Saadat et al. |
| 2009/0125022 A1 | 5/2009 | Saadat et al. |
| 2009/0137893 A1 | 5/2009 | Seibel et al. |
| 2009/0203962 A1 | 8/2009 | Miller et al. |
| 2009/0227885 A1 | 9/2009 | Lowery et al. |
| 2009/0227999 A1 | 9/2009 | Willis et al. |
| 2009/0240249 A1 | 9/2009 | Chan et al. |
| 2009/0247933 A1 | 10/2009 | Maor et al. |
| 2009/0254142 A1 | 10/2009 | Edwards et al. |
| 2009/0275799 A1 | 11/2009 | Saadat et al. |
| 2009/0299354 A1 | 12/2009 | Melsky et al. |
| 2009/0312754 A1 | 12/2009 | Lenihan et al. |
| 2009/0318757 A1 | 12/2009 | Singh |
| 2009/0318759 A1 | 12/2009 | Jacobsen et al. |
| 2009/0326320 A1 | 12/2009 | Sinofsky et al. |
| 2009/0326321 A1 | 12/2009 | Jacobsen et al. |
| 2009/0326572 A1 | 12/2009 | Peh et al. |
| 2010/0016957 A1 | 1/2010 | Jager et al. |
| 2010/0087782 A1 | 4/2010 | Ghaffari et al. |
| 2010/0121142 A1 | 5/2010 | Ouyang et al. |
| 2010/0204560 A1 | 8/2010 | Salahieh et al. |
| 2010/0204561 A1 | 8/2010 | Saadat et al. |
| 2010/0238279 A1 | 9/2010 | Thoms et al. |
| 2011/0034790 A1 | 2/2011 | Mourlas et al. |
| 2011/0034912 A1 | 2/2011 | de Graff et al. |
| 2011/0040172 A1 | 2/2011 | Carpentier et al. |
| 2011/0046600 A1 | 2/2011 | Crank |
| 2011/0077579 A1 | 3/2011 | Harrison et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0152352 A1 | 6/2011 | Hata et al. |
| 2011/0160514 A1 | 6/2011 | Long et al. |
| 2011/0160584 A1 | 6/2011 | Paul et al. |
| 2011/0201973 A1 | 8/2011 | Stephens et al. |
| 2011/0237940 A1* | 9/2011 | Raleigh ............... A61B 1/00177 600/425 |
| 2011/0257523 A1 | 10/2011 | Hastings et al. |
| 2011/0292258 A1 | 12/2011 | Adler et al. |
| 2011/0301418 A1 | 12/2011 | Gharib et al. |
| 2011/0319752 A1 | 12/2011 | Steinberg et al. |
| 2012/0004529 A1 | 1/2012 | Tolkowsky et al. |
| 2012/0004537 A1 | 1/2012 | Tolkowsky et al. |
| 2012/0069367 A1 | 3/2012 | Iguchi |
| 2012/0071870 A1 | 3/2012 | Salahieh et al. |
| 2012/0116438 A1 | 5/2012 | Salahieh et al. |
| 2012/0130171 A1 | 5/2012 | Barak et al. |
| 2012/0165669 A1 | 6/2012 | Barley et al. |
| 2012/0302877 A1 | 11/2012 | Harks et al. |
| 2013/0079645 A1 | 3/2013 | Amirana et al. |
| 2013/0085493 A1 | 4/2013 | Bloom et al. |
| 2013/0137920 A1 | 5/2013 | Schaeffer et al. |
| 2013/0138082 A1 | 5/2013 | Salahieh et al. |
| 2013/0172726 A9 | 7/2013 | Saadat et al. |
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0204125 A1 | 8/2013 | Chang et al. |
| 2013/0204126 A1 | 8/2013 | Namati et al. |
| 2013/0231533 A1 | 9/2013 | Papademetriou et al. |
| 2013/0289350 A1 | 10/2013 | Lerner et al. |
| 2013/0289358 A1 | 10/2013 | Melsky et al. |
| 2013/0304065 A1 | 11/2013 | Lopes et al. |
| 2013/0317497 A1 | 11/2013 | Edwards et al. |
| 2014/0031810 A1 | 1/2014 | Mahvi et al. |
| 2014/0058197 A1 | 2/2014 | Salahieh et al. |
| 2014/0107623 A1 | 4/2014 | Salahieh et al. |
| 2014/0121470 A1 | 5/2014 | Scharf et al. |
| 2014/0171942 A1 | 6/2014 | Werneth et al. |
| 2014/0180273 A1 | 6/2014 | Nair |
| 2014/0213850 A1 | 7/2014 | Levy et al. |
| 2014/0243680 A1 | 8/2014 | Raleigh |
| 2014/0296643 A1 | 10/2014 | Levy et al. |
| 2014/0296866 A1 | 10/2014 | Salman et al. |
| 2014/0309495 A1 | 10/2014 | Kirma et al. |
| 2014/0316198 A1 | 10/2014 | Krivopisk et al. |
| 2014/0320617 A1 | 10/2014 | Parks et al. |
| 2014/0333743 A1 | 11/2014 | Gilreath et al. |
| 2014/0357956 A1 | 12/2014 | Salahieh et al. |

(56) References Cited

U.S. PATENT DOCUMENTS

| | | |
|---|---|---|
| 2014/0358140 A1 | 12/2014 | Emmons et al. |
| 2014/0364691 A1 | 12/2014 | Krivopisk et al. |
| 2014/0364692 A1 | 12/2014 | Salman et al. |
| 2014/0364694 A1 | 12/2014 | Avron et al. |
| 2014/0370072 A1 | 12/2014 | Hossainy et al. |
| 2015/0073341 A1 | 3/2015 | Salahieh et al. |
| 2015/0094656 A1 | 4/2015 | Salahieh et al. |
| 2015/0327753 A1 | 11/2015 | Amirana et al. |
| 2015/0351836 A1 | 12/2015 | Prutchi |
| 2016/0051321 A1 | 2/2016 | Salahieh et al. |
| 2016/0157954 A1 | 6/2016 | Sagon et al. |
| 2017/0027601 A1 | 2/2017 | Salahieh et al. |
| 2017/0042614 A1 | 2/2017 | Salahieh et al. |
| 2017/0042615 A1 | 2/2017 | Salahieh et al. |
| 2017/0080184 A1 | 3/2017 | Salahieh et al. |
| 2017/0173303 A1 | 6/2017 | Salahieh et al. |

FOREIGN PATENT DOCUMENTS

| | | |
|---|---|---|
| CN | 101505672 A | 8/2009 |
| CN | 101511292 A | 8/2009 |
| CN | 101888813 A | 11/2010 |
| CN | 101956919 A | 1/2011 |
| CN | 203271765 A | 9/2013 |
| DE | 4104092 A1 | 8/1991 |
| EP | 0322852 A1 | 7/1989 |
| EP | 0802768 A | 10/1997 |
| EP | 0637943 B1 | 4/1998 |
| EP | 623360 B1 | 3/1999 |
| EP | 0723467 B1 | 4/2002 |
| EP | 0693955 B1 | 1/2003 |
| EP | 1382366 A1 | 1/2004 |
| EP | 1463441 A2 | 10/2004 |
| EP | 1604613 A1 | 12/2005 |
| EP | 1991301 A2 | 11/2008 |
| EP | 2335757 A2 | 6/2011 |
| JP | H08-504333 A | 5/1996 |
| JP | 2000-504242 A | 4/2000 |
| JP | 2003510126 A | 3/2003 |
| JP | 2004237077 A | 8/2004 |
| JP | 2008142346 | 6/2006 |
| JP | 2007516010 | 6/2007 |
| JP | 2009507617 | 2/2009 |
| JP | 2009539575 | 11/2009 |
| JP | 2010507403 A | 3/2010 |
| JP | 2010507404 A | 3/2010 |
| JP | 2012525898 A | 10/2012 |
| WO | WO87/05748 A1 | 9/1987 |
| WO | WO95/05775 A1 | 3/1995 |
| WO | WO95/10319 A1 | 4/1995 |
| WO | WO98/31271 A2 | 7/1998 |
| WO | WO 99/00060 A1 | 1/1999 |
| WO | WO99/02096 A1 | 1/1999 |
| WO | WO99/26530 A1 | 6/1999 |
| WO | WO99/42176 A1 | 8/1999 |
| WO | WO99/44519 A2 | 9/1999 |
| WO | WO99/45855 A1 | 9/1999 |
| WO | WO00/38580 A1 | 7/2000 |
| WO | WO00/56237 A2 | 9/2000 |
| WO | WO 00/66014 A1 | 11/2000 |
| WO | WO00/67648 A1 | 11/2000 |
| WO | WO00/67656 A1 | 11/2000 |
| WO | WO01/08575 A2 | 2/2001 |
| WO | WO01/08576 A2 | 2/2001 |
| WO | WO01/13812 A1 | 3/2001 |
| WO | WO01/68178 A1 | 9/2001 |
| WO | WO01/72373 A2 | 10/2001 |
| WO | WO01/87169 A1 | 11/2001 |
| WO | WO01/87174 A1 | 11/2001 |
| WO | WO01/95820 A1 | 12/2001 |
| WO | WO02/40089 A2 | 5/2002 |
| WO | WO03/013624 A2 | 2/2003 |
| WO | WO05/32370 | 4/2005 |
| WO | WO2005/065563 A1 | 7/2005 |
| WO | WO2006/077573 A1 | 7/2006 |
| WO | WO2007/001981 A2 | 1/2007 |
| WO | WO2007/047993 A2 | 4/2007 |
| WO | WO2007/059195 A1 | 5/2007 |
| WO | WO2008/061152 A2 | 5/2008 |
| WO | WO 2009/067695 A1 | 5/2009 |
| WO | WO 2009/088678 A1 | 7/2009 |
| WO | WO 2009/132137 A1 | 10/2009 |
| WO | WO2009/151600 A2 | 12/2009 |
| WO | WO 2009/155441 A2 | 12/2009 |
| WO | 2011143468 A3 | 11/2011 |
| WO | WO2011/153434 A2 | 12/2011 |
| WO | WO2012/033837 A2 | 3/2012 |
| WO | WO 2013/049601 A2 | 4/2013 |
| WO | WO2013/098732 A1 | 7/2013 |
| WO | 2014036439 A2 | 3/2014 |
| WO | WO2014/100259 A1 | 6/2014 |
| WO | WO2014168987 A1 | 10/2014 |

OTHER PUBLICATIONS

International Preliminary Report on Patentability issued in PCT/US2016/039646; dated Jan. 4, 2018, 6 pages.

International Preliminary Report on Patentability issued in PCT/US2016/062323, dated May 31, 2018, 10 pages.

International Search Report and Written Opinion issued in PCT/US2016/062323, dated Apr. 5, 2017, 15 pages.

Tymecki, Lukasz, et al. "Strip Thick-Film Silver Ion-Selective Electrodes." Sensors and Actuators B 96 (2003), pp. 482-488.

Salahieh et al.; U.S. Appl. No. 15/339,724 entitled "Ablation catheters," filed Oct. 31, 2016.

Salahieh et al.; U.S. Appl. No. 15/339,745 entitled "Ablation catheters," filed Oct. 31, 2016.

Denham et al.; Ultrasonic resonant modes of piezoelectric balloons under internal pressure; J. Acoust. Soc. Am.; 132(3); pp. 1368-1377; Sep. 2012.

Foley et al.; Computer Graphics Principles and Practice; 2nd Edition; Addison Wesley (publisher); pp. 835-843; Jun. 1990.

Gibson; Visualization of lesion transmurality and depth of necrosis using an ablation catheter that incorporates ultrasound imaging: a small step or a major leap forward on the road to a more durable catheter ablation procedure for treatment of atrial fibrillation; Heart Rhythm; 8(2); pp. 313-314; Feb. 2011.

Hu et al.; In-vivo pan/tilt endoscope with integrated light source; Intelligent Robots and Systems; IROS 2007. IEEE/RSJ International Conference on; pp. 1284-1289; San Diego, CA, USA: Oct. 29-Nov. 2, 2007.

Tymecki et al; Strip thick-film silver ion-selective electrodes; Sensors and Actuators B; 96(3); pp. 482-488; Dec. 1, 2003.

Wippermann et al.; Low cost video endoscopes with simplified integration; In SPIE Photonics Europe; International Society for Optics and Phtonics; vol. 7716; pp. 77160M-1-77160M-9; Apr. 30, 2010.

Wright et al.; Real-time lesion assessment using a novel combined ultrasound and radiofrequency ablation catheter; Heart Rhythm; 8(2); pp. 304-312; Feb. 2011.

Wu et al.; Transmural ultrasound imaging of thermal lesion and action potential changes in perfused canine cardiac wedge preparations by high intensity focused ultrasound ablation; Plos One; 8(12); pp. 1-13; Dec. 2013.

Salahieh et al.; U.S. Appl. No. 13/830,624 entitled "Local Sympathectomy for PVD," filed Mar. 14, 2013.

Salahieh et al.; U.S. Appl. No. 61/622,495 entitled "Energy Delivery Device with Rapid Exchange Features," filed Apr. 10, 2012.

Salahieh et al.; U.S. Appl. No. 61/624,206 entitled "Energy delivery device and methods of use," filed Apr. 13, 2012.

Salahieh et al.; U.S. Appl. No. 15/082,923 entitled "Steerable medical devices, systems, and methods of use," filed Mar. 28, 2016.

Salahieh et al.; U.S. Appl. No. 15/092,442 entitled "Intravascular tissue disruption," filed Apr. 6, 2016.

Salahieh et al.; U.S. Appl. No. 15/138,050 entitled "Steerable medical devices, systems, and methods of use," filed Apr. 25, 2016.

Salahieh et al.; U.S. Appl. No. 15/167,509 entitled "Intravascular tissue disruption," filed May 27, 2016.

(56) References Cited

OTHER PUBLICATIONS

Extended European Search Report issued in EP Application 14782484.1, dated Oct. 31, 2016, 9 pages.
International Preliminary Report on Patentability issued in PCT/US2014/033393, dated Oct. 13, 2015, 11 pages.
International Search Report issued in PCT/US2014033393, dated Aug. 19, 2014, 5 pages.
Salahieh et al.; U.S. Appl. No. 15/375,027 entitled "Steerable medical devices, systems, and methods of use," filed Dec. 9, 2016.
Salahieh et al.; U.S. Appl. No. 15/452,413 entitled "Steerable delivery sheaths," filed Mar. 7, 2017.
Salahieh et al.; U.S. Appl. No. 15/640,306 entitled "Ablation catheters," filed Jun. 30, 2017.

* cited by examiner

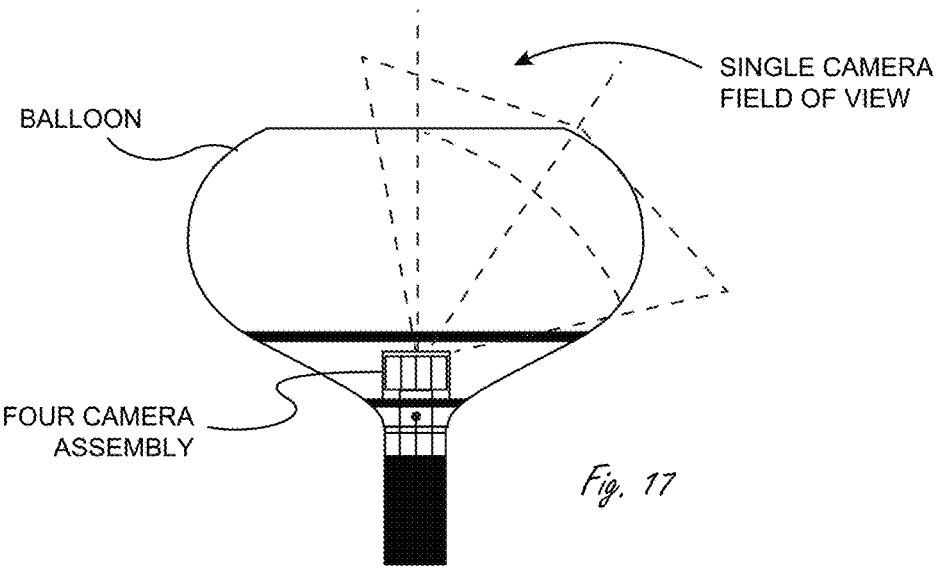
Fig. 17
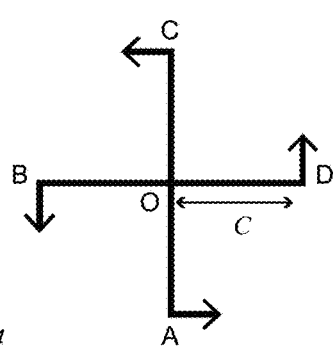
Fig. 18A
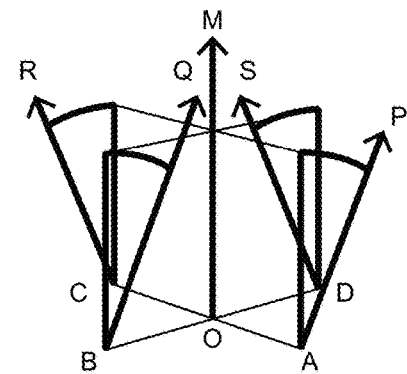
Fig. 18B
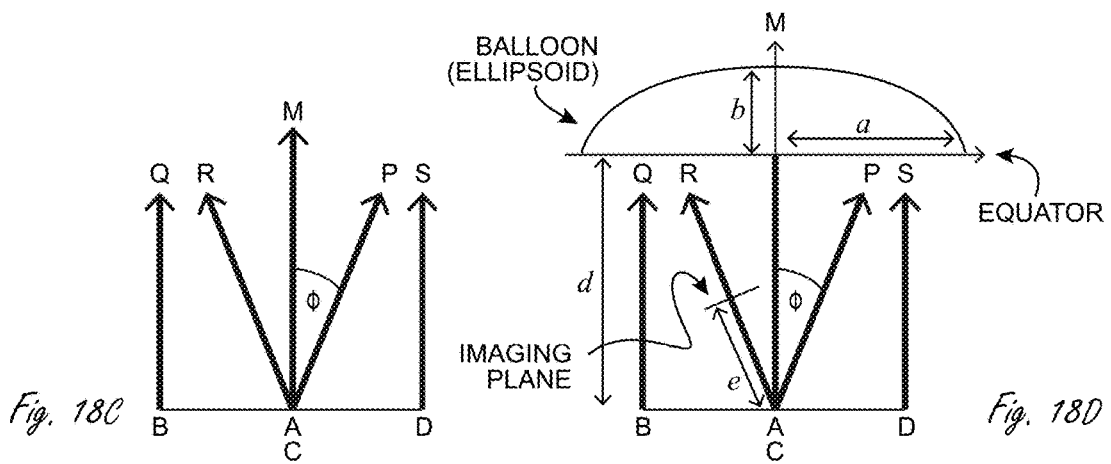
Fig. 18C
Fig. 18D

Fig. 33

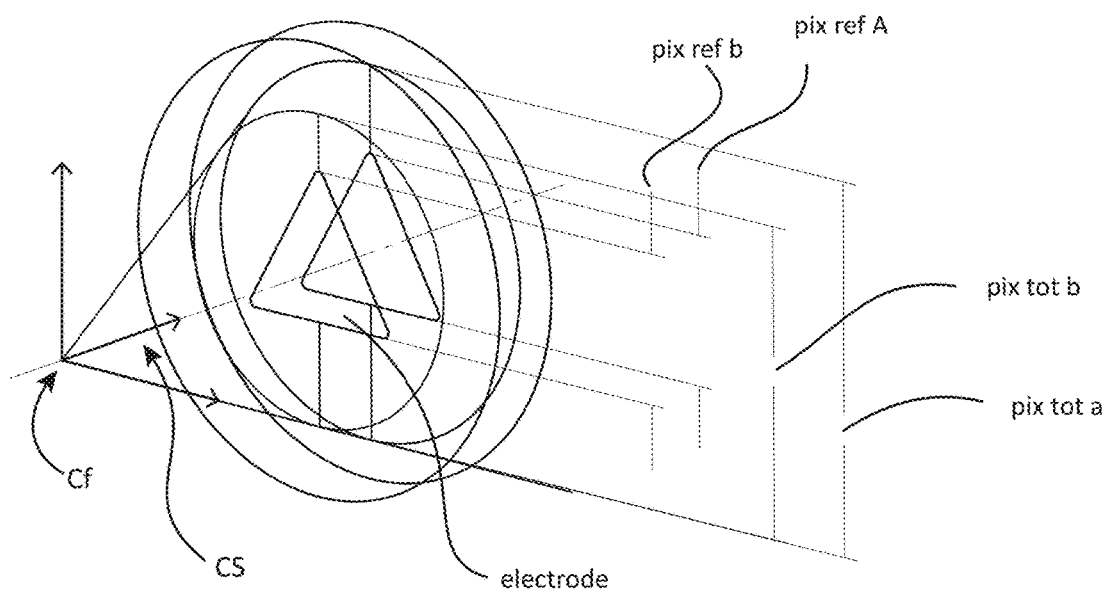
Fig. 49A
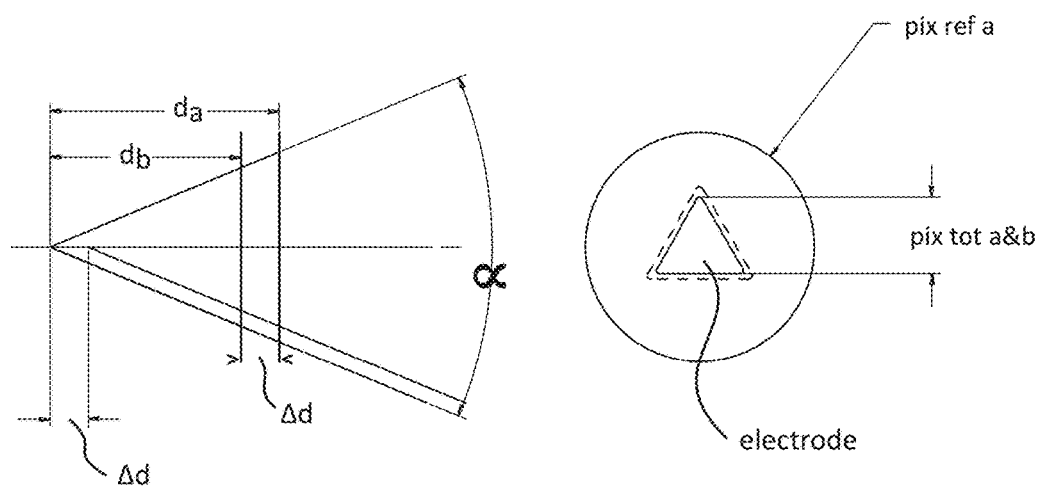
Fig. 49B
Fig. 49C

TISSUE MAPPING AND VISUALIZATION SYSTEMS

CROSS REFERENCE TO RELATED APPLICATIONS

This application claims the benefit of priority of U.S. Provisional Appln. No. 62/185,356, filed Jun. 26, 2015, the disclosure of which is incorporated by reference herein.

This application is also a continuation-in-part of U.S. application Ser. No. 14/248,288, filed Apr. 8, 2014, now issued U.S. Pat. No. 9,717,557, which application claims the benefit of priority of the following fourteen U.S. Provisional Applications, the disclosures of which are incorporated by reference herein: Appln. No. 61/809,629, filed Apr. 8, 2013; Appln. No. 61/809,646, filed Apr. 8, 2013; Appln. No. 61/895,880, filed Oct. 25, 2013; Appln. No. 61/809,636, filed Apr. 8, 2013; Appln. No. 61/864,335, filed Aug. 9, 2013; Appln. No. 61/829,985, filed May 31, 2013; Appln. No. 61/820,992, filed May 8, 2013; Appln. No. 61/821,001, filed May 8, 2013; Appln. No. 61/821,014, filed May 8, 2013; Appln. No. 61/934,640, filed Jan. 31, 2014, Appln. No. 61/939,185, filed Feb. 12, 2014; Appln. No. 61/934,647, filed Jan. 31, 2014; Appln. No. 61/945,005, filed Feb. 26, 2014, and Appln. No. 61/947,950, filed Mar. 4, 2014. All of the above-mentioned disclosures are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Some previous tissue mapping systems acquire the position of multiple points on the surface of the tissue to be mapped, and use the individual point positions to generate an image of the target tissue surface by interpolating a surface between the individual points. To acquire the position of each point, a user positions a probe at the point on the surface, and the position of the point is recorded. The user moves the probe to multiple points on the surface, and the position is recorded for each point. To create a 3D model of the surface using this and similar methods, the mapping probe must be moved to a relatively large number of points on the surface to be mapped, which increases the procedure time. Additionally, models generated using these techniques include measured position information only for the points that are actually touched by the probe during the mapping procedure; the rest of the surface points are interpolated and thus subject to error.

It would be beneficial to be able to map tissue without having to use methods that require a point-by-point position sensing in order to create a model of the target tissue.

SUMMARY OF THE DISCLOSURE

The disclosure relates generally to devices and systems adapted for, and methods of, creating a patient map.

One aspect of the disclosure is a method of using of a cardiac visualization catheter to create a patient map, comprising: positioning an ablation catheter within a patient adjacent tissue to be mapped, the ablation catheter comprising an expandable member that includes an expandable membrane, at least one camera disposed within the expandable membrane, the camera having a field of view, the camera orientated such that the camera field of view includes a portion of the expandable membrane when the expandable membrane is expanded, and a locational element with a fixed position and orientation relative to the camera, wherein the position and orientation of the location element are defined in a global frame of reference and detectable by a locational element detector; delivering a fluid into the expandable membrane to at least partially inflate the expandable membrane; contacting the patient with at least a portion of the expandable membrane; capturing, with the camera, a plurality of different 2D images of the patient's anatomy adjacent the expandable member, each of which visualizes at least one part of the patient that is in contact with the expandable membrane; tagging each of the plurality of different 2D images with information indicative of the position and orientation of the locational element when each of the plurality of different 2D images was captured; creating a patient map, wherein creating the patient map comprises placing each of the plurality of different 2D images at the corresponding tagged position and orientation into a 3 space, and displaying the patient map.

In some embodiments the ablation catheter includes a plurality of cameras disposed within the expandable membrane, each of the plurality of cameras having a different field of view, the locational element having a fixed position and orientation relative to each of the cameras, and wherein capturing a plurality of different 2D images with the camera comprises capturing a plurality of different 2D images with the plurality of cameras, each of the different 2D images including the fields of view of the plurality of cameras, and wherein the tagging step comprises tagging each of the plurality of different 2D images with information indicative of the position and orientation of the locational element when each of the plurality of 2D images was captured.

In some embodiments creating the patient map comprises projecting the plurality of different 2D images onto a 2D plane, and wherein displaying the patient map comprises displaying the 2D plane.

In some embodiments creating the patient map comprises a 2D patient map projected on a surface defined in a 3D volume where the surface is non planar.

In some embodiments the method further comprises mapping at least one natural landmark into the patient map. Mapping at least one natural landmark into the patient map can comprise mapping at least one pulmonary vein ostium into the patient map.

In some embodiments the method further comprises mapping at least one electrical landmark into the patient map. Mapping at least one electrical landmark into the patient map can comprise mapping at least one electrical landmark selected from the group consisting of: an electrophysiological landmark, a rotor, a nerve cell cluster, a nerve disposed on an inner wall of heart, and a nerve extending adjacent the heart, a conduction bundle within the heart. In some embodiments the electrical landmark is a nerve, the method further comprising delivery energy into tissue and monitoring for a response indicative that the delivery energy into tissue modulated activity in the nerve. In some embodiments the electrical landmark is a conduction bundle, the method further comprising delivery energy into tissue and monitoring for a response indicative that the delivery energy into tissue modulated activity in the conduction bundle. In some embodiments mapping at least one electrical landmark into the patient map comprises sensing electrical activity of tissue in the heart, and mapping the location of aberrant electrical activity.

In some embodiments the method further comprises mapping at least one created landmark into the patient map. Mapping at least one created landmark into the patient map can comprise mapping a zone indicative of where the expandable membrane has made contact with tissue, or has not made contact with tissue. The method can further comprise distinguishing a color in the plurality of images that indicates that contact with tissue has been made from a color in the plurality of image that indicates that contact with tissue has not been made. Mapping at least one created landmark into the tissue map can comprise mapping into the patient map a region of tissue into which ablation energy has been delivered. The method can further comprise injecting a dye into the tissue, and mapping the location of the dye into the patient map.

In some embodiments the camera has a reference frame, the camera reference frame in a fixed position and orientation relative to the location element, and wherein tagging each of the plurality of different images with information indicative of the position and orientation of the locational element when each of the plurality of images was captured comprises determining a position vector in the camera field of view in the global frame of reference. Determining the position vector can comprise using a known distance between the camera and a first scaling element carried by the expandable membrane. The first distance element can be a hub at a distal region of the device, the hub secured directly or indirectly to the expandable membrane. In some embodiments determining the position vector comprises estimating by calculating a distance between the camera and a point on the tissue. Estimating by calculating a distance between the camera and a point on the tissue can use a change in a known image dimension of a marker carried by the expandable member within the image.

In some embodiments the method further comprises delivering a fluid into the expandable membrane and creating a fluid pressure within the membrane that is greater than a threshold, the created fluid pressure creating a substantially constant distance between the camera and the expandable member when the expandable member is pressed against atrial tissue. Pressing the expandable member against atrial tissue can cause the atrial tissue to deform around the expandable member due to the created fluid pressure.

One aspect of the disclosure is an ablation catheter comprising: an expandable membrane, at least one camera disposed within the expandable membrane, the camera having a field of view, the camera orientated such that the camera field of view includes the expandable membrane when the expandable membrane is expanded, and a locational element with a fixed position and orientation relative to the camera, wherein the locational element is adapted such that the position and orientation of the location element can be defined in a global frame of reference and detectable by a locational element detector.

One aspect of the disclosure is a method of combining images from a cardiac ablation visualization system, comprising: providing a plurality of images captured with a visualization element disposed within an expandable member, combining the plurality of captured images using at least one common landmark between the plurality of captured images, wherein the at least one common landmark is selected from the group consisting of an anatomical landmark, an electrophysiological landmark, and a created landmark.

One aspect of the disclosure includes methods of stitching a plurality of images together using one or more landmarks, which can be any of the types of landmarks described herein. Stitching the images together can be done with or without the use of a locational element.

BRIEF DESCRIPTION OF THE DRAWINGS

FIG. 17 is a side view of a distal portion of an exemplary visualization catheter.

FIGS. 18A, 18B, 18C and 18D show the orientations of the axes of four cameras in relationship to the longitudinal axis of a catheter shaft.

FIGS. 32 and 33 illustrate aspects of an external console.

FIGS. 49A, 49B, and 49C illustrate an exemplary process using an exemplary marker to estimate CS.

DETAILED DESCRIPTION

Figure 1A:
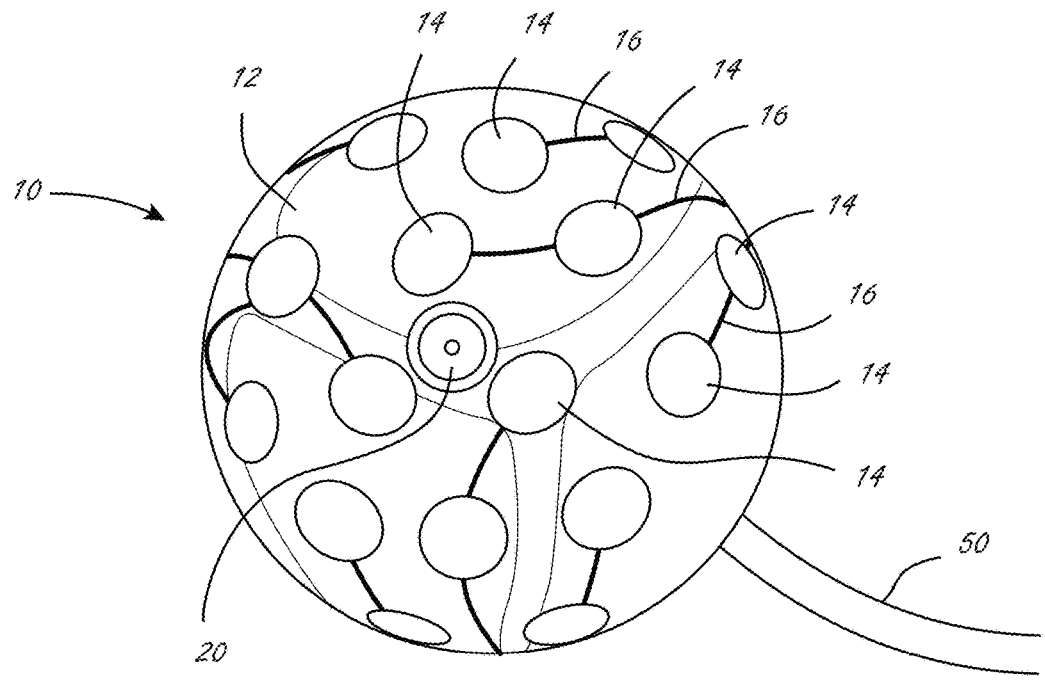
FIGS. 1A-1C illustrate an exemplary ablation device in expanded configurations.
Figure 1B:
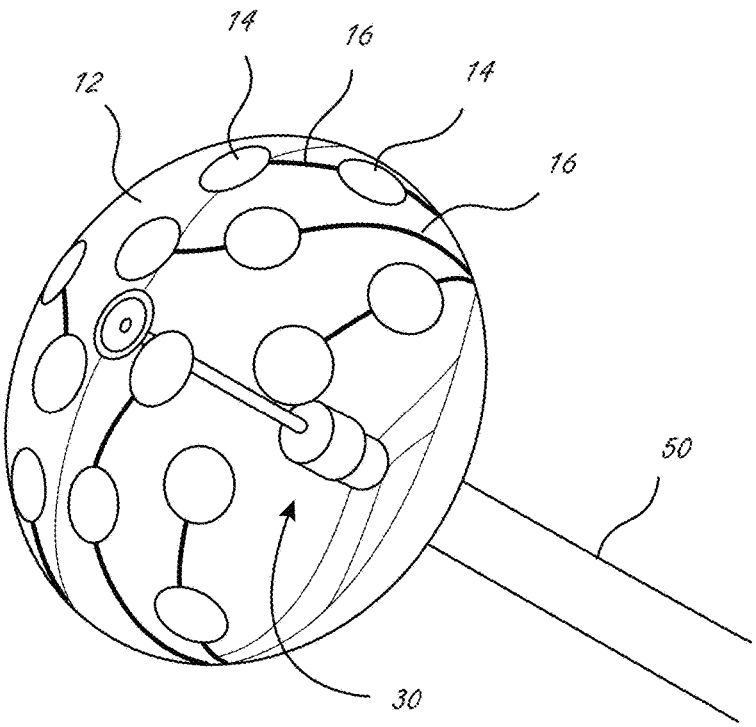
Figure 1C:
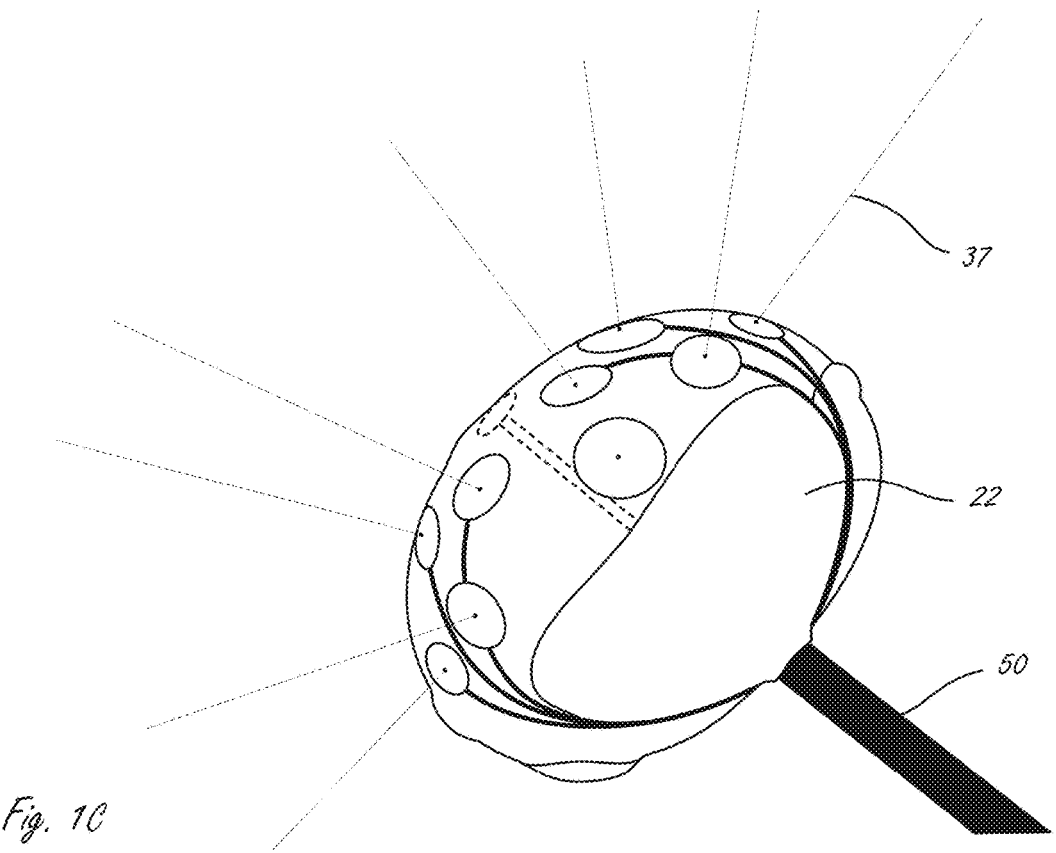

FIGS. 1A-1C illustrate a distal portion of an exemplary cardiac ablation catheter. FIGS. 1A-1C shows expandable member 10 in an expanded configuration. FIG. 1A is a distal view, FIG. 1B is a perspective view, and FIG. 1C is a side view.

The cardiac ablation catheter is configured to deliver ablative energy to tissue such as cardiac tissue and to ablate the tissue. Expandable member 10 includes membrane, or balloon, 12 and a plurality of energy delivery elements 14 secured to the exterior of membrane 12. In this embodiment energy delivery elements 14 are electrodes configured and positioned to deliver ablative RF energy to tissue when expandable member 10 is inflated and to ablate the tissue, and are in electrical communication with an RF generator (not shown) configured to generate RF energy.

Figure 1D:
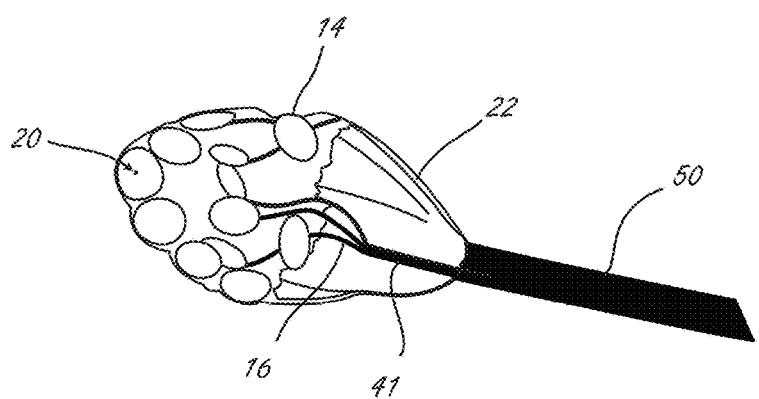
FIG. 1D illustrates an exemplary ablation device in a collapsed configuration.

FIG. 1D illustrates expandable member 10 in a collapsed, or deflated, configuration prior to full inflation.

Figure 2A:
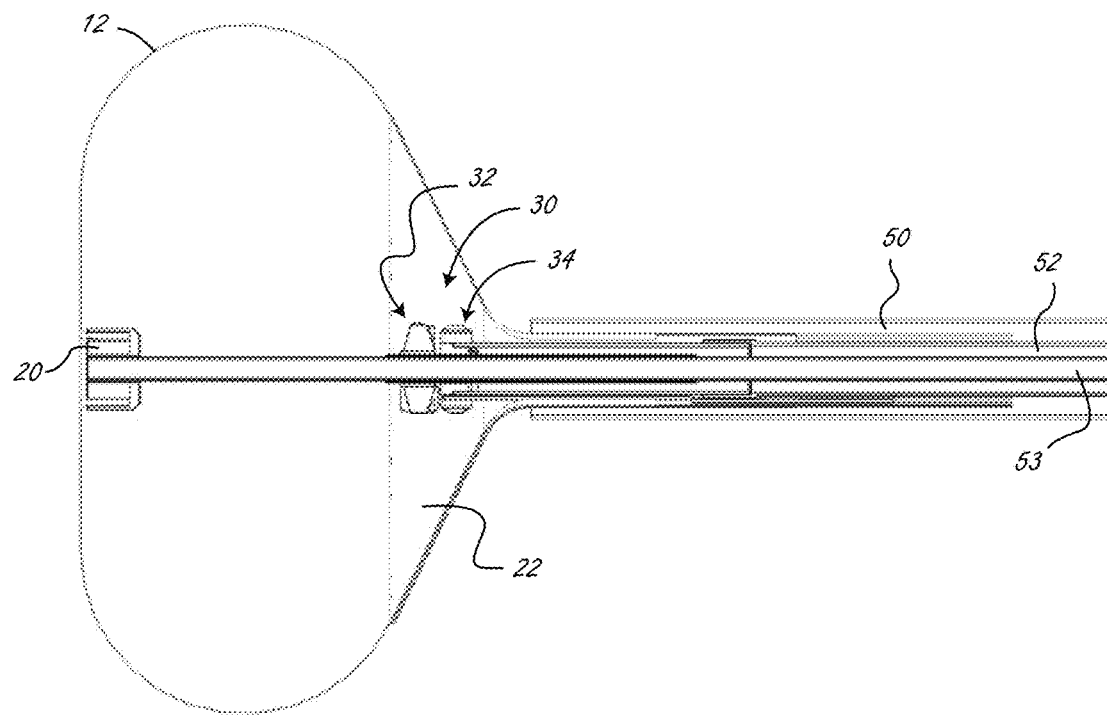
FIG. 2A is a side view of an exemplary distal end of an ablation catheter.
Figure 2B:
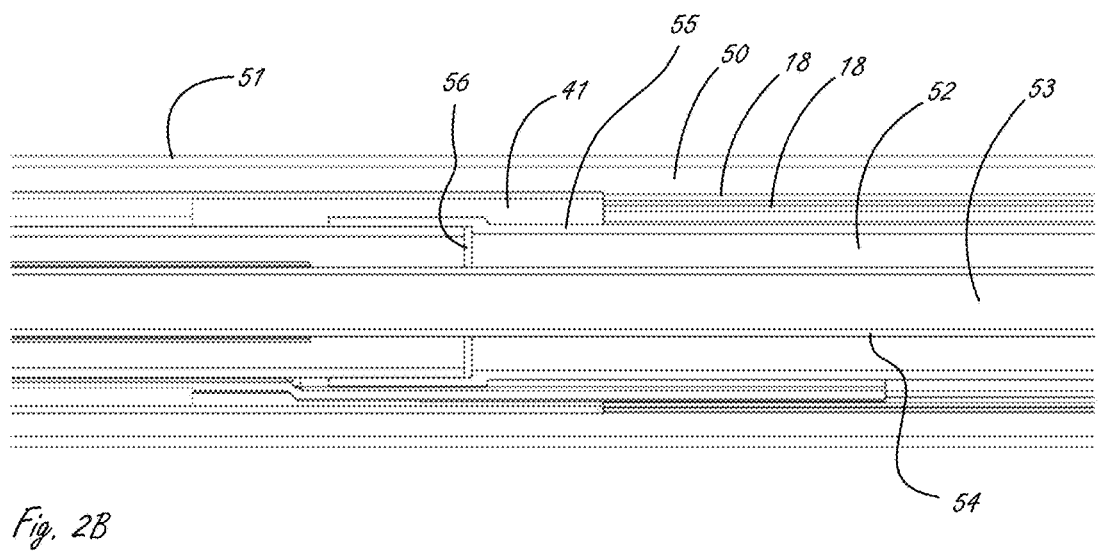
FIG. 2B is a close up side view of the inside of the catheter from FIG. 2A.

FIG. 2A is a side sectional view of the distal portion of the ablation catheter shown in FIGS. 1A-1C. FIG. 2B is a highlighted side sectional view of components within outer shaft 51. FIG. 2A shows membrane 12 expanded at the distal end of outer lumen 50, which is the annular space between outer shaft 51 and irrigation shaft 55. The distal end of membrane 12 is secured, such as by press-fit and/or adhesive, to distal hub assembly 20, between an inner member and an outer member of assembly 20 as shown. The proximal end of membrane 12 is secured to the outer surface of irrigation shaft 55. Hub 20 is secured to guide wire shaft 54, which in this embodiment defines guidewire lumen 53 so that the ablation catheter can be advanced over a guidewire (not shown). Guidewire shaft 54 and irrigation shaft 55 are adapted to be axially movable relative to one another, which allows the distal end of membrane 12 to be moved relative to the proximal end of membrane 12. Relative movement between the two components can allow for the shape of the balloon to be changed. The movement also assists in transitioning expandable member 10 to a collapsed configuration, as shown in FIG. 1D.

Visualization system 30 includes a camera assembly 32 and illumination sources 35 disposed on the guide wire shaft 54. The cameras are configured to enable real-time imaging of the procedure from within the expandable member 10 to visualize the membrane and electrodes, cardiac tissue when the membrane/electrodes and cardiac tissue interface, as well as lesion formation during the ablation procedure, as is described in more detail below.

FIG. 2B shows radially outer shaft 51, irrigation shaft 55 that defines irrigation lumen 52, and guide wire shaft 54 that defines guidewire lumen 53.

The materials of the membranes 12 described herein can vary. Generally, the membrane material is thin, readily foldable into a low profile and refoldable after expansion. The materials can be elastic, inelastic, stretchy, non-stretchy, compliant, semi-compliant, or non-compliant. In an embodiment, membrane 12 has an expandable structure and can be constructed of materials such as those materials used in the construction of balloon catheters known in the art, including, but not limited to polyvinyl chloride (PVC), polyethylene (PE), cross-linked polyethylene, polyolefins, polyolefin copolymer (POC), polyethylene terephthalate (PET), nylon, polymer blends, polyester, polyimide, polyamides, polyurethane, silicone, polydimethylsiloxane (PDMS) and the like. Membrane 12 can be constructed of relatively inelastic polymers such as PE, POC, PET, polyimide or a nylon material. Membrane 12 can be constructed of relatively compliant, elastomeric materials including, but not limited to, a silicone, latex, urethanes, or Mylar elastomers. Membrane 12 can be embedded with other materials such as for example, metal, Kevlar or nylon fibers. Membrane 12 can be constructed of a thin, non-extensible polymer film such as polyester or other flexible thermoplastic or thermosetting polymer film. In one embodiment flexible membrane 12 can be about 0.001" to about 0.002" in thickness to provide sufficient burst strength and allow for foldability. In some embodiments it is preferable to have the electrode mechanical properties as close to the membrane mechanical properties as possible. One way of providing this is to use an inelastic membrane that will not stretch as it is expanded. This helps secure the branches to the membrane. Membrane 12 has a front, or distal, face that is generally flat but can have other shapes as well.

Expandable member 10 includes what is generally referred to in U.S. Pat. No. 8,295,902, issued Oct. 23, 2012, and U.S. Pub. No. 2012/0071870, published Mar. 22, 2012, as flex circuits. A flex circuit as used herein generally refers to a conductive layer, an insulation layer, and optionally a substrate layer. A flex circuit is in electrical communication with at least one electrode.

Figure 8:
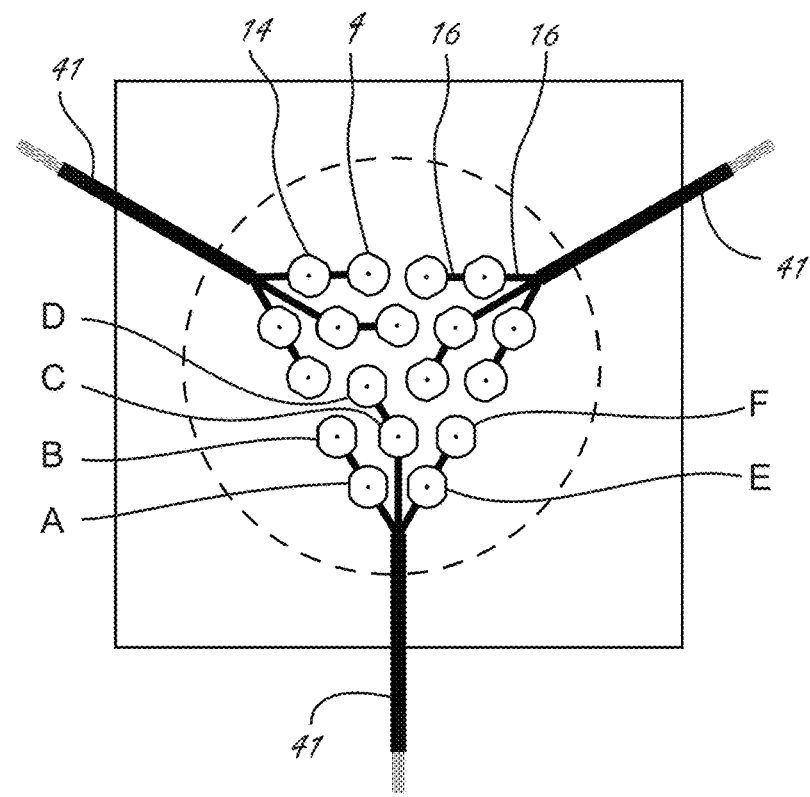
FIG. 8 is a flat view showing three individual flex circuits that are secured to the exterior of membrane and to electrodes.

FIG. 8 is a flat view showing three individual flex circuits that are secured to the exterior of membrane 12. Each of the three flex circuits includes six energy delivery elements 14, and a tail terminating in termination 41 for the six conductive traces, one for each of the six electrodes. The terminations may be in the form of a connector or solder pads or other such suitable interface. The terminations 41 extend proximally from energy delivery elements on the expandable member, one of which can be seen in FIG. 1D. Each of the tails branch off into three branches 16, each one of which includes two energy delivery elements. Each of the two side branches 16 extend away from the longitudinal axis of the connector at substantially the same angle and each of two electrodes on a side branch is disposed at the same axial position (in the distal/proximal direction) as the other corresponding electrode on the other side branch. The central branch, however, initially extends along the same general direction as the longitudinal axis of a tail, and the first electrode on the central branch is axially disposed at the same general location as the second electrodes on the right and left branch. The central branch then extends away from the longitudinal axis of the tail, and the second (distal) electrode on the central branch is disposed further distally than the other five electrodes on the flex circuit, and is disposed radially (relative the longitudinal axis of tail) at the same general position as the first (proximal) electrode on one of the other side branches. In FIG. 8, the six electrodes on one of the flex circuits are labeled A-F. The two side branches of the flex circuit include electrodes A-B and E-F respectively. The central branch includes electrodes C and D. In the flat view, electrode C (the distal electrode of the central branch) is axially disposed at the same general position as electrodes B and F. Electrode D is disposed further distally than the other five electrodes, and is positioned radially in the same general position as electrode A. Electrodes A and E are disposed in the same general axial position, as are electrodes B, C, and F. Each of the three flex circuits is positioned on the expandable member, and the arrangement and size of electrodes provides for eighteen electrodes secured to the expandable member. As can be seen in FIGS. 1A and 1B, there are three electrodes closely surrounding hub 20.

Figure 9A:
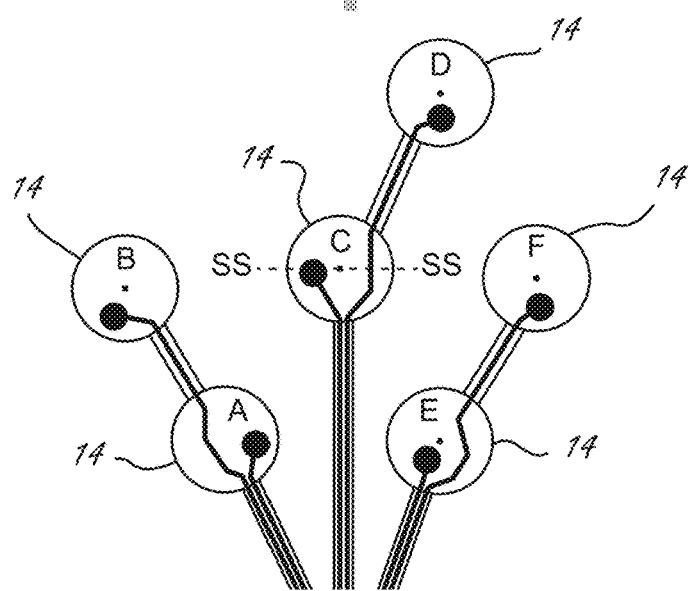
FIG. 9A illustrates a portion of one of the flex circuits and electrodes in FIG. 8.
Figure 9B:
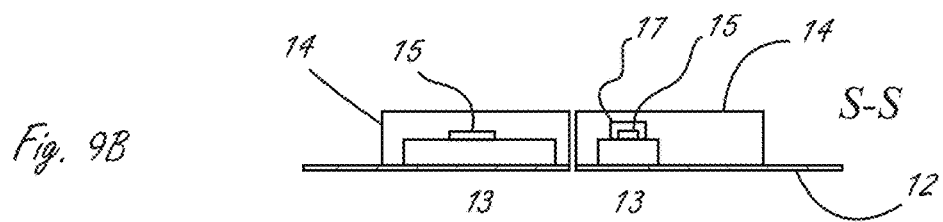
FIG. 9B illustrates the exemplary different layers of the flex circuit from section S-S from FIG. 9A.

FIG. 9A illustrates a portion of one of the flex circuits in FIG. 8 (the flex circuit in which termination 41 is at the "6 o'clock" position), including six energy delivery elements 14. FIG. 9A shows as alternative embodiment in which the distal electrode on the central branch 16 extends to the right on the page rather than the left, as is shown in FIG. 8. This arrangement provides the same general arrangement of the eighteen electrodes on the balloon. In the embodiment in FIGS. 1A-1C, there are three of the flex circuits from FIG. 9A disposed on membrane 12, and thus eighteen energy delivery elements secured to membrane 12. FIG. 9B illustrates the exemplary different layers of the flex circuit from section S-S from FIG. 9A. Electrically non-conductive substrate layer 13 is deposited on membrane 12, upon which conductive layers, or traces, 15 are deposited. Insulation layer 17 is deposited on top of conductive layers 15 except where the electrodes 14 are located. For example, to the left in FIG. 9B, an electrode 14 is disposed on electrically conductive element 15, thus electrically coupling electrode 14 and conductive layer 15, which is electrically coupled to an RF generator. On the right side of FIG. 9B, insulation layer 17 prevents conductor 15 on the right side from being electrically coupled to electrode 14. Instead, the conductor 15 on the right side will be electrically coupled to the distal electrode on that branch. Each individual conductor 15 is therefore electrically coupled to only one electrode 14. In the figure shown in 9A, there are six individual conductive traces 15, each of which is individually coupled to one electrode. As is described in detail in U.S. Pat. No. 8,295,902, issued Oct. 23, 2012; U.S. Pub. No. 2012/0071870, published Mar. 22, 2012, the electrodes are sized and configured to extend over a portion of the flex circuit and a portion of membrane not covered by the flex circuit. In this manner a large surface area electrode can be deposited onto and secured to the membrane. Each electrode is shown with an irrigation aperture in the middle thereof, as is described herein to irrigate tissue adjacent the electrodes and to prevent the irrigation fluid inside the membrane from becoming too hot and interfering with the tissue ablation.

The conductor or conductive layer 15 can be a material such as, but not limited to, a metal or metal foil of copper, gold, silver, tin, nickel, steel, cupronickel (copper-nickel alloy), KOVAR (nickel-cobalt ferrous alloy) or other material. In an embodiment, more than one conductive material can be used in the conductive layer 15. In an embodiment, a conductive layer 15 of copper can be plated with a thin layer of an additional conductive material at the conductive pad beneath electrode 14. In an embodiment, the thin layer of additional conductive material can be gold. The flex circuit and its components can be manufactured using techniques as known in the art.

The materials used to create the electrodes 14 can vary. The electrodes 14 can be a thin film of an electro-conductive or optical ink. The ink can be polymer-based for better adhesion to the membrane. The electrode material can be a biocompatible, low resistance metal such as silver, silver flake, gold, and platinum which are additionally radiopaque. Inks may additionally comprise materials such as carbon and/or graphite in combination with the more conductive materials already described. The addition of carbon and/or graphite can increase the conductivity of the polymer matrix. When incorporated as fibers the carbon and/or graphite add additional structural integrity to the ink electrode. Other fiber materials may be substituted to attain the same end. When the electrode material is not particularly radiopaque, additives such as tantalum and tungsten may be blended with the electrode material to enhance radiopacity. An example of an electro-conductive ink is provided by Engineered Conductive Materials, LLC (ECM) which is a polyurethane-based silver loaded ink. Another example is Creative Materials Inc., which manufactures conductive inks, films, as well as radiopaque inks. As mentioned above, the electrodes 14 can be applied to the membrane 12 and flex circuit using an adhesive. Alternatively, the electrode material can have adhesive properties or be an adhesive-loaded with conductive particles such as silver flakes such that electrodes 14 can adhere the components of the flex circuit to the membrane 12. If an additional adhesive layer is used to adhere the electrode 14 to the membrane 12 and flex circuit, the adhesive layer can include a conductive or non-conductive material. The electrodes formed with electro-conductive or optical ink or thin metal film can be visualized under fluoroscopy to provide a general sense of the shape of the membrane and location of the electrode. To enhance visualization under fluoroscopy, radiopaque additives can be included in the electrode material or radiopaque markers laid out next to, on top or below the electrodes as will be discussed in more detail below. Additionally, the bonding layer or substrate will be optimally comprised of a minimally reflective material.

Each of the electrodes is individually addressable, or can be used with any other electrode. The electrodes can operate in monopolar mode or bipolar mode, as is indicated in the exemplary schematic shown in FIG. 34. Electrodes sets can be chosen such that the lesion is, for example without limitation, linear, a spot, or a hollow circle.

Figure 3:
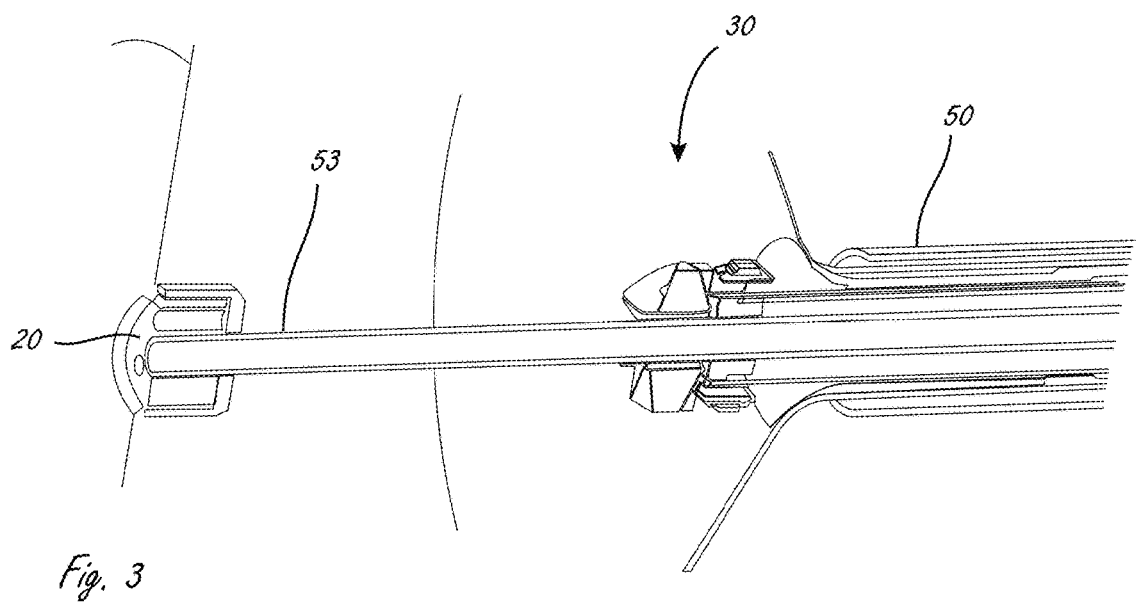
FIG. 3 is a perspective view showing inside the expandable membrane.

FIG. 3 illustrates the coupling of the distal end of membrane 12 and hub 20, which can be press fit, adhesive coupling or a combination of both.

To prevent or reduce the likelihood of charring of tissue that is in contact with the energy delivery elements and coagulation of blood adjacent the electrodes, each of the flex circuits at the locations of the electrodes includes an irrigation aperture therethrough, and as shown are in the center of the electrodes. The irrigation apertures also prevent the inflation/irrigation fluid inside the membrane from becoming too hot, which would interfere with the ablation. Irrigation fluid, which is also the fluid that inflates membrane 12 causing it to be reconfigured toward its expanded configuration, is pumped from a fluid source through irrigation lumen 52, into membrane 12, through the irrigation apertures (not labeled), and towards the tissue that is in contact with the electrodes to cool the target tissue. One of the drawbacks of previous attempts at cardiac ablation is that the ablation procedures cause blood to coagulate or tissue to char due to lack of a cooling feature. Additionally, since each electrode is individually addressable, and the visualization system allows the operator to identify whether an individual electrode is in contact with tissue, only electrodes in contact with tissue may be turned on. Thus energy is more efficiently coupled to just the sites where ablation is desired and little to no energy is dissipated into the blood.

One of the significant advantages of ablation catheters herein is that, when in use, the ablation procedures can be visualized with an imaging, or visualization, member with a perspective from within the inflatable membrane. In the embodiment in FIGS. 1A-1D, imaging member 30 includes camera assembly 32 that includes a plurality of cameras 33 and a plurality of illumination, or light, sources, 35 (e.g., LEDs). Expandable member 10 also includes diffuse reflector 22 that is secured to the external surface of membrane 12. Reflector 22 is a diffuse reflector adapted to create diffuse reflection of light incident upon it from the illumination sources. Reflector 22 is adapted to reflect light in a diffuse manner, as opposed to specular reflection, to better illuminate as much of the camera field of view as possible. If the reflector were adapted for specular reflection rather than diffuse reflection, light from the illumination sources that is reflected from the reflector would appear in the camera's field of view as a localized spot and would not illuminate as much of the field of view as possible.

Illumination sources 35 are configured and positioned to provide illumination generally radially outward towards reflector 22. Diffuse reflector 22 thus diffusely reflects light forward toward the camera's fields of view. The illumination sources thus provide lighting for the cameras to visualize the procedure, including the tissue, and the lesion formation.

In some embodiments the diffuse reflector is printed on the exterior of the balloon. The diffuse reflector can be comprised of silicone or urethane resins filled with nonconductive white pigment such as TiO, BaO, BaSo4, styrene or other polymer beads, or of metal particles. Optimal materials will be minimally reflective such as a black adhesive.

In this embodiment the diffuse reflector is secured to the membrane such that it does not completely overlap any of the electrodes, and is positioned so that the illumination sources, when activated, emit light towards the reflector. In this embodiment the diffuse reflector, or reflectors, is secured to the membrane at a location that does not extend all the way to the distal end of the membrane. In this embodiment the reflector is secured to the membrane such that it does not extend further distally than the proximal-most electrode. In alternative embodiments, however, the reflector can extend distally to the proximal-most electrode in some locations around the membrane. For example, the distal edge of the reflector can be curved rather than straight, and depending on the electrode layout on the membrane, some portions of the reflector may extend distally relative to the proximal-most electrode. If the membrane in its inflated configuration can be divided in half between the distal most location and proximal most location defining a distal portion and proximal portion, the reflector is disposed at least on the proximal portion. In the embodiment shown in FIGS. 1A-1C, the reflector is disposed only on the proximal portion.

One aspect of the disclosure is an expandable member that includes a diffuse reflector but does not include any ablation element. For example, medical devices that include an inflatable member and at least one camera and at least one light source therein can benefit from a diffuse reflector even if the device is not used for ablation procedures.

While the reflector herein is described as being a diffuse reflector, there may be some uses in which a reflector that reflects light in a specular manner may be beneficial. Alternatively, a reflector can have portions that reflect light in a diffuse manner and portions that reflect light in a specular manner.

Figure 4:
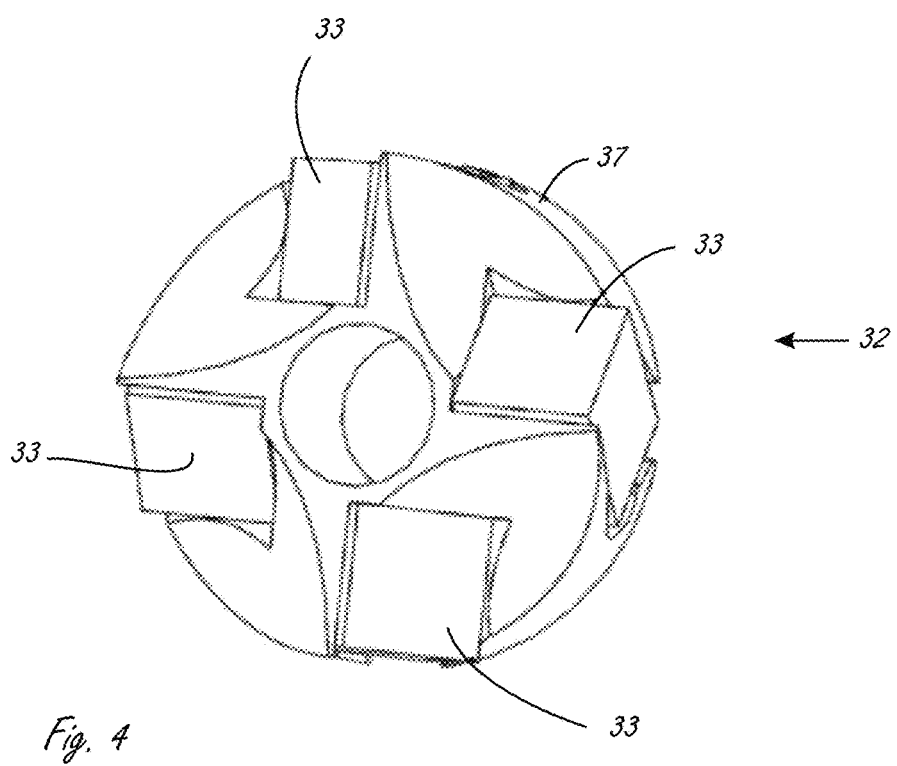
FIG. 4 illustrates a camera assembly.

FIG. 4 shows an exemplary camera assembly 32 that includes four cameras 33, which are disposed within camera hub 37 at an angle relative to the longitudinal axis of the catheter. Camera hub 37 is secured to guide wire shaft 54, and includes lumen 39 configured to receive guide wire shaft 54 therein.

Figure 5:
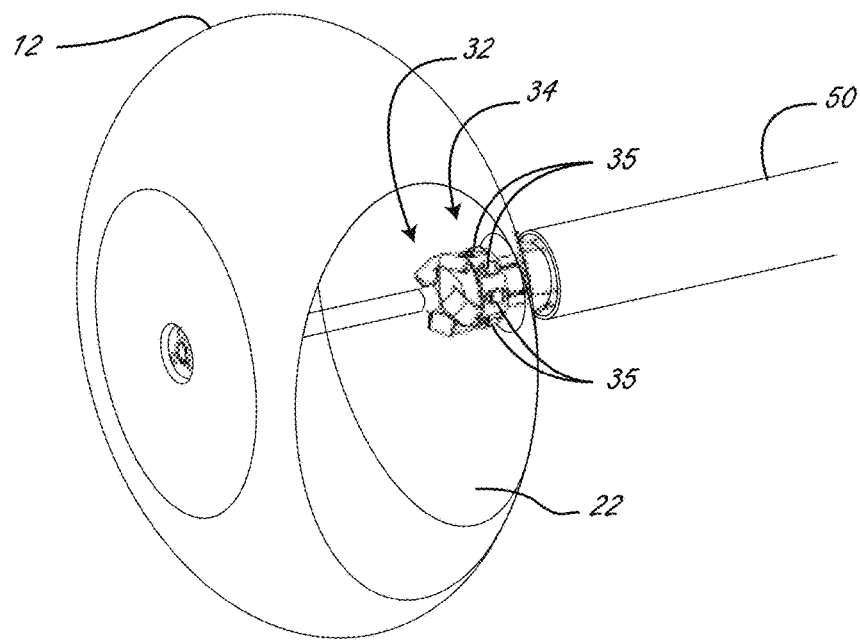
FIG. 5 is a perspective view of a distal end of an ablation catheter, with a cutaway of an expandable member.
Figure 6:
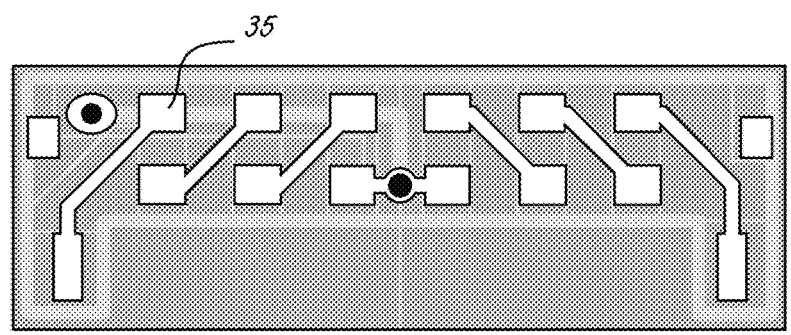
FIG. 6 is an exemplary flat view of the LED flex circuit.

FIG. 5 is another perspective view of expandable member 10 with a cutaway of the membrane. FIG. 6 is an exemplary flat view of the LED flex circuit, including the LEDs, that is wrapped around the illumination hub proximal to the cameras.

As set forth above, light is reflected from the diffuse reflector to provide illumination in the field of the view of the at least one camera. The field of view of the camera can include the view of an electrode secured to the membrane. As set forth herein, the electrodes can be highly reflective, such as if they are comprised of silver. Reflective electrodes causes light incident upon the electrodes to reflect into the camera field of view, which can cause the electrodes to appear as bright spots on the display, possibly interfering with viewing the procedure. It can thus be beneficial to include in the catheter a reflection adjuster that is adapted to reduce specular reflection of light from at least one of the plurality of ablation electrodes into the field of view of an imaging member.

In some embodiments the reflection adjuster is a light absorber. The light absorber can be positioned between the bottom of the electrodes and the membrane. In some embodiments the light absorber is a black adhesive that adheres portions of the electrode to the membrane, as well as acts as a light absorber.

In some embodiments the reflection adjuster is an anti-reflective coating. Exemplary anti-reflective coatings include, for example without limitation, a deposited thin layer of TiO2, MgF2, and "moth eye" structures comprised of nanoparticles approximately 200 nm in diameter spaced 300 nm range, random microstructure secured to or created on the interior surface of the membrane that is adapted to reduce reflection. The anti-reflective coating can be adhered to only a portion of the membrane, such as the portion where the electrodes are disposed. For example, an anti-reflective coating could be applied to only the distal portion of the inner membrane.

A reflection adjuster will reduce the amount of reflection from the bottom of the electrodes, creating a clearer image of the membrane and electrodes from within the membrane.

When the images or video provided by the at least camera are displayed on the display, it can be helpful to be able to visually identify the electrodes on the display. For example, a user interface can be used to control delivery parameters for any of the electrodes, and enabling the physician to easily determine and confirm that a given electrode on the video is a particular electrode on the user interface simplifies the procedures and ensures that the correct electrodes are being activated and used as intended.

In some embodiments the catheter includes an electrode identifier associated with at least one of the plurality of electrodes, and is some embodiments the catheter includes an electrode identifier with each of the plurality of electrodes. The electrode identifier need not be unique to each of the electrode, but in some embodiments it is unique to each electrode. The electrode identifier is visually identifiable and allows an individual to visually associate the identifier with an electrode.

In some embodiments the electrode identifier is an alphanumeric characters disposed on or near each of the electrodes. An example of this type of identifier is described and shown below. For example, an alphanumeric character can be printed on the back of an electrode, or the back of a portion of the flex circuit that is associated with an electrode. An alphanumeric character can also be printed on the membrane near the electrode so that the identifier can be easily associated with a particular electrode.

In some embodiments the electrode identifiers are colors associated with one or more of the electrodes. For example, the electrodes can be color-coded so that a user can visually identify each of the electrodes. In some embodiments a group of electrodes can have a particular color, such as all of the electrodes connected to the same flex circuit are all one color. An additional example of an electrode identifier is the shape of the electrode so that the electrode or group of electrodes can be visually identified based on their shape. For example, groups of electrodes can be circular, oval, hexagonal, rectangular, square, etc. Each electrode could have a unique shape to it as well.

An example of electrode identifiers is described below in the context of overlaying field of view images from a plurality of cameras.

Figure 10:
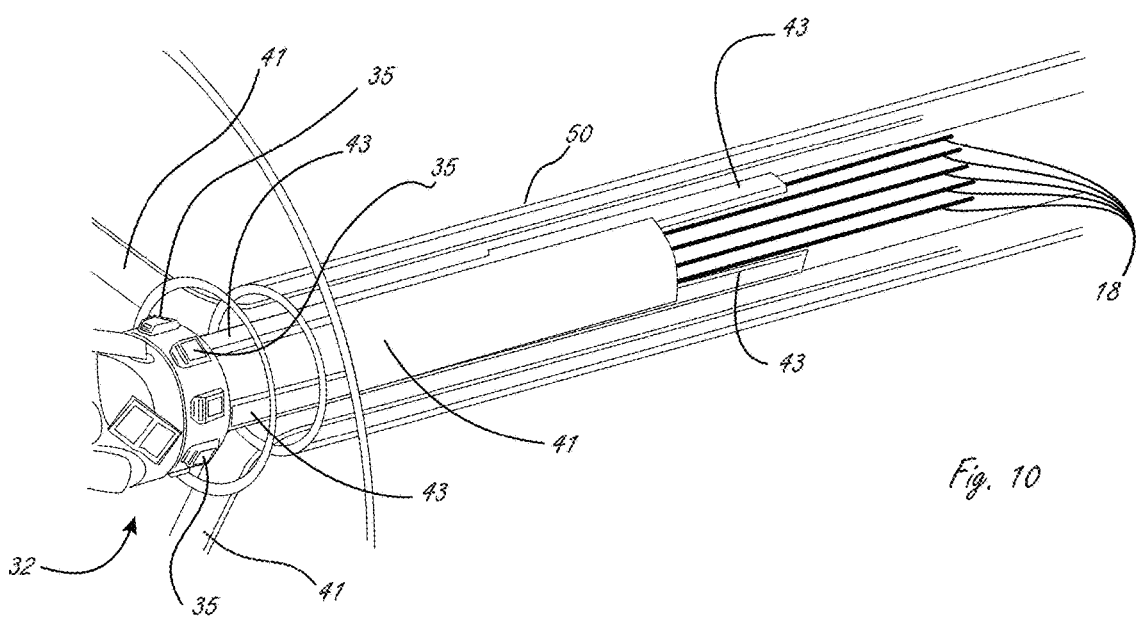
FIG. 10 illustrates each of the three flex circuit tails terminating in terminations extending proximally from the distal end of the balloon and extending proximally within an outer shaft and secured to the outer surface of the proximal end of the balloon and irrigation shaft.

FIG. 10 illustrates each of the three flex circuit tails terminating in terminations 41 (one for each flex circuit) extending proximally from the distal end of the balloon and extending proximally within outer shaft 51 and secured to the outer surface of the proximal end of the balloon and irrigation shaft 55. The proximal aspect of the configuration can also be seen in FIG. 2B. In FIG. 10, six conductive wires 18 can be seen extending proximally from one of the terminations 41, each one of which is in electrical communication with one of the six electrodes in that particular flex circuit. The six wires 18 extend the length of the catheter and are in communication with the RF generator. In an alternate embodiment, not shown, the six conductive traces 15 extend the length of the catheter and are in communication with the RF generator. Camera flex circuit 43 for the visualization system is also shown in FIG. 10, extending proximally from the visualization system in the catheter.

Exemplary materials for the membrane and flex circuit materials can be found in U.S. Pat. No. 8,295,902, issued Oct. 23, 2012; U.S. Pub. No. 2012/0071870, published Mar. 22, 2012. Additional examples of membrane material include PET, Polyurethane, etc. Exemplary materials for the reflector include metalized paints, silicone or urethane resin filled with nonconductive white pigment such as TiO or BaO or BaSo4, preferably non-conductive. Exemplary materials for the electrodes include silver filled silicone or urethane. Exemplary materials for the conductive traces are conductive metals including copper or other such conductive materials. The insulation layers can be known dielectric materials. Exemplary materials for the substrate include Kapton.

As described herein ablation catheters can include ablation and mapping electrodes secured to the exterior of the membrane. In such embodiments the area of tissue mapped is limited to the area of contact defined by the inflatable structure. The rotors being mapped can, however, be larger than the contact area of the inflatable structure, making it more difficult and time consuming to properly map the atrial chamber for rotors. In some embodiments the ablation catheter includes an inflatable membrane, and is also adapted to increase the area that can be mapped to an area that is greater than that defined by the expandable membrane contact surface.

In some of these embodiments mapping arms when appropriately stiff may provide a way to limit the accidental entry of the ablation elements into the pulmonary arteries thereby minimizing the risk of accidental ablation of the artery wall and consequent risk of subsequent stenosis.

In some embodiments a mapping structure on which at least one mapping electrode is disposed is carried outside of the balloon and collapsed between the wall of the delivery catheter and the outside of the ablation catheter. The mapping structure can be secured to the exterior of the ablation catheter. In some embodiments the one or more mapping structures can be deformable splines, the use of which has been described in the cardiac ablation space. For example, the mapping structures can be made of nitinol and are adapted to deform. The mapping structure can thus expand on release from the delivery catheter and can be collapsed to a collapsed delivery configuration when the delivery catheter is advanced distally relative the ablation catheter In other embodiments a mapping electrode structure is adapted to be delivered through the guide wire lumen of the ablation catheters herein.

Figures 11A, 11B:
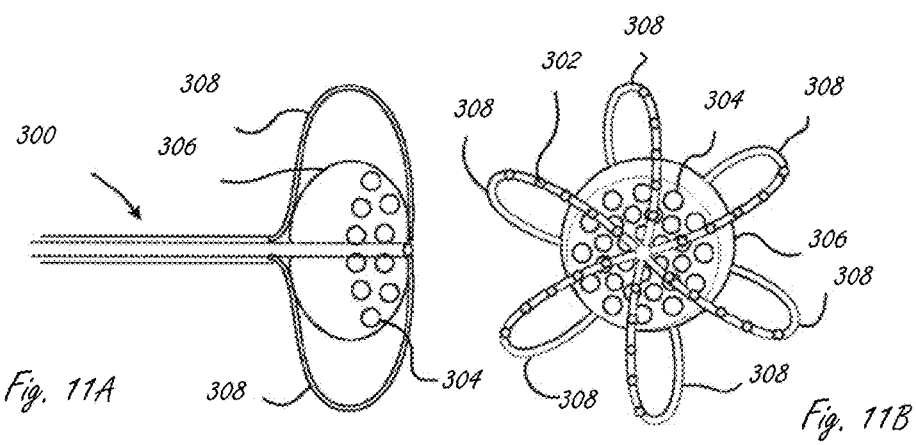
FIGS. 11A-11B, 12A-12B, 13, 14A-14B, 15 and 16 illustrate exemplary ablation catheter adapted with mapping structures or adapted to be used with mapping structures.
Figures 12A, 12B:
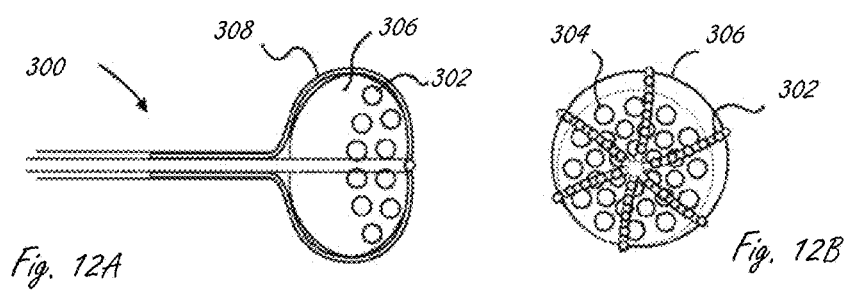

FIGS. 11A and 11B depict an exemplary ablation catheter 300 that includes an array of mapping electrodes 302 (only one is labeled for clarity) carried on the surface of a plurality of reconfigurable mapping arms 308. FIG. 11A is a side view and FIG. 11B is a distal view. Arms 308 together have a "basket" configuration and are disposed outside of the inflated membrane 306. In FIGS. 11A and 11B arms 308 are in their expanded configurations, after being released from within the delivery catheter. Arms 308 are collapsed into the space between the delivery catheter and the ablation catheter 300 during delivery and retrieval, and are adapted to self-expand on release by retraction of the delivery catheter or delivery past the distal end of the delivery catheter. Six arms 408 are shown, each with a plurality of electrodes 302, but more or fewer arms of the basket can be included. The arms can all be secured to the same mapping basket hub (or made from a single piece of material), or they can be secured independently to the ablation catheter. FIGS. 11A and 11B show catheter 300 with arms 308 in retracted positions in with proximal ends of arms 308 are retracted and positioned between the delivery catheter and the ablation catheter. Arms 308 are closer to the surface of expanded membrane 306 than in the expanded configurations shown in FIGS. 11A and 11B.

Figure 13:
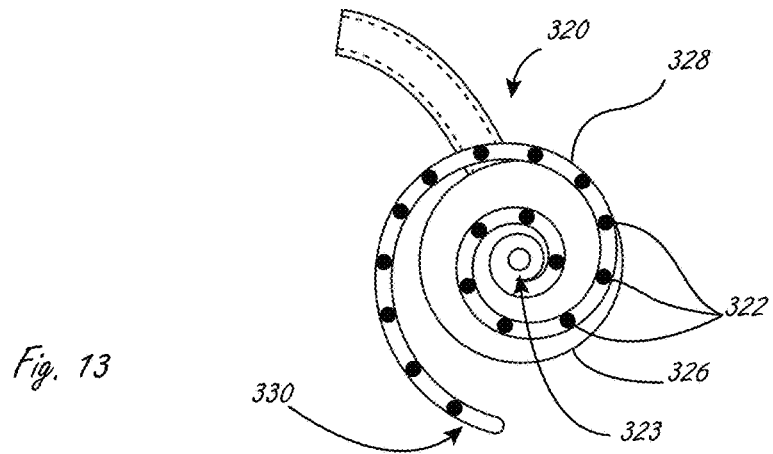

FIG. 13 is a distal view of a distal end of an exemplary ablation catheter 320. In this embodiment the ablation catheter includes an alternative spiral structure 328 that carries a plurality of mapping electrodes 322 (only three are labeled). The spiral mapping structure can be adapted to be delivered through the guidewire lumen 323, or it can be adapted to be expanded from between the delivery catheter and ablation catheter shaft, similar to the embodiment in FIGS. 11A and 11B. In the embodiment in FIG. 13 in which the spiral structure is adapted to be delivered via a guidewire lumen, the spiral, in a side view, can be in a single plane, or the spiral can have a conical configuration that is adapted to be deformed into a single plane when the spiral is pushed distally into contact with tissue. Ablation electrodes are not labeled on the ablation balloon for clarity on FIGS. 13-17.

Figures 14A, 14B:
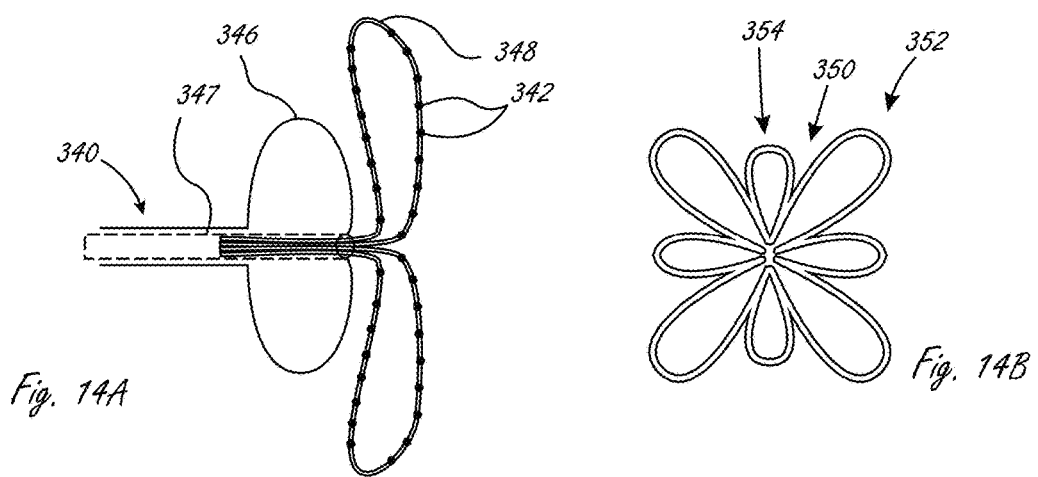

FIG. 14A is a simplified side view illustrating an alternative ablation catheter 340 with a dedicated mapping structure 348 with a plurality of mapping electrodes 342 (only two are labeled) thereon. In this embodiment the two mapping arms 348 have expanded loop configurations as shown and are adapted to be delivered through guidewire lumen 347 as shown. There may be more or fewer than two arms. FIG. 14B is a distal view of an alternative embodiment in which the mapping structure 350 includes a plurality of loops in their expanded configurations. In this embodiment at least one loop 352 has an expanded "height" (a distance measured from the longitudinal axis of the catheter along a line perpendicular to the axis) greater than a height of a second loop 354. In particular, there are four arms 352 with a first height greater than a height of four other arms 354. There can any number of loops of varying height dimension.

Figure 15:
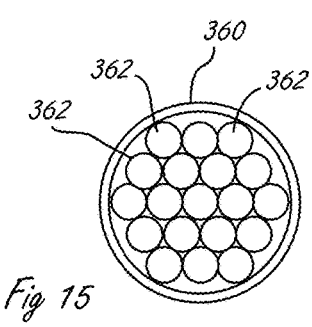

FIG. 15 illustrates an exemplary configuration of mapping arms and electrodes 362 in collapsed configurations within guidewire lumen 360, and is merely illustrative to show how a plurality of arms can be disposed within a guidewire lumen. More or fewer arms can be disposed therein.

Figure 16:
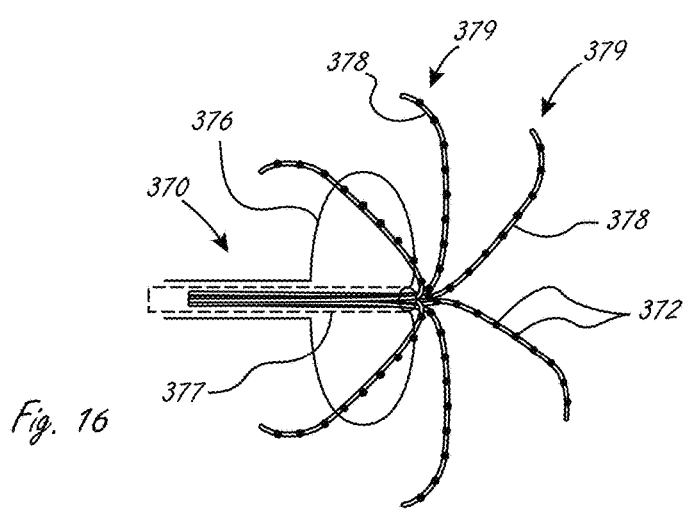

FIG. 16 shows a simplified side view of an exemplary ablation catheter 370 in which the mapping arms 378 terminate at their respective distal ends 379. That is, each arm has a free end. Catheter 370 includes balloon 376, guidewire lumen 377, mapping electrodes 372 on arms 378, similar to other embodiments herein. Any of the described mapping arms may comprise a stiffening member such as NiTi wire such that on release the mapping member takes on a predetermined shape.

Any of the mapping arms that are delivered through the guidewire lumen can alternatively be configured for delivery in the space between the ablation catheter and the delivery catheter, and vice versa.

In yet other embodiments the mapping arms may be woven into a conical braid or braid structure which increases in diameter as it extends distally.

In use, the visualization system allows for real-time visualization of the procedure with a view by one or more cameras disposed within the balloon. The visualization allows for the entire procedure to be visualized, allowing physicians to assess the degree of tissue contact, and see the electrodes, tissue, and lesion formation as it occurs. For clarity, FIG. 29 illustrates only one of the four fields of view for one of the four cameras in the camera assembly. FIG. 30 illustrates the four fields of view from the four cameras, each overlaid with at least one other field of view, to give the physician a 360 degree view (with the longitudinal axis of the catheter as the reference) of the treatment area. While there is a blind spot shown in the center of the four images, different lensing systems than those used in the current embodiments can allow for elimination of that spot. Since there are electrodes disposed around the entire catheter, the 360 degree view allows the physician to visualize an entire lesion that utilizes electrodes disposed around the catheter. The visualization of the entire procedure including lesion formation at any of the electrode locations is immensely helpful to the physician.

The description herein of overlaying camera fields of view is related to the disclosure in U.S. Pub. No. 2012/0071870, in particular FIGS. 38H-38R, and the textual descriptions thereof. One aspect of this disclosure is an exemplary method of generating a panoramic image display using images from a plurality of cameras attached to an endoscopic catheter. In some embodiments a plurality of images captured from a plurality of cameras are overlayed with at least one other image to create the panoramic image around the longitudinal axis of the ablation catheter. Two or more cameras can image various sections of the expandable member (from within the expandable member) and the anatomy, and the geometric relationships between the cameras are either known a priori (by design or measurement), or can be estimated from the images themselves using common anatomical features of the balloon as landmarks.

In general, for each camera, a mapping function that maps a pixel into a virtual unwrapped display screen, e.g. a dome-shaped screen, surrounding the cameras is computed. The images are then projected back to this virtual display screen using inverse projection, i.e., using cameras as projectors. Data in overlapping regions are combined using compositing including blending or some other means.

FIG. 17 is a side view of a distal portion of an exemplary visualization catheter. FIG. 17 shows the geometry of the distal portion, which includes four cameras attached to the distal end of the central shaft of the catheter, surrounded by a membrane filled with saline. Each camera is imaging a section of the closed membrane from within the membrane. The conical shape shown in FIG. 17 represents the field of view of one of the plurality of cameras. In this embodiment, while not shown in FIG. 17, a plurality of radio frequency electrodes are secured to the exterior of the membrane. When the distal portion is positioned inside a cardiac chamber such as the left atrium, the cameras are able to visualize blood or tissue outside the balloon as well as the inner surface of the balloon. This provides a way to verify that the electrodes are in contact with tissue prior to starting the ablation and the balloon is located properly relative to anatomical landmarks such as a pulmonary vein.

FIGS. 18A-18D show the orientations of the axes of the four cameras in relationship to the longitudinal axis of the catheter shaft. Arrows AP, BQ, CR and DS shown in FIG. 18C represent the axes of the respective cameras. OM is the longitudinal axis of the catheter shaft. The parameter "c" is the shortest distance between the axis of the catheter shaft OM and an axis of a camera (see FIG. 18A). The camera axis is also at an angle φ relative to the axis of the catheter shaft OM (see FIG. 18B). The distal surface of the membrane can be modeled as an elliptical solid of revolution, as shown in the side geometrical view of FIG. 18D. Parameters a and b define the ellipsoid. The equator of the ellipsoid, as labeled in FIG. 18D, is at a distance "d" from the point "O" shown in FIG. 18D. The imaging plane of the camera with the axis CR is at a distance e from C, as shown in FIG. 18D.

Figure 19:
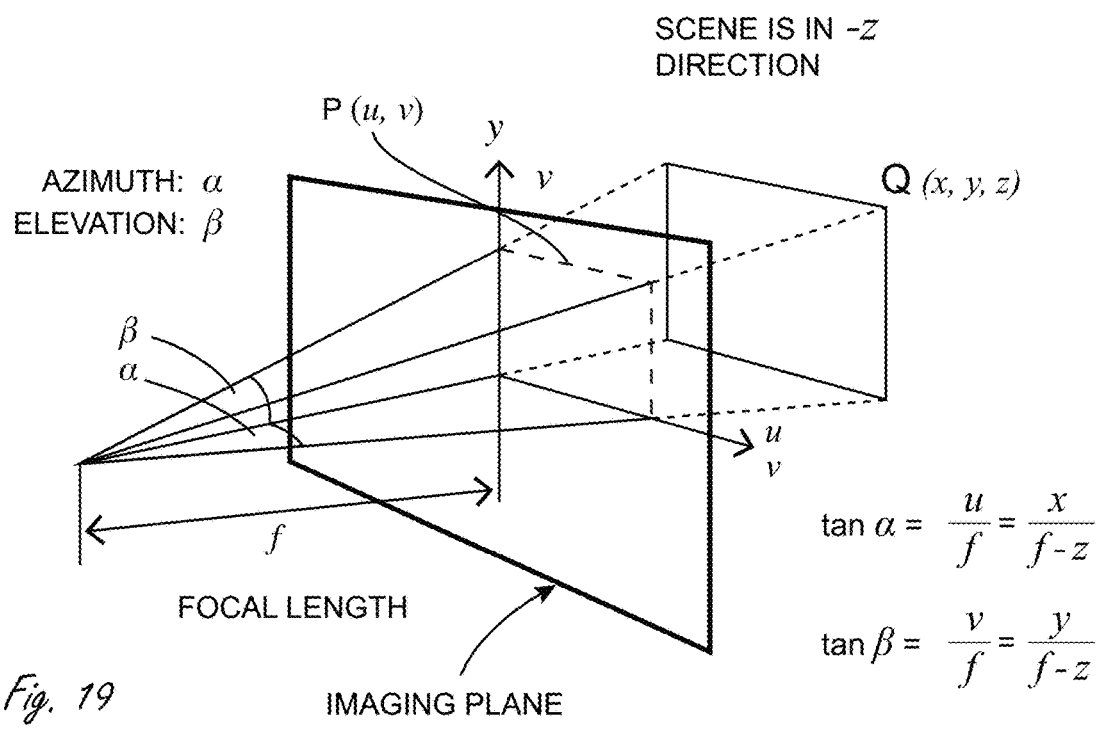
FIG. 19 shows the geometry of one of the four cameras, and all four have the same geometry.

FIG. 19 shows the geometry of one of the four cameras field of view, and all four have the same geometry. A pixel in the imaging plane, P(u, v), is related to a point Q(x, y, z) in space by equations (1) and (2), where f is the focal length of the camera.

$$\frac{u}{f} = \frac{x}{f-z} \quad (1)$$

and $$\frac{v}{f} = \frac{y}{f-z} \quad (2)$$

Figure 20:
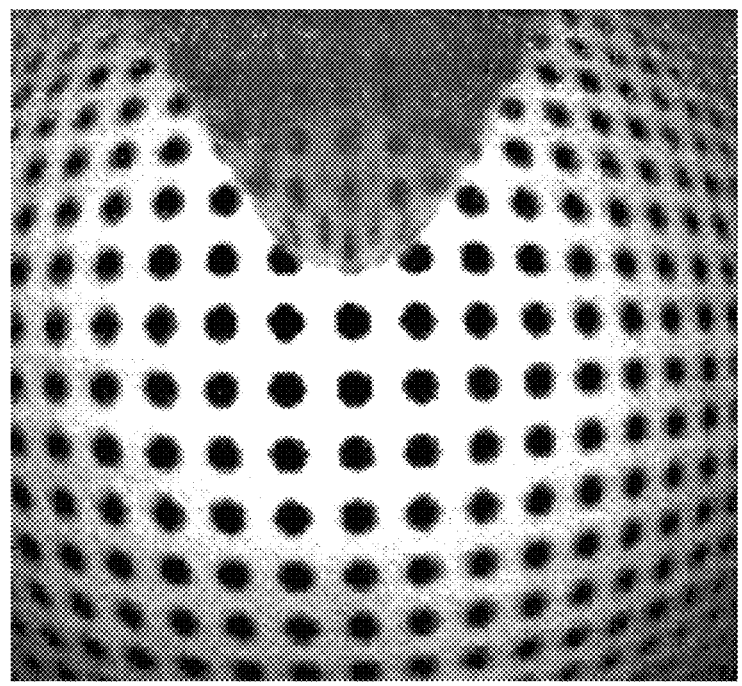
FIG. 20 shows a picture of a regular grid pattern target taken by a representative camera.

Furthermore, the image captured by the camera can have lens barrel aberration. FIG. 20 shows a picture of a regular grid pattern target taken by a representative camera. As can be seen, barrel aberration causes the grid points farther away from center 390 to appear smaller and compressed to each other.

The mapping function that maps the original pixel coordinates, P(u, v), to a distorted pixel coordinate system due to barrel aberration, $\tilde{P}(\tilde{u}, \tilde{v})$, can be determined by using the grid target:

$$\begin{bmatrix} \tilde{u} \\ \tilde{v} \end{bmatrix} = \begin{bmatrix} F(u) \\ G(v) \end{bmatrix} \quad (3)$$

Figure 21A:
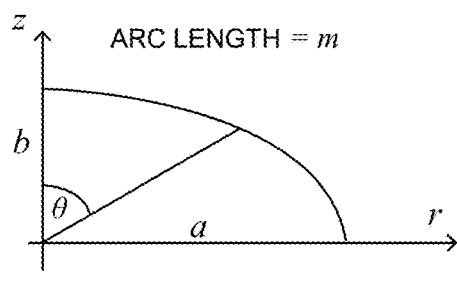
FIGS. 21A, 21B and 21C show parameterization that can be used to unwrap the 3D surface of the ellipsoidal balloon into a 2D plane.
Figure 21B:
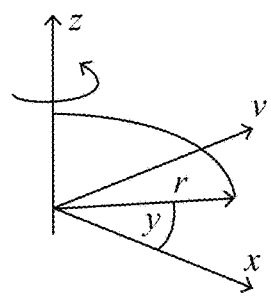
Figure 21C:
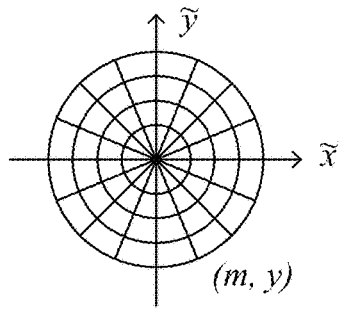

The 3D surface of the ellipsoidal balloon can be unwrapped into a 2D plane using the parameterization shown in FIGS. 21A-21C. In FIG. 21A, the parameters of a and b describe the balloon as an elliptical solid of revolution. The parameter m corresponds to the arc length along the balloon surface, starting from the zenith. In FIG. 21B the rotation angle γ describes the azimuthal angle of the solid of revolution. In FIG. 21C, the unwrapped balloon surface is defined by the parameters (m, γ) in polar coordinates or ($\tilde{x}$, $\tilde{y}$) in rectilinear coordinates.

A point on the balloon surface can be: (x, y, z). A planar unwrapped image can be constructed from the ellipsoidal balloon geometry by unwrapping the balloon surface as follows:

$$\begin{bmatrix} x \\ y \\ z \end{bmatrix} = \begin{bmatrix} a \sin \theta \cos \gamma \\ a \sin \theta \sin \gamma \\ b \cos \gamma \end{bmatrix} \quad (4)$$

Where:

$$\theta = g(m) \quad (5)$$

and g(m) is the well-known "Complete Elliptic Integral of the Second Kind." The unwrapped 2D surface is defined by the polar coordinates: (m, γ) or in rectilinear coordinates, ($\tilde{x}$, $\tilde{y}$), where:

$$\begin{bmatrix} \tilde{x} \\ \tilde{y} \end{bmatrix} = \begin{bmatrix} m \cos \gamma \\ m \sin \gamma \end{bmatrix} \quad (6)$$

In summary, the parameters in Table 1 (below) describe the camera geometry of this multi-camera system.

TABLE 1

| | Parameter | Description |
|---|---|---|
| 1 | a | Ellipsoidal balloon geometry |
| 2 | b | |
| 3 | c | Distance offsets |
| 4 | d | |
| 5 | e | |
| 6 | f | Focal length |
| 7 | φ | Camera angulation |
| 8 | F | Barrel aberration mapping function |
| | G | |

Using the parameters of Table 1, the ($\tilde{x}$, $\tilde{y}$) coordinates of the point on the unwrapped balloon corresponding to each pixel in an image produced by a given camera can be computed. Then the intensity of that pixel can be painted on the unwrapped balloon surface. If more than one camera projects data on to the same location on the unwrapped balloon surface, the data can be combined using any number of exemplary ways, such as blending, maximum value, adaptive blending, alpha blending, weighted averaging, etc. These techniques fall into the general category of "Compositing" as described in Foley et al., "Computer Graphics Principles and Practice", 1990, Addison Wesley, $2^{nd}$ Edition. ISBN 0-201-12110-7. In the overlapping areas of images from two or more cameras, the underlying anatomical structure may be slightly misaligned even after following the above steps to grossly align the image due to inaccuracies in the geometric model. In this case, a given tissue structure may appear twice in the overlapping area, similar to double vision. To address this problem, images can be locally warped by using feature tracking. See U.S. Pat. No. 6,659,953, issued Dec. 9, 2003 to Sumanaweera et al., titled "morphing diagnostic ultrasound images for perfusion assessment," for a description of an exemplary local warping technique.

Figure 22:
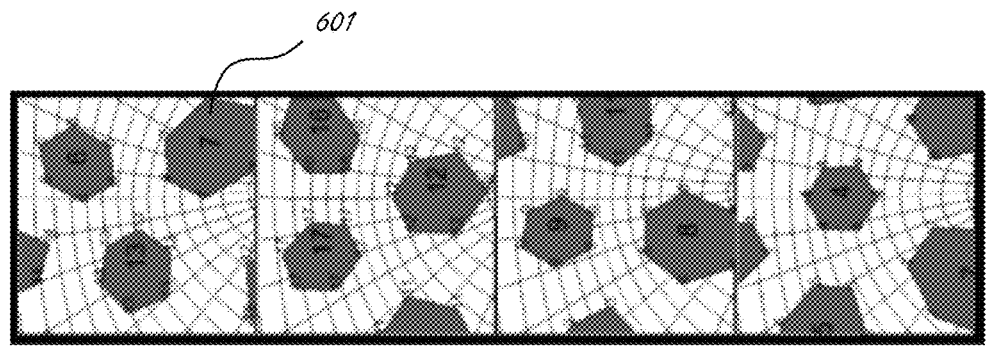
FIG. 22 shows a set of four camera images simulated using a known pattern, in this case, ablation electrodes painted on the membrane.

FIG. 22 shows a set of four camera images simulated using a known pattern, in this case, ablation electrodes 601 painted on the membrane. Electrodes 601 can be in the pattern of the eighteen electrodes shown in FIGS. 1A-1D. Electrodes 601 also have an identifier associated with them, in this case a unique alphanumeric character.

Figure 23:
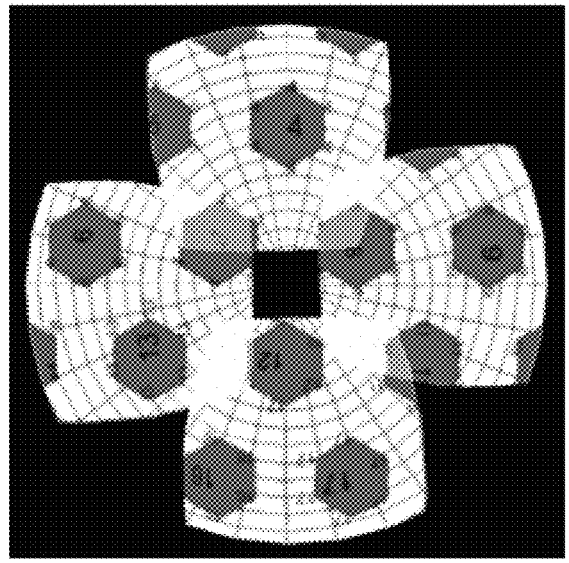
FIG. 23 shows the panoramic image generated by projecting the images from FIG. 22 back onto the unwrapped balloon surface using the methods described above.
Figure 25:
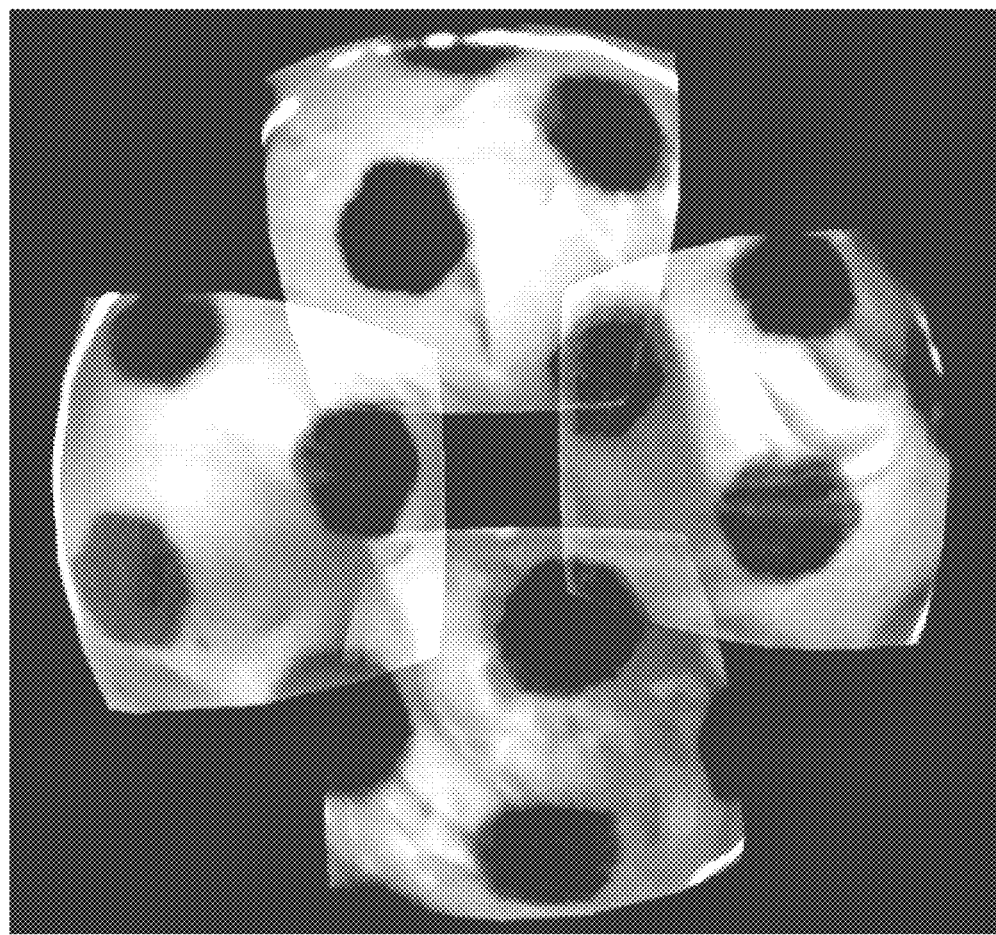
FIG. 25 shows tissue images acquired by four cameras using the methods described herein.
Figure 26:
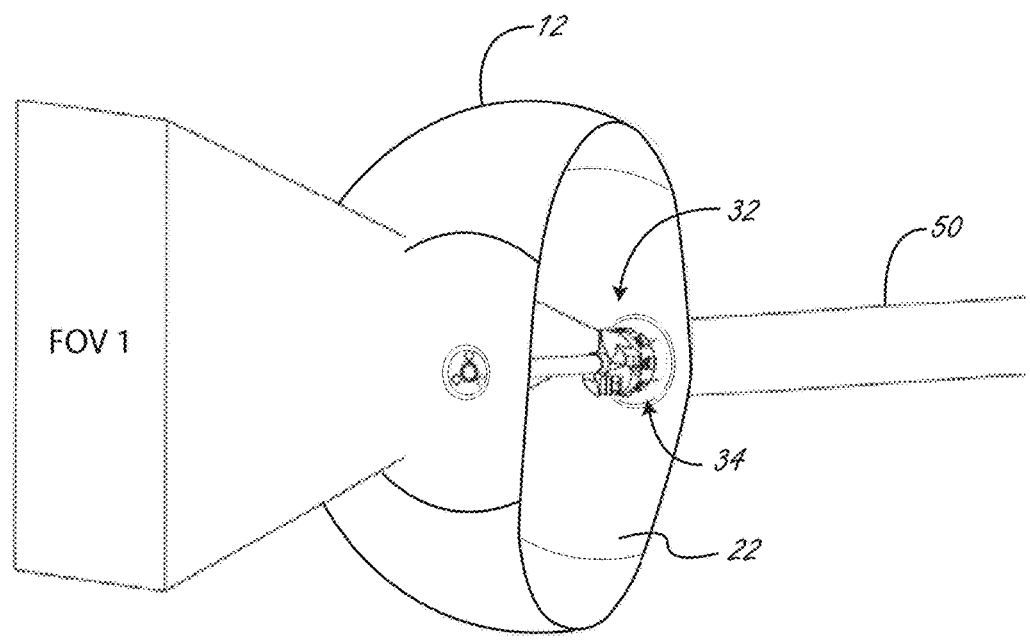
FIG. 26 illustrates only one of the four fields of view for one of the four cameras in the camera assembly.
Figure 27:
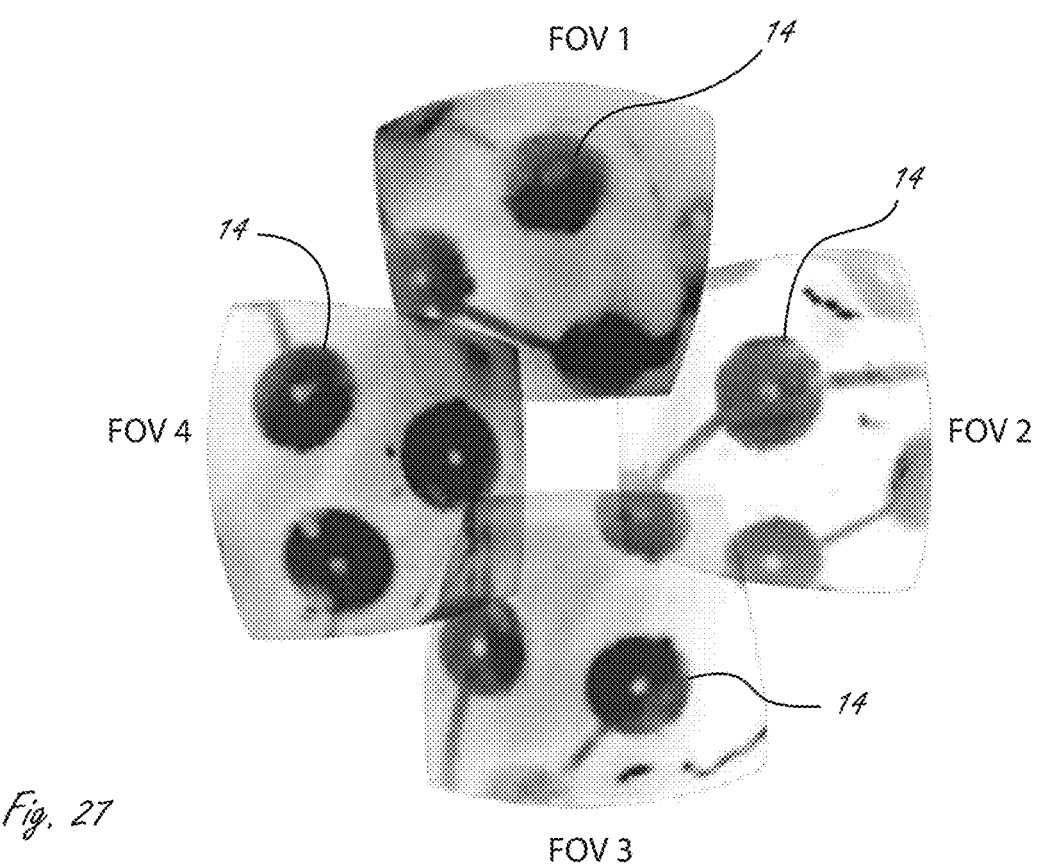
FIG. 27 illustrates the four fields of view from the four cameras, each overlaid with at least one other field of view, to give the physician a 360 degree view.

FIG. 23 shows the panoramic image generated by projecting the images from FIG. 22 back onto the unwrapped balloon surface using the methods described above. FIG. 25 also illustrates exemplary electrode identifiers in the form of numbers printed on each electrode to enable visual identification of each of the electrodes. FIG. 25 also illustrates how the collected images comprise common regions to images that are positioned adjacent to them, and that the common regions are overlapped to create the panoramic image.

Figure 24:
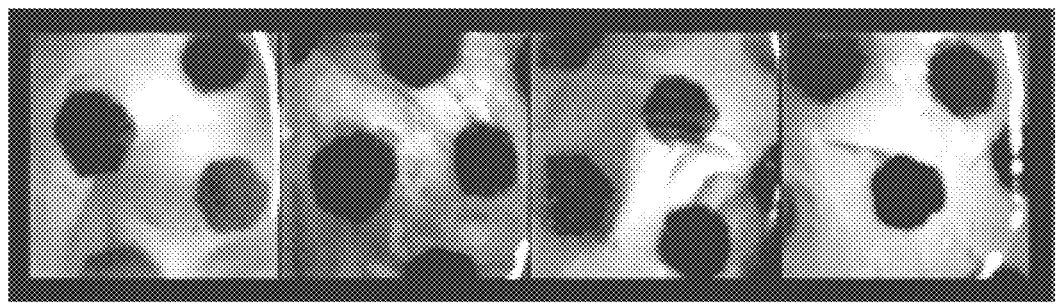
In FIG. 24 the panoramic image is generated by projecting the component images back onto the unwrapped balloon surface.

In FIG. 24 the panoramic image is generated by projecting the component images back onto the unwrapped balloon surface, but the electrodes 370 do not have electrode identifiers associated with them. FIG. 25 shows tissue images acquired by four cameras using the methods described above. FIG. 25 shows the panoramic image generated by projecting these images back onto the unwrapped balloon using the present invention.

The exemplary method above acquires an image from each of a plurality of cameras, and combines the images to produce a panoramic image. As set forth above, the images from each camera can be deformed using a geometric transformation. The deforming can comprise information associated with the known geometric relationship between the cameras. The deforming procedure can comprise geometric transformations generated using compositing in the overlapping areas of the images. The procedure can comprise the use of weighted averaging. The procedure comprises alpha blending. The deforming procedure can comprise geometric transformations generated using feature tracking in the overlapping areas of the images. The characterization of the geometric relationship between the cameras can comprise the use of experimentally determined optical targets. The geometric relationship can be determined analytically by geometrically modeling the cameras, the fixture containing the cameras and the balloon. The geometric transformation can include geometric transformations that map the balloon onto a planar surface while maintaining the distance between any arbitrary set of points on the 3D surface.

In an exemplary method of use, the catheter is used to ablate cardiac tissue in the treatment of a cardiac arrhythmia. The catheter is advanced into the left atrium using known access procedures including guide wire and guide catheter techniques. Inflation/irrigation fluid is then pumped from a fluid source down inflation/irrigation lumen 52 to inflate the balloon to the configuration shown in FIGS. 1A-1C within the left atrium. The camera can be activated at any time during the procedure, but generally before inflation so the physician can see if there are any problems with the inflation. At this point the balloon is surrounded by blood, which can be seen. The catheter is advanced distally towards the atrial wall, and as the balloon contacts tissue the blood will be displaced, providing a clear view of the tissue. The physician can then determine if the balloon needs to be moved depending on the desired treatment tissue or desired area to map. An advantage of the visualization system in the devices herein is that the physician can easily see, simply by viewing a display showing the camera fields of view, when the balloon is properly positioned. This also simplifies the system in that an analysis of reflected energy need not be performed, as in the case in some previous attempts at cardiac ablation.

Figure 32:
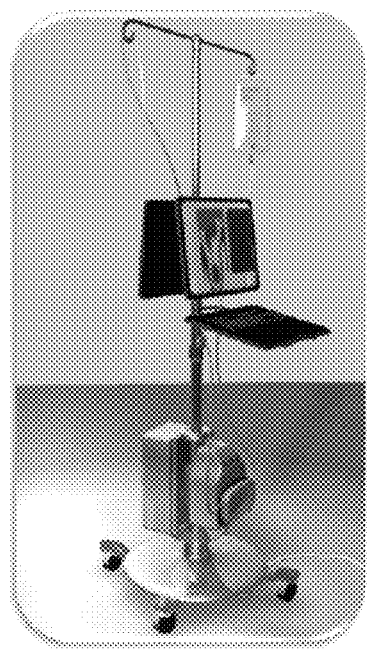
Figure 33:
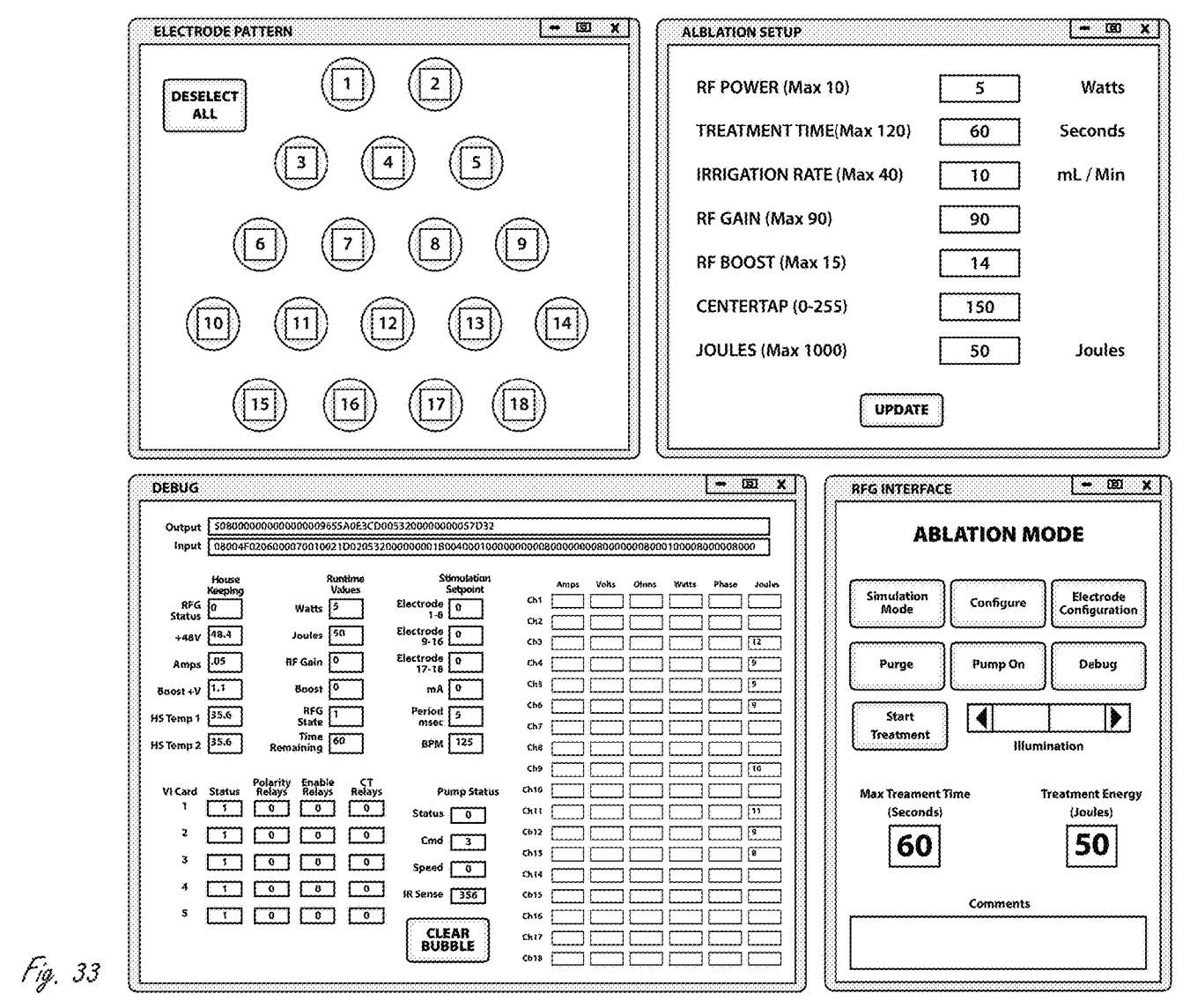

Once it has been determined, depending on the visualization information such as proper placement around a pulmonary vein or mapping electrical information, that the balloon has been properly positioned at the treatment site, an external console, generally shown in FIGS. 32 and 33, is used to activate certain electrodes and control the energy delivery parameters of the procedure. An RF generator generates the RF energy and it is delivered to the electrodes. An exemplary schematic of the electrical aspect of the embodiment shown herein is shown in FIG. 33. It is understood that eighteen channels are included while only three are shown. Alternate embodiments, not shown, may comprise more or less channels. As shown in FIG. 33, the mapping capabilities of the system are shown to the right of the electrode. Each electrode can be used in monopolar or bipolar mode, and impedance and voltage can be measured with each electrode.

The generator is configured such that electrodes can be used to map tissue, ablate tissue, and stimulate tissue, as desired. Ablation of cardiac tissue to treat aberrant signals is described generally herein and known. The generator is also configured, however, to generate and deliver electrical tissue stimulation signals to the electrodes so that the electrodes stimulate the cardiac tissue. The schematic in FIG. 30 illustrates that each electrode can be selected for either ablation or stimulation, while mapping from each electrode occurs continuously. The mapping portion includes filters configured to filter out ablation bandwidths, and other non-essential bandwidths that may be delivered or otherwise present so that mapping can occur continuously. The disclosure herein thus includes a generator configured such that each electrode can be used to both map and ablate tissue at the same time, or stimulate and ablate tissue at the same time. The system is also configured such that ablation, stimulation, and mapping can all be occurring at the same time, although the stimulation and ablation would not be occurring at any given time from the same electrode. These processes in addition can be performed sequentially.

Stimulation of the cardiac tissue can be done for a number of reasons. In an exemplary embodiment stimulation of tissue can be performed during a diagnostics procedure to make sure the electrodes are working. For example, RF energy can be delivered to a first electrode and sensed with another electrode, thereby transferring energy between pairs of electrodes to make sure the pair of electrodes is working. In this exemplary use, the stimulating energy could be delivered before the balloon makes contact with tissue or after it makes contact with tissue, as blood generally has low enough impedance so as not to prevent the diagnostic test. In an alternative embodiment cardiac tissue can be stimulated while tissue is being ablated with other electrodes. For example without limitation, three electrodes could be used to deliver ablation energy to create a lesion between the three electrodes (e.g., a linear ablation), while an electrode on one side of the lesion could be used to deliver stimulating energy to an electrode on another side of the lesion to determine if the tissue is effectively ablated. Exemplary tissue stimulation delivery signal capabilities include currents of 0 to 20 ma, pulse widths of 0 to 100 ms, repetition rates of up to 300 bpm. More preferably 0 to 10 ma, 0 to 10 ms, and up to 180 bpm. Stimulating cardiac tissue in these ways is different than mapping in that mapping measures impedance, while stimulation delivers energy configured to stimulate the cardiac tissue. The disclosure herein therefore includes methods of stimulating cardiac tissue during an ablation procedure, including before the actual ablation, while ablating, or after the ablation has occurred.

Figure 28A:
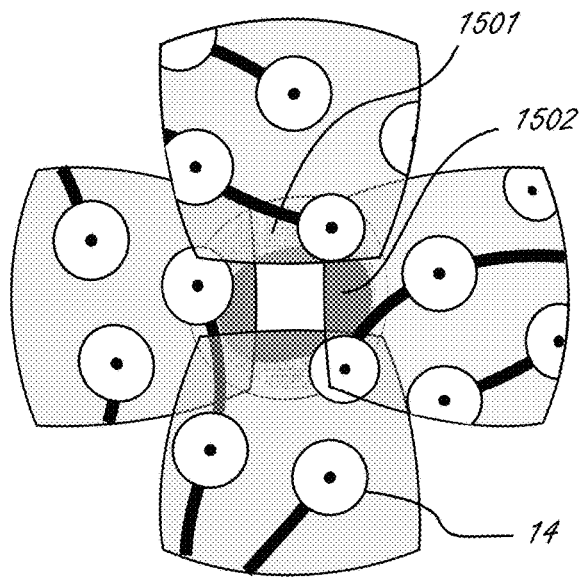
FIGS. 28A, 28B and 28C illustrate an exemplary method of ablating cardiac tissue.
Figure 28B:
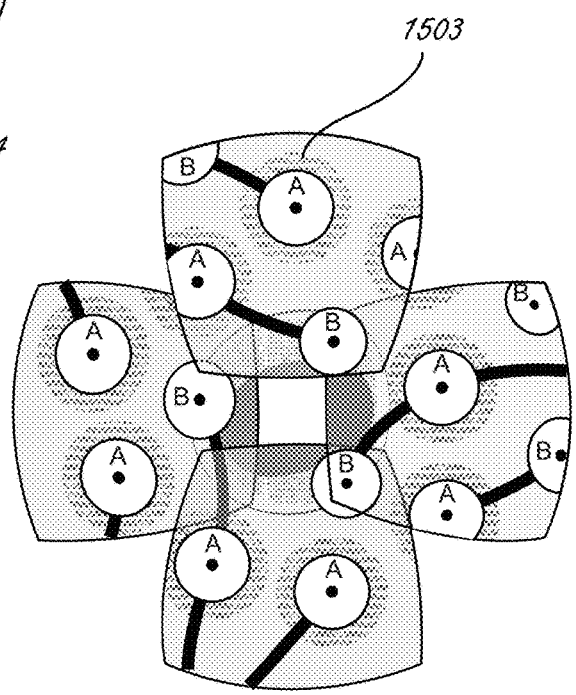
Figure 28C:
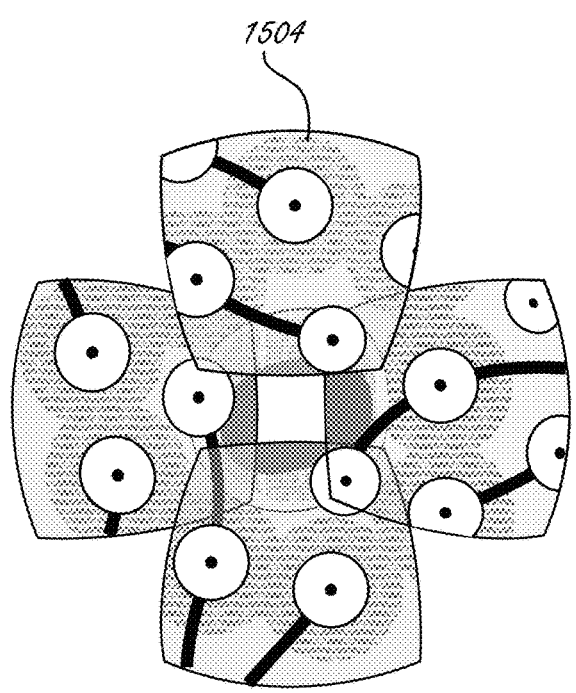

FIGS. 28A-28C illustrate an exemplary method of ablating atrial tissue around a pulmonary vein ostia to isolate the pulmonary vein, and show it from the view generated by the four fields of view from the camera. FIGS. 28A-28C are meant to be the view the physician would see when using the system. Again, the blind spot in the middle can be removed depending on the camera assembly and arrangement of cameras therein. In FIG. 28A, the balloon has been advanced into contact with atrial tissue surrounding ostia 1501 of the pulmonary vein lumen 1502. None of the electrodes have been activated in FIG. 28A, although mapping procedures could also take place at this stage to assess the conduction of the cardiac tissue. FIG. 28B show certain electrodes "A" being activated and lesion regions 1503 starting to form in the tissue after the electrodes are making contact and power is applied. Electrodes designated "B" are not being activated in this example. FIG. 28C shows continued ablation of tissue and formation of lesion region 1504 that generally extends around the pulmonary vein ostia.

Figure 29A:
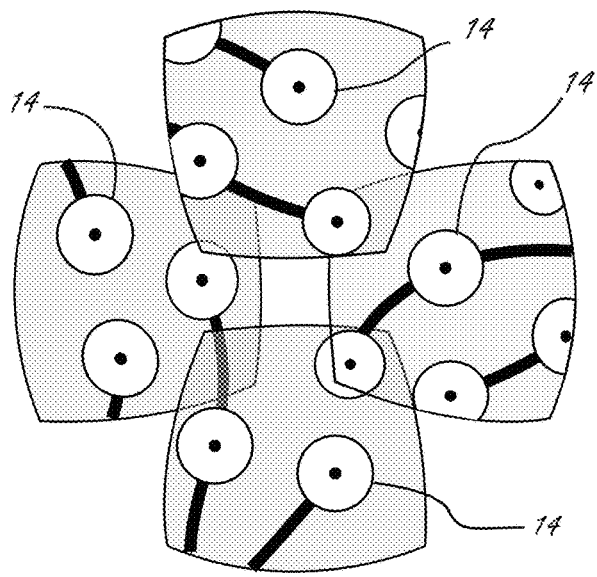
FIGS. 29A, 29B and 29C illustrate an exemplary method of ablating cardiac tissue.
Figure 29B:
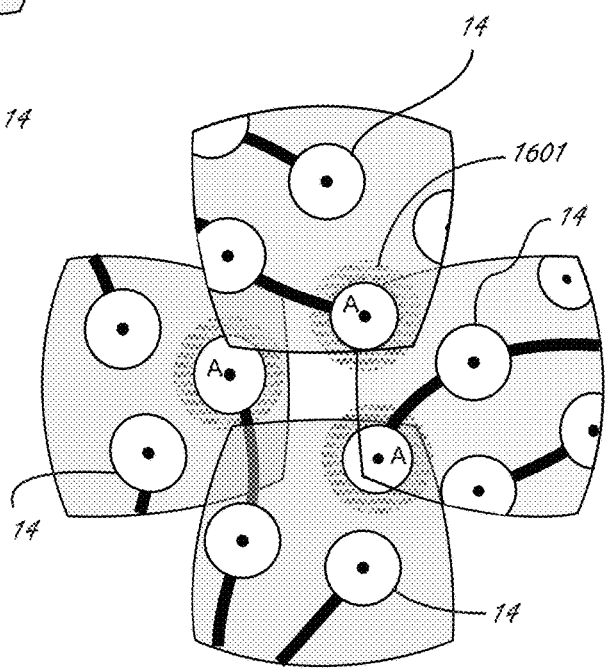
Figure 29C:
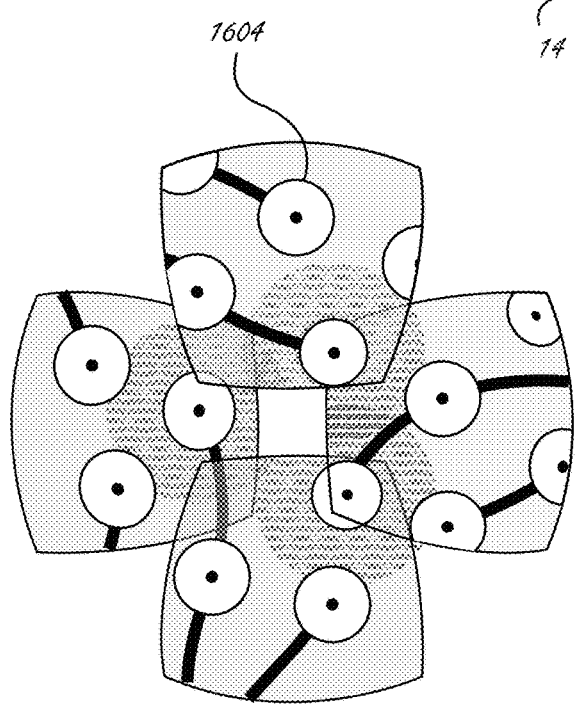
Figure 30:
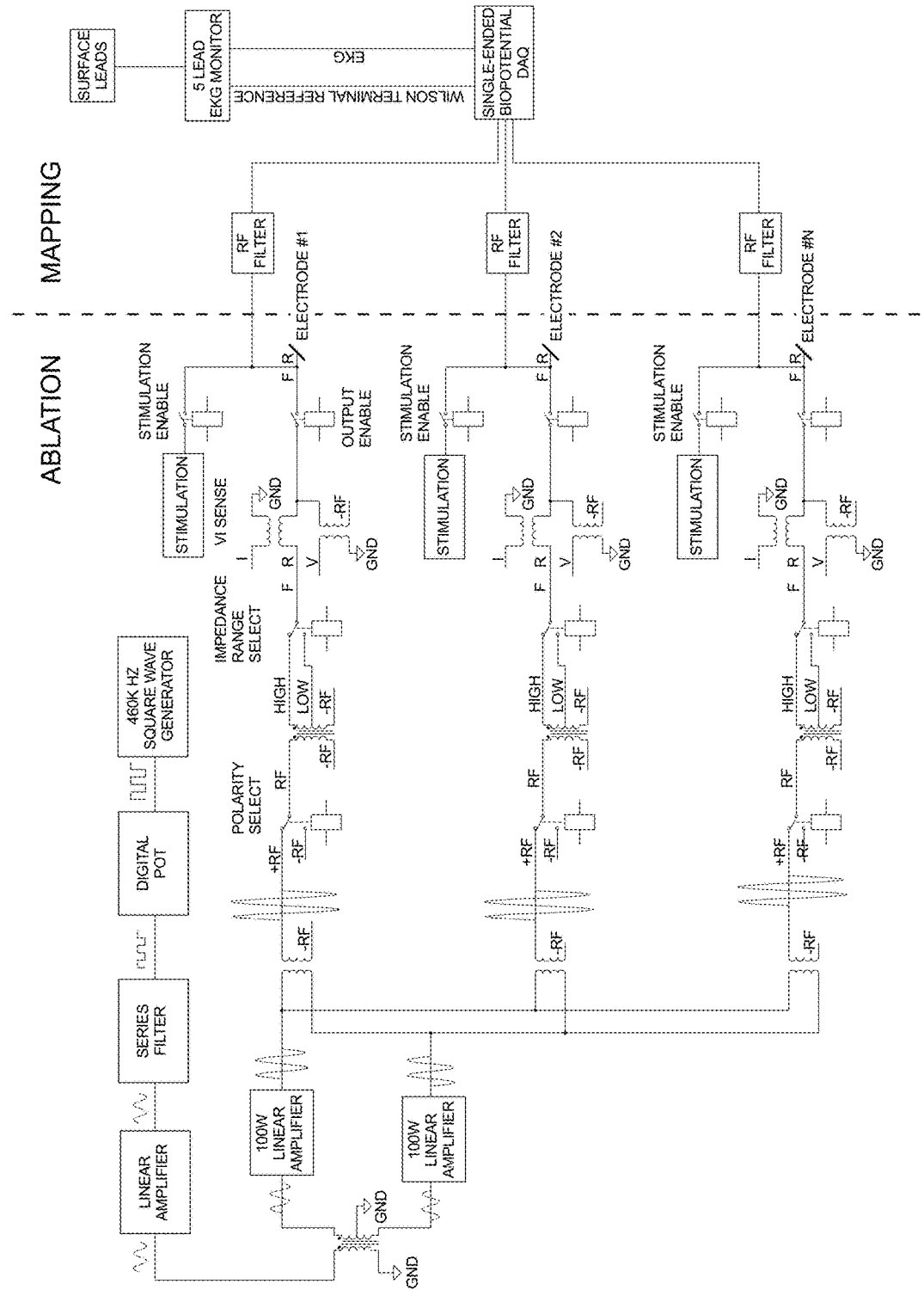
FIG. 30 is an exemplary schematic of the electrical aspect of an exemplary embodiment.

FIGS. 29A-29C illustrate an exemplary method of using the system herein to create lesion for treatment of a rotor. FIG. 29A shows the balloon advanced against cardiac tissue other than an ostia region, where none of the electrodes have been activated. FIG. 29B shows only electrodes "A" being activated, and ablation lesions 1601 starting to form where the electrodes are in contact with tissue and activated. In this embodiment, electrodes A are the distal most electrodes from each of the three flex circuits. FIG. 29C shows continued ablation and the formation of lesion region 1604 targeted at a rotor. The blind spot in the middle hides that the lesion extends over tissue that can't be seen. In alternative embodiments of use, more than three electrodes can be used to perform a rotor ablation, such as four or electrodes.

One aspect of the disclosure is a method of superimposing an image or images provided by the camera with information or an image that is an indication of at least one of a characteristic of the cardiac tissue and a characteristic of the ablation catheter. The superimposed images (or superimposed information and image) are presented to the physician in a visual display, such as a monitor, and can be part of a remote user interface. The aspect includes methods and systems adapted to superimpose images. The methods and devices herein are also adapted to obtain the information and superimpose the images.

The information that is being superimposed can be any suitable visual indicator of a characteristic of the cardiac tissue or a characteristic of the ablation catheter.

In some embodiments the information that is superimposed onto the image from the cameras is the electrical activity on the cardiac tissue contacting the expandable member.

In some embodiments the information that is superimposed onto the image from the cameras is the localized impedance of the ablation circuit.

In some embodiments the information that is superimposed onto the image from the cameras is the temperature of the cardiac tissue opposed to the balloon.

In some embodiments the camera comprising CMOS cameras are adapted to be responsive to light in the infrared range. The response can be used to estimate the temperature of the tissue before, during and or after ablation. The response can be interpreted by an algorithm and displayed superimposed to the visual light image from the cameras.

In some embodiments an accelerometer is placed at a location in, on or near the ablation balloon. The accelerometer can be used to detect the orientation of the balloon in relation to gravity. The accelerometer can produce acceleration data that is used to determine the accelerometer position in relation to an initial position. The position can be used to construct a database of locations visited by the balloon and/or information collected by the electrodes on the balloon and/or RF power applied to the balloon electrodes. The collection of information can be used to reconstruct a model to provide guidance to the physician in relation to the locations that are treated and locations that need to be treated.

Figure 35:
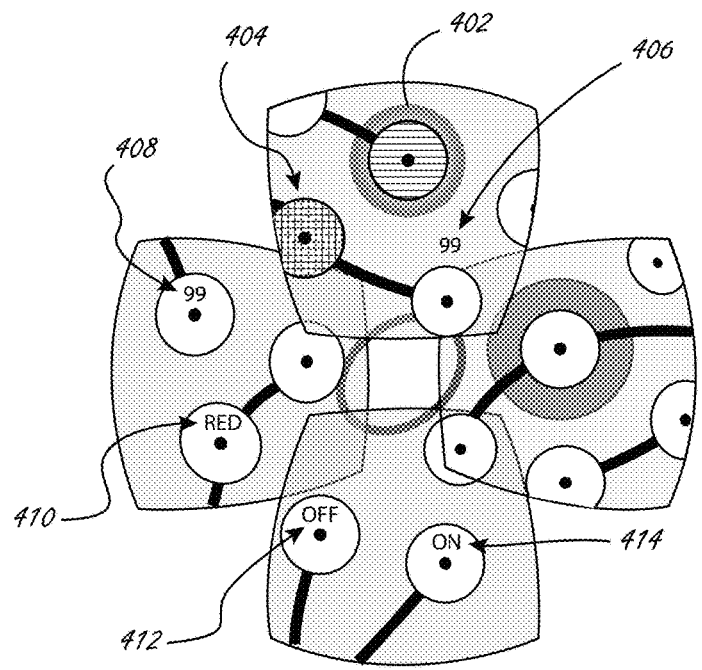
FIG. 35 illustrates exemplary information and indicators that can be superimposed on the images from the cameras.

FIG. 35 illustrates exemplary information and indicators that can be superimposed on the images from the cameras. Indicators 402 and 404 are examples of way to convey temperature of the tissue adjacent an electrode. For example, indicator 402 is a series of lines indicating qualitatively the temperature, such as "medium." Indicator 404 is a series of intersection lines and can indicate "high" temperature. Any type of visual indicators can thus be used to indicate the qualitative temperature of one or more tissue regions adjacent any of the electrodes.

Superimposed information 406 provides a qualitative indication of tissue temperature, in this example, 99 degrees. Information 406 is next to the image of the electrode, whereas information 408 is information that is on the electrode image. Indicator 410 is a red color superimposed on top of the electrode, providing a qualitative indication of "hot." Information 414 and 416 are superimposed to indicate that the respective electrodes are "on" and "off."

In some embodiments the superimposed information is all the same type of information. For example, each electrode can, at the same time, be superimposed with information indicating the temperature of tissue. In other embodiments, the type of superimposed information can be different for any of the electrodes.

Additional examples of the type of information that can be superimposed include electrical impedance, which can be visualized quantitatively or qualitatively using any of the indicators herein (e.g., color, numbers). Additionally, mapping signals can be superimposed on the camera images as well.

Figure 36:
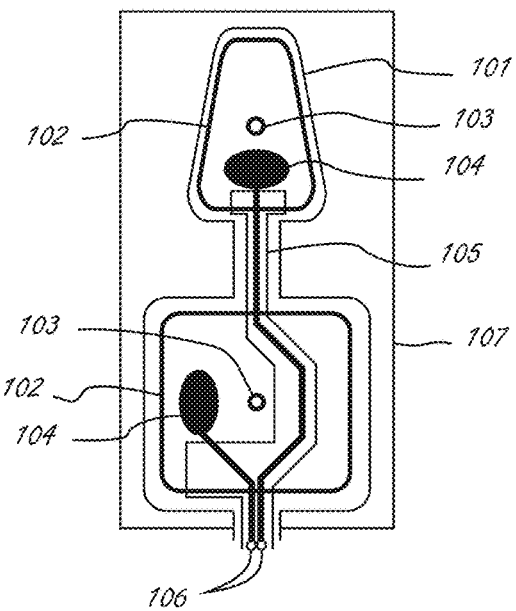
FIG. 36 represents an exemplary flexible circuit for application to the outer surface of a balloon.
Figure 37:
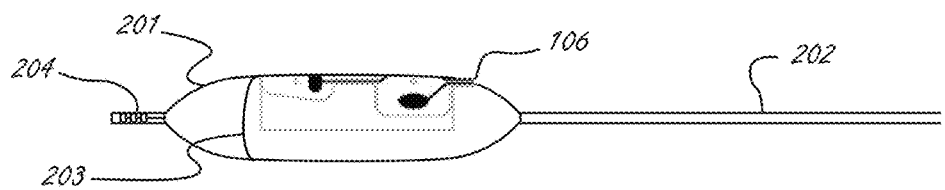
FIG. 37 shows an assembled flexible circuit affixed to a balloon.

FIG. 36 represents an exemplary flexible circuit for application to the outer surface of a balloon, with a thin polyimide substrate 101 approximately 0.002-0.003" thick and a total structural thickness between 0.004-0.006".

The outline is that of the final ablation pads 102 (only the large square and the triangle). Apertures 103 are for saline flow. Circuit traces 104 terminate in exposed areas on the ablation pads. Conductive silver paint is used to create the ablation pad geometry and the exposed trace provides conductivity.

Alternately, a black adhesive may be used to darken the areas under silver painted ablation pads 102 to prevent reflections inside the balloon, as is described herein. One method of employing polyimide substrate 101 can eliminate the black adhesive providing a thinner and more compliant mounting surface. In some embodiments there is a light absorbing layer and material disposed between the camera and the electrode, to reduce reflection of the light in the field of view. The light absorber can have the same base material as the electrode, but have no or little conductive properties. In these embodiments at least a portion of the electrode is thus not in direct contact with the expandable member, while the light absorber can be in direct contact with the expandable member. Alternatively, the light absorbing portion may comprise a conductive material such as carbon nanotubes which will provide the light absorbing quality and the electrical conduction quality.

A dielectric area 105 is provided to prevent cross talk and conductivity to the blood or other medium. The proximal side of the flex circuit has two small solder pads 106 where the wires are attached.

Figure 40:
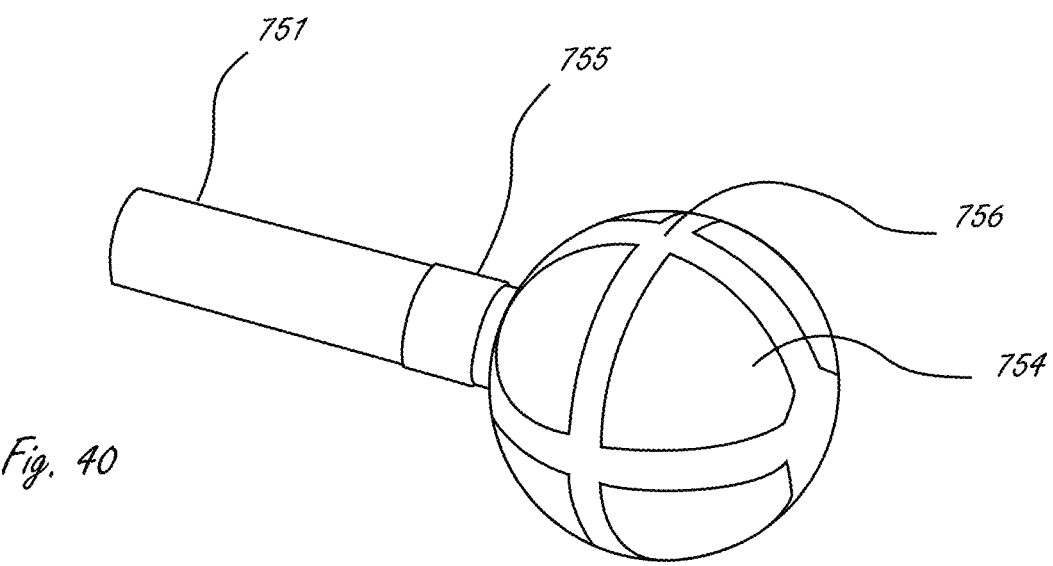

An assembled flexible circuit as represented in FIG. 3 can be affixed to balloon 201 as shown in FIG. 40, such balloon being located around a central stem 202, and such stem having a system to capture the image of the internal surface of the balloon (not shown) and transmit such image to a display outside the patient. An optional long protrusion 203 distal to the triangle pad which wraps around the front of the balloon to create a physical anchor for the circuit.

Additionally an accelerometer 204 is placed at a location in, on or near the ablation balloon, such accelerometer can be used to detect the orientation of the balloon in relation to gravity and to construct treatment relevant data sets as described herein.

When the physician moves the catheters as described herein, more specifically, when the physician rotates the system around the longitudinal axis of the catheter, the image display will show the internal surface of the balloon fixed and everything outside the balloon (e.g., cardiac tissue) moving. This is due to the fact that the cameras, in the embodiments herein, are fixed in relation to the catheter and balloon system.

Figure 38A:
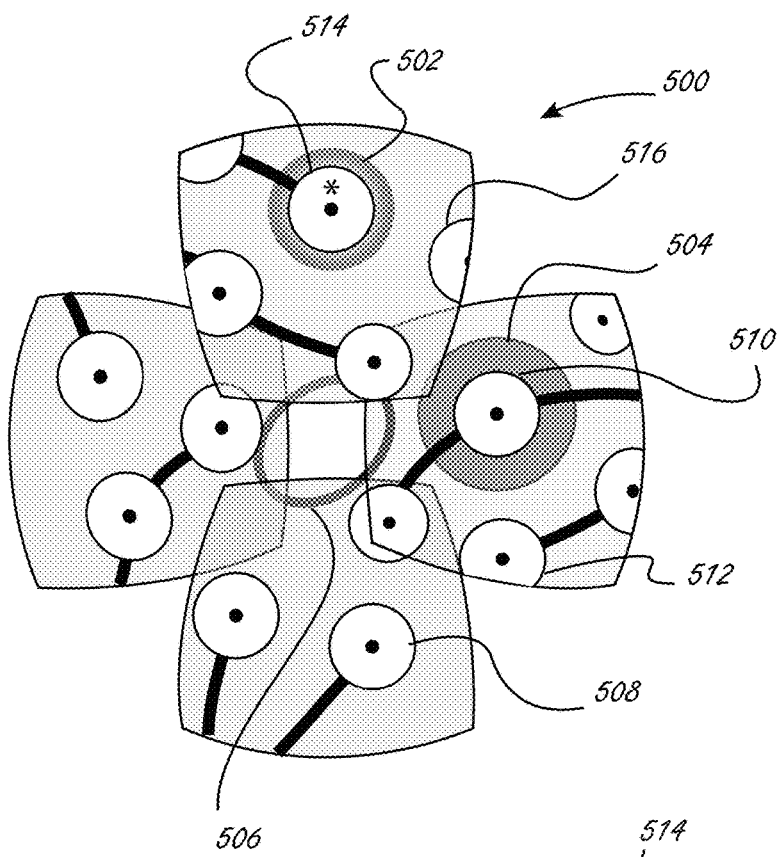
FIGS. 38A and 38B illustrate a composite view as described herein from a four camera array as presented to the user on a display.
Figure 38B:
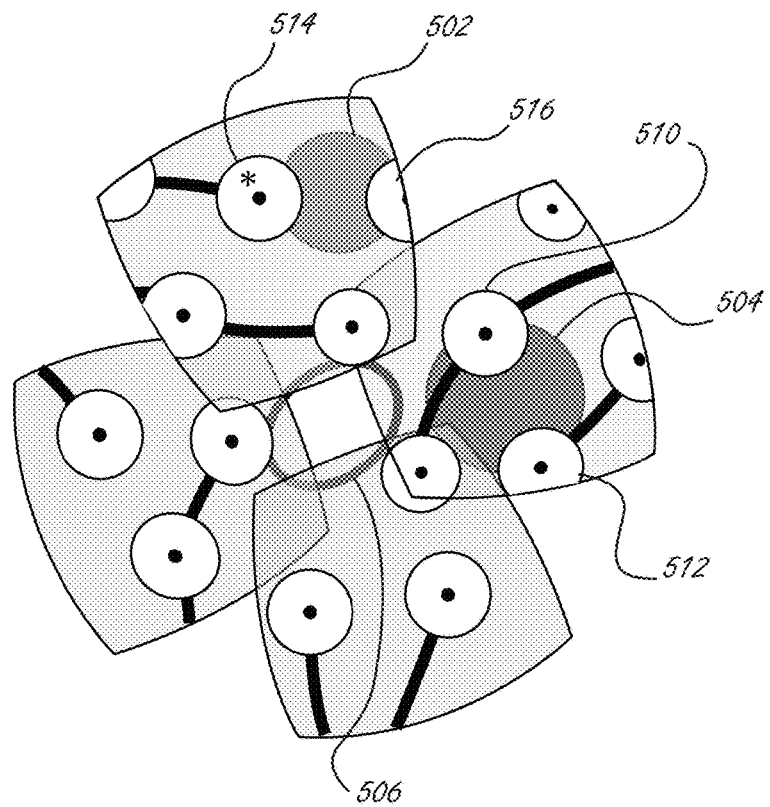

FIGS. 38A and 38B illustrate a composite view as described herein from a four camera array as presented to the user on a display. The images are mapped to a composite image representing the arrangement and orientation of cameras carried by the balloon on the shaft within the balloon. The mapping registration relies on mapping common features within each camera field of view over each other where there are common features within two or more images. As illustrated, one electrode, the orientation registration electrode, is identifiable by a marking in the shape of an asterisk (as shown) which has been printed on the balloon prior to the electrode and is visible to the camera. In other embodiments each electrode may be marked with its own unique identifier or some or all electrodes may have different shapes which help to identify them. The common fixed features (relative to the cameras) include traces, electrodes and other fixed markings. FIG. 38A illustrates an initial image taken just after burns 502 and 504 created by electrodes 514 and 510 respectively. The balloon is centered around a pulmonary vein 506. FIG. 38B illustrates a second image captured by the camera array after the balloon is rotated. Each composite image has been processed such that the fixed features (relative to the cameras) are mapped to the user display in a fashion such that the registration mark (and hence the entire image) is rotated an amount equal and opposite to the rotation measured for the center of mass of one or more of the anatomical features around the center of the composite image such as burns 502 or 504. By so doing the image of the fixed features will rotate while the portion of the image behind the fixed features will remain fixed as the balloon is manipulated.

Disclosed here therefore is a system to, through image processing, show the internal surface of the balloon rotating while maintaining still, or fixed, the image of everything outside the balloon (e.g., tissue). In this manner, the image of everything that is not part of the catheter will remain fixed, and everything that is part of the catheter will be shown in the video to rotate. In this alternate embodiment, the image that the user views shows the fixed features (e.g., electrodes) being rotated while anatomical features remain still. The anatomical features are the non-fixed features or non-balloon related features in the tissue such as, represented in this view, the pulmonary vein, and the images of burns created by ablation. This is accomplished even though the fixed features move as the camera moves. Keeping the tissue fixed for the user, and having the device components move allows the physician to better control the movement of the device relative to the tissue. To facilitate this procedure the mean rotation of the center of mass of one or more of the key anatomical feature are calculated relative to the location of the fixed features. The mean or other suitable representation of the rotation(s) is then used to rotate the composite image as presented on the user display.

Figure 34:
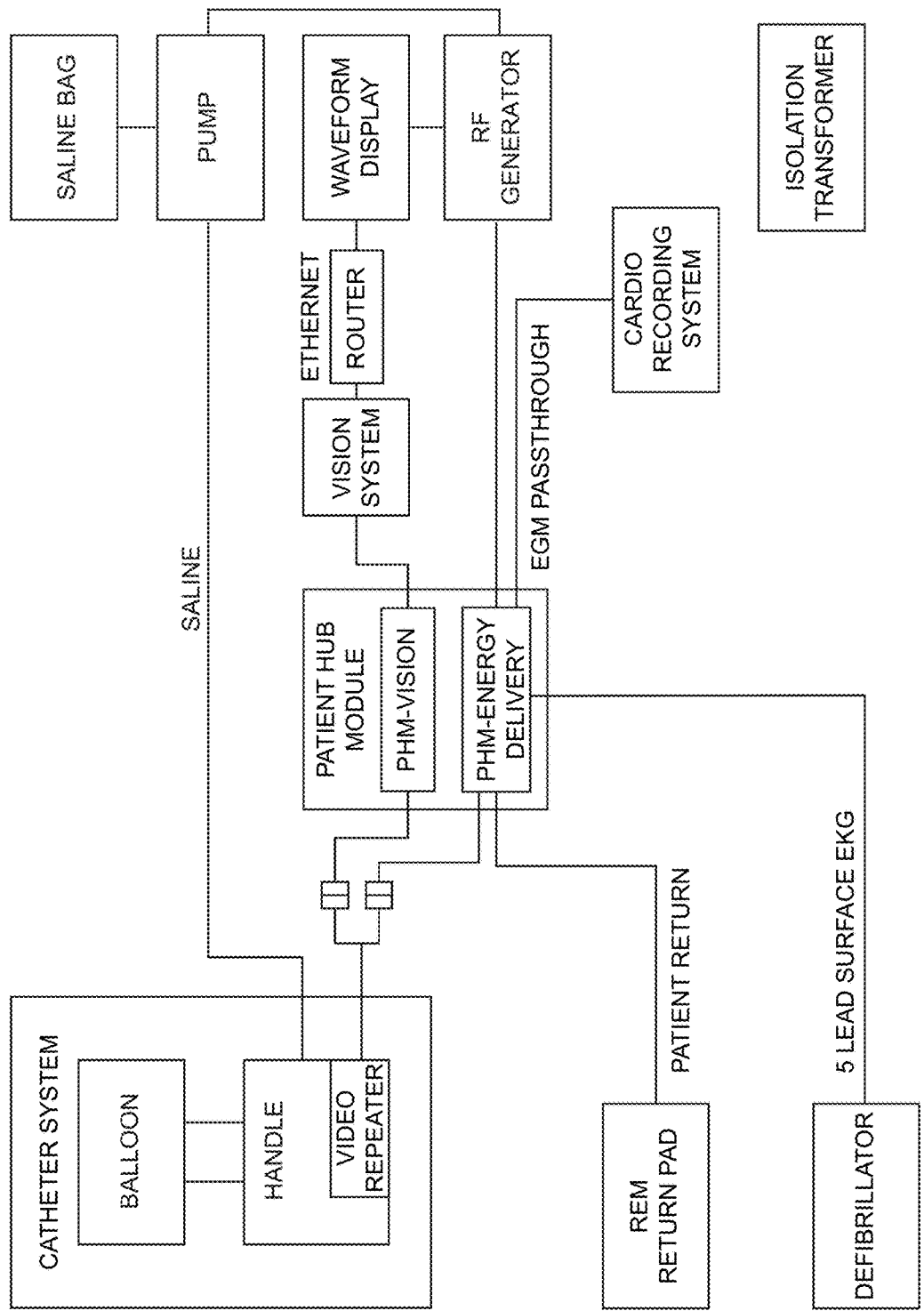
FIG. 34 illustrates an exemplary block diagram of a cardiac ablation system.

FIG. 34 illustrates an exemplary block diagram of a cardiac ablation system, details of which are described herein. Any of the system components in FIG. 38 can be incorporated and used with any of the individual components described herein.

Figure 31:
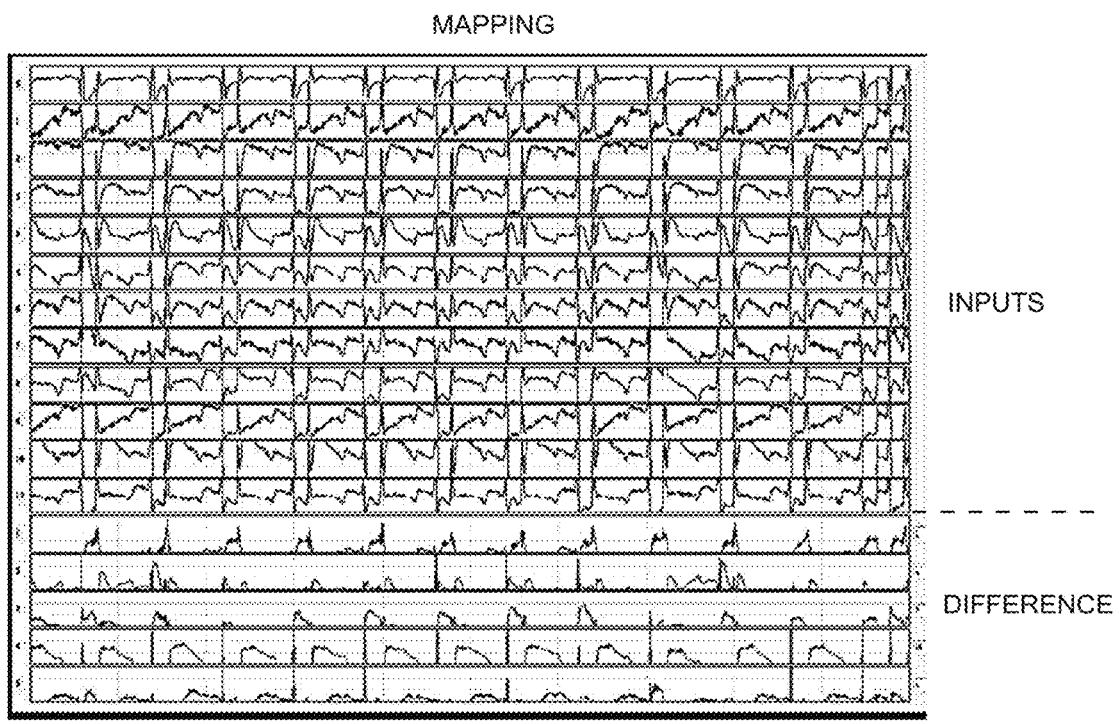
FIG. 31 illustrates mapping signals from a plurality of channels.

The number and arrangement of the electrodes disposed on the expandable member, each of which is individually addressable and can be used to deliver energy in either monopolar or bipolar mode, provides for a wide variety of lesion formations without having to remove and insert a separate RF catheter. The exemplary methods shown in FIGS. 31 and 32 are merely exemplary. Linear lesions and arc lesions are additional examples of lesion shapes that can be created depending on the desired ablation procedure. In the specific example provided herein, there are eighteen individually addressable electrodes disposed on substantially the distal portion of expandable member 10. Any of them can be energized while others are not, allowing for many different lesion formations to be made in cardiac or other tissue for treating cardiac arrhythmias. Any of the electrodes can be used in bipolar mode with any other electrode as well. Depth and width of lesions may be controlled by choosing and/or varying what combination of electrodes are being used in bipolar and monopolar configurations. Monopolar configuration creates deeper, narrower lesions, and bipolar configuration creates shallower, wider lesions.

One of the advantages of the devices herein is that the number and arrangement of electrodes allow for a wide variety of lesion formations without removing and inserting a new catheter. And the visualization system allows for the entire procedure to be visualized.

Figure 7:
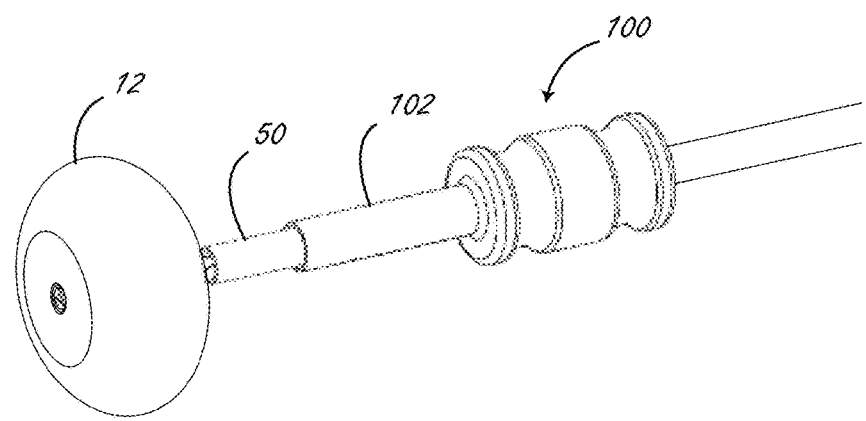
FIG. 7 illustrates the distal end of a device incorporating a slidable sheathing tool comprising a sheathing tube.

FIG. 7 illustrates the distal end of the device incorporating a slidable sheathing tool 100 comprising sheathing tube 102. In use, balloon 12 is collapsed as previously described and then the sheathing tool is slid over the collapsed balloon. The sheathing tube 102 is then fit into the delivery catheter, not shown. The sheathing fixture is then removed, leaving the collapsed balloon within the deliver catheter ready for advancement to the delivery site.

One aspect of the disclosure is a delivery catheter comprising concentric sheaths as a steering mechanism with a mapping system built into the distal tip, where a mapping basket resides during delivery in the space between the two concentric shafts and on delivery is pushed forward out into the heart chamber. Examples of deployable mapping baskets are described above. An ablation catheter may then be delivered through the delivery catheter with the mapping basket in place. Target locations for ablation can then be identified using the electrodes on the mapping basket and target locations are then ablated with the ablation catheter. The location of the ablation catheter may in addition be identified and verified by the mapping basket.

One aspect of the disclosure is an ablation catheter that includes an electrode structure that is about 1 cm to about 5 cm in diameter and resides on the end of an inflatable or expandable structure and may comprise any of the following: an ablation catheter with a balloon carrying multiple electrodes. In some embodiments the multiple electrodes are used alternatively as a single ablation electrode then as a set of individual impedance sensing electrodes capable of monitoring the inter electrode impedance. Such measurements are useful in characterizing the efficacy of the burn resulting from the ablation and/or mapping the ablated area before or after the burn. In some embodiments contact pressure sensitive electrodes may be incorporated as a means of verifying appropriate contact of the electrode to the cardiac tissue. In many embodiments irrigation is provided as described elsewhere herein, wherein the irrigation system incorporates a pressure sensor. In such embodiments contact pressure may be inferred from changes in pressure within the irrigation system associated with increasing the outflow resistance at the irrigation outflow ports press against tissue. In other embodiments a balloon within a balloon configuration is used such that irrigation pressure may be isolated from inflation pressure. The change in pressure within the inflation system then is directly correlated to the contact pressure. In another alternative cooling may be provided by recirculation within the balloon as opposed to irrigation.

In some embodiments the contact pressure of an electrode is measured by impedance matching. An alternate means of characterizing the quality of lesions is to measure changes in acoustic impedance in the ultrasonic pass band. The acoustic impedance will be changed from that of normal tissue both as a function of temperature and denaturation. In such an embodiment a forward looking US transponder can be incorporated in the balloon or on the surface of the balloon. Such a sensor may be embodied as an array of one or more transponders, an array of one or more transmitters and an array of one or more receivers, or a single transponder.

In an alternate embodiment temperature of the lesion may be monitored by microwave radiometry.

Figure 39:
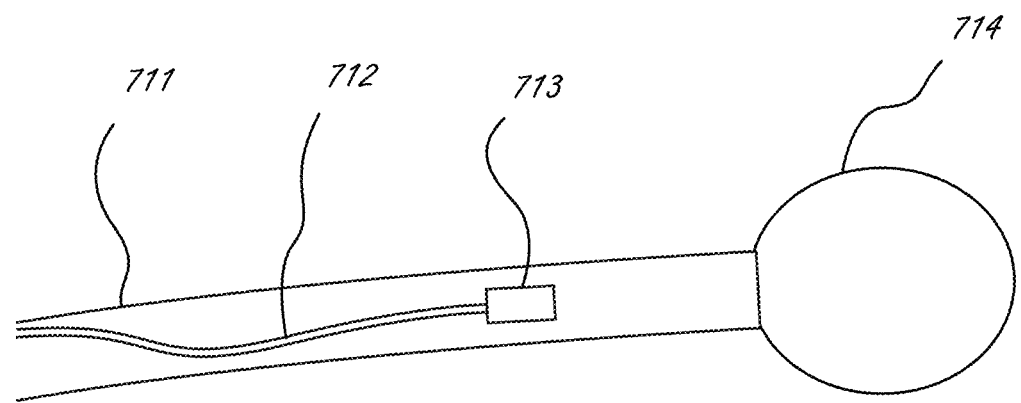
FIGS. 39 and 40 illustrate an exemplary embodiment of an ablation catheter wherein the balloon is configured for contact (physical) measurements.

FIGS. 39 and 40 illustrate an exemplary embodiment of an ablation catheter wherein the balloon is configured for contact (physical) measurements. Contact pressure of the balloon and therefore electrodes as characterized by variations in the internal balloon pressure resulting from irrigation holes in the balloon which pass through electrodes being occluded as the electrode is pressed against the tissue. Pressure will increase transiently as the balloon is pressed against the tissue and then reach a new equilibrium associated with any decrease in outflow resistance associated with the occlusion or partial occlusion of irrigation ports. This contact pressure can be mapped by previous experiments to an electrode contact surface area. A visual contact monitor comprised of a camera within the expandable structure monitors contact as a change in the visual appearance of transparent portions in the balloon. The changes in visual appearance result from differences in the appearance of blood and tissue in contact with the expandable member.

Contact monitoring may be used to control power delivery. Measurements of electrode contact obtained by any of the means described herein can be used to mediate the amount of power delivered to an electrode. One control algorithm limits power to an electrode such that the power per area of contact surface is maintained at a constant level.

FIG. 39 illustrates a prototype balloon configured for contact measurement. Balloon 714 is affixed to the end of shaft 711. Strain gauge 713 is affixed to shaft 711 and leads 712 which are interfaced with a strain gauge amplifier not shown. There are two additional strain gauges affixed to the shaft at plus and minus 120 degrees. FIG. 40 is a representation of a similar device in which all three strain gauges are configured in strain gauge assembly 755 on shaft 751 which comprises the leads to the strain gauge assembly. Balloon 754 comprises electrodes 756. In alternate embodiments the pressure of enclosed volumes of fluids or gels arranged in cells near the proximal attachment of the balloon may be monitored via one or more pressure sensors. In yet other embodiments the strain gauges may be replaced with displacement sensors. As indicated above measurements from such sensing systems can be mapped to an estimate of electrode contact surface. The balloon of FIG. 39 is 2 cm in diameter and that of FIG. 40 may be 1 to 3 cm in diameter. The configuration of electrodes on the device of FIG. 40 comprises eight electrodes. Such a small profile allows small delivery size and precise maneuverability. Such a system is compatible with a single RF generator and may comprise an irrigation system, not shown, to minimize unwanted injury.

Patient Mapping

This disclosure also includes devices and systems adapted for, and methods of, creating a patient map, such as, for example without limitation, a patient map of at least a portion of a left atrium. Patient map creation combines a plurality of different captured 2D images of the anatomy adjacent the expandable member, each of the plurality of captured 2D images visualizing at least one part of the patient (e.g., tissue) that was in contact with the expandable member when the image was captured. The methods and systems rely on a known or determinable distance between a camera and a location on the expandable member, and a location element in fixed relation with the visualization system, such that the methods can tag each of the plurality of captured 2D images with a position and orientation (together referred to herein as "location) of the 2D image in a global frame of reference. The plurality of 2D image can then be placed in a 3 space (a space defined by 3 coordinates—x, y, z) at their tagged position to create the patient map, which can then be displayed on a monitor or screen. Patient maps as used herein can be represented as projections in 2D or 3D on the screen. For example, a 3D view of the patient map can be displayed, or a 2D representation of the patient map can be displayed on the screen.

The mapping herein includes combining different images captured by the visualization system, wherein the images are captured as the visualization system is moved within and placed in contact with the tissue of the patient (e.g., by moving the catheter or field of view of the camera). As the visualization is moved relative to the patient, a plurality of different 2D images are captured and used to create the maps herein.

The patient maps that are created herein are different from volume patient maps, which can be generated using, for example, ultrasound systems, CT systems, and MRI systems. Volumetric maps are generally created by obtaining 2D slices of a patient using the imaging system, which are then combined into a volume of at least a part of the patient. The systems can allow a user to scan through the 2D slices or the 3D composite to visualize different parts of the volume. The volumes created using these systems are different than the patient maps described herein.

As set forth above, some previous tissue locational mapping systems, such as those that can map a left atrium, use a point-by-point mapping system, and use the relatively large number of individual points to create a 3D patient map. Systems herein can create tissue maps in 3 space without having to rely on this type of point-by-point process.

In some embodiments, the medical device (e.g., cardiac ablation catheter, cardiac visualization and mapping catheter) includes a visualization system, such as any of the systems herein including one or more cameras, and a locational element in a fixed position relative to one or more components of the visualization system. A locational element is generally referred to herein as one or more components whose position and/or orientation can be detected relative to a global frame of reference. For example without limitation, the Aurora electromagnetic tracking system sold by NDI Medical (located in Waterloo, Ontario, Canada N2V 1C5) utilizes a field generator that emits a low-intensity, varying electromagnetic field within which the patient is placed to track the position of a sensor, which can be a plurality of orthogonal coils. The electromagnetic tracking system and software determines the position and orientation of the sensor within the global frame of reference.

In some exemplary embodiments, an ablation catheter having one or more visualization elements (e.g., cameras), such as any of the catheters herein, can also include a locational element in the form of a three orthogonal sensor coils, whose position and orientation can be sensed by a tracking system, such as an electromagnetic tracking system such as the Aurora system sold by NDI, CARTO™, or the EnSite™ NavX™ systems. In some embodiments other magnetic or RF field detectors such as magneto restrictive sensors may replace the coils.

When the locational element has a fixed, or at least known, position and orientation relative to the visualization system, information obtained with the visualization system can then be associated with the tracking system's global frame of reference. For example, in some embodiments, the methods herein determine the location and orientation of a subsurface, or portion, of the target surface, and then compile the subsurfaces into a representation, or patient map, of the target surface.

Some methods are also adapted to image surface structural features (anatomical or created) visualized by the mapping system and map such features onto the patient map of the target surface. Some methods herein are also adapted to characterize one or more anatomical structures in the target tissue and the location in the patient map. Exemplary anatomical structures include the inner surface of a chamber of a heart, such as a left atrium, and exemplary structures include trabeculations, pulmonary veins, corina, vessels just behind the endocardia a septum or other natural features visible via light to which the camera is sensitive. Some methods herein are also adapted to characterize physiological processes occurring within or on the surface of the modeled tissue. Exemplary physiological processes include electrical signals, such as rotors or electrocardiological signals traveling through the cardiac muscle, and are described in more detail below. Some methods herein are also adapted to characterize stimulatable physiological structures occurring within or near the surface of the modeled tissue. Exemplary stimulatable physiological structures include autonomic ganglia, Bachmann's bundle, the phrenic nerve. Some methods herein are also adapted to characterize injuries marking created on and or in the tissue by the medical device such as burns, dye markings, or other injuries.

Figure 41:
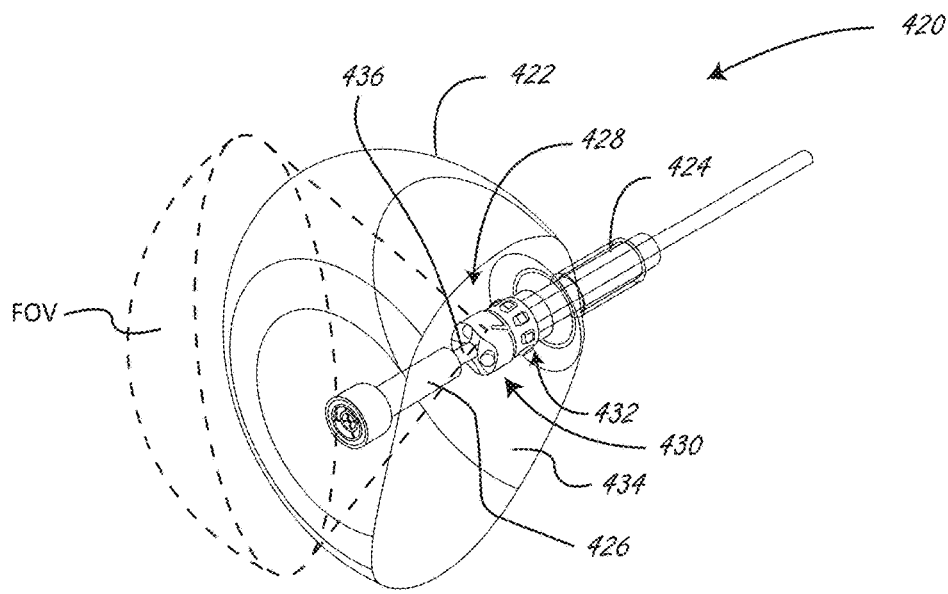
FIG. 41 illustrates a portion of an exemplary ablation and visualization catheter, which includes a locational element.

FIG. 41 illustrates an exemplary medical device adapted for use in creating a patient map. FIG. 41 shows a distal portion of ablation catheter 420, wherein ablation catheter 420 is similar to some catheters above. Catheter 420 includes expandable membrane 422, with irrigation holes, secured to a distal region of elongate body 424. Within expandable membrane 422 are locational element 426 and visualization system 428. Visualization system 428 includes one or more cameras 430 and light source 432. Catheter 420 also includes diffuse reflector 434. Locational element 426 is secured to inner shaft 436, which can include a guidewire lumen therein. Locational element 426 has a position and orientation that are fixed relative to the one or more cameras 430, including the camera field of view (one of which is shown as "FOV"). Locational element 426 can include a coil whose position in 3 space (x, y, z) and orientation can be detected by a tracking system, Catheter 420 also includes one or more markers carried by the expandable membrane. "Carried by" as used in this context can be one or more elements external to an external surface of the expandable membrane (directly or indirectly secured thereto), something integral with the membrane, or something internal to the inner surface of the membrane. Examples of external markers include RF electrodes (ablation and/or sending) or one or more components of a flexible circuit secured relative to an external surface of the expandable membrane. Additional examples of a marker can be a visual marker such as visual markings with known dimensions and distances between them (e.g., lines or other shapes with known dimensions and known distances between them). In some embodiments the catheter also includes one or more electrodes (ablation and/or sensing) and one or more flex circuits carried by the expandable membrane, examples of which are described above. Catheter 420 can be used in any of the manners described above for any of delivery, inflation, ablation, and sensing.

An exemplary use of the methods and systems herein is in creating a patient map of at least a portion of a chamber of the heart, such as the surface of a left atrium and it's structural and electrical features, such as the pulmonary veins, trabeculations, septum, electrical signals traveling through the muscle including rotors and other aberrant signals, nerves, nerve bundles passing through or near areas of the heart, and any other conduction features. Such an exemplary system can be used in the treatment of atrial fibrillation and other similar diseases.

Figure 42:
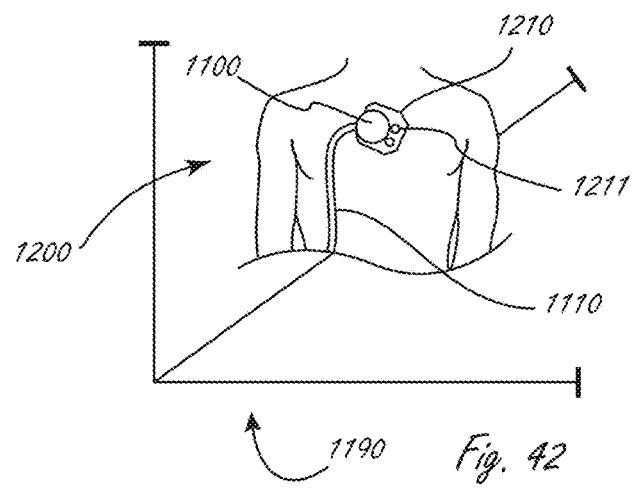
FIG. 42 represents a cardiac ablation catheter within a left atrium and within a global reference frame.

FIG. 42 illustrates the distal end an embodiment of a patient mapping (which may also be referred to here as surface mapping) and visualizing ablation system. As shown, the distal end of the ablation catheter 1100 secured to and delivered by elongate shaft or catheter 1110 is contacting the left atrium posterior surface 1210 within a patient's chest 1200. One of the pulmonary vein ostia 1211 is labeled on the pictured surface. The left atrium and its posterior surface are in a 3D mappable volume 1190.

Figure 43:
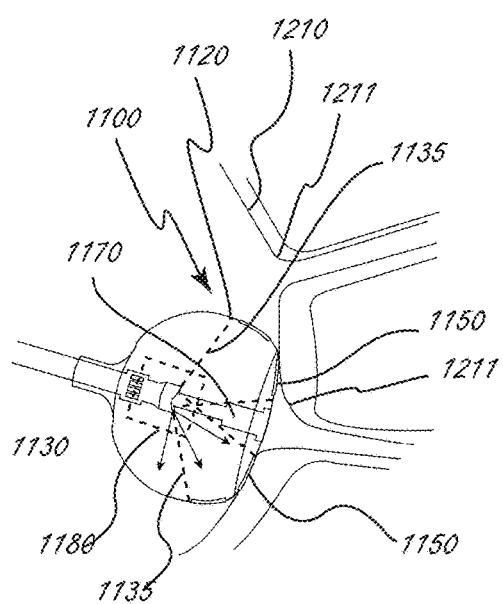
FIG. 43 illustrates an exemplary ablation and visualization catheter in contact with atrial tissue.

FIG. 43 illustrates a side sectional view of the distal region of a surface mapping and visualizing ablation system (which can be the same or similar to ablation catheter 420 in FIG. 41), contacting the posterior surface of a left atrium 1210. As illustrated, the inflatable membrane or balloon 1120 is shown contacting atrial wall tissue 1210 around a pulmonary vein ostia 1211. Two cameras 1130 and associated fields of view 1135 (dashed lines) can be seen within the balloon. The cameras are carried by and on a tubular shaft through which a guide wire lumen passes. The cross section as shown shows four electrodes 1150, two of which are contacting atrial tissue and two of which are not. A locational element 1170 is disposed on and carried by the outer surface of the elongate member in which the guide wire lumen is disposed. The electrodes and/or the support circuitry (e.g., flex circuits) can function as markers (also referred to herein as "visualization elements"), which is described in more detail below. A reference frame 1180 (x, y, z axes) is shown superimposed on one of the cameras 1130.

FIGS. 44A-44E illustrate exemplary steps in a process in which a system can be used to create a patient map, and in this embodiment the patient map includes the surface of a left atrium. The exemplary process can be of use in providing an ablation treatment for the treatment of atrial fibrillation. Part of the process is determining, or characterizing, the position of one or more regions or points of interest on the tissue, within a global frame of reference. The global frame of reference is defined by a tracking system that senses the position and orientation of the locational element. The location and orientation of position vectors associated with system components (e.g., camera) and features either in or on the tissue can be summed to characterize the position of the point or region of interest within the global reference frame. This may include mapping position vectors defined in local frames of reference into positions defined within the global frame. This can include mapping the position of a feature, features, or tissue (or any other part of the patient) that is in contact with the expandable membrane into the global frame.

The following conventions will be used to describe frames of reference, position vectors, and transformations herein. Frames of reference will begin with a capitol letter followed by "f." Exemplary frames of reference described herein are, the global frame ("Gf"), the locational element frame ("Lf"), and the reference frame of a Camera ("Cf"). Position vectors will be designated herein by pairs of capital letters, the first letter indicative of a starting point, and the second letter indicative of an end point for a position vector. "GL" is an exemplary position vector, describing the position vector starting at the origin in the global frame "Gf" and ending at the locational element. GL is typically measured by the locational tracking system, an example of which is the Aurora system. Vector "LC" describes the position vector measured from the locational element to a camera. LC is typically fixed by the design of the catheter. "CS" is a position vector measured from a point on a camera to a point on a visualized surface. CS is typically calculated as set forth below. "GS" is the position of point "p" on a surface measured from the origin of Gf to the point. When a position vector is listed with a subscript, the subscript indicates the frame in which it is characterized. An element characterized in the global frame may or may not use the frame indication.

Figure 44A:
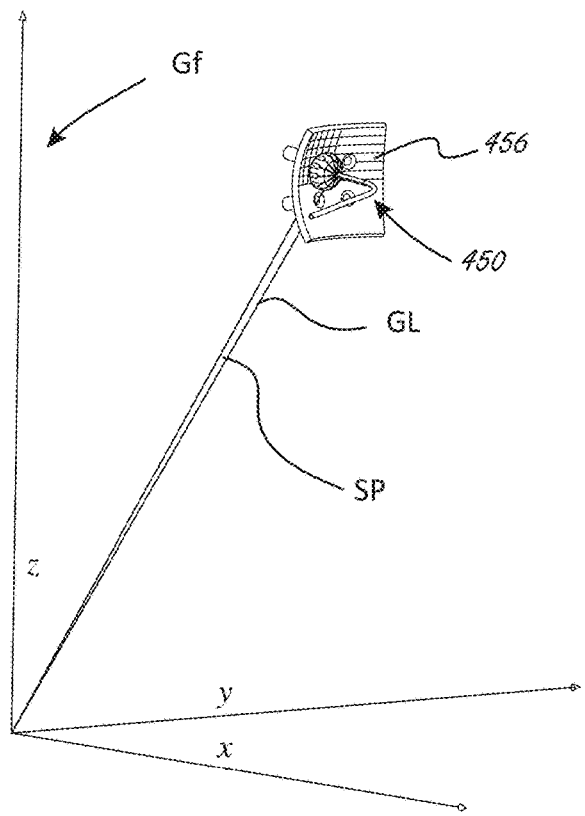
FIGS. 44A, 44B, 44C, 44D, and 44E illustrate exemplary steps in a process in which a system can be used to create a patient map, and in this embodiment the patient map includes the surface of a left atrium.
Figure 44B:
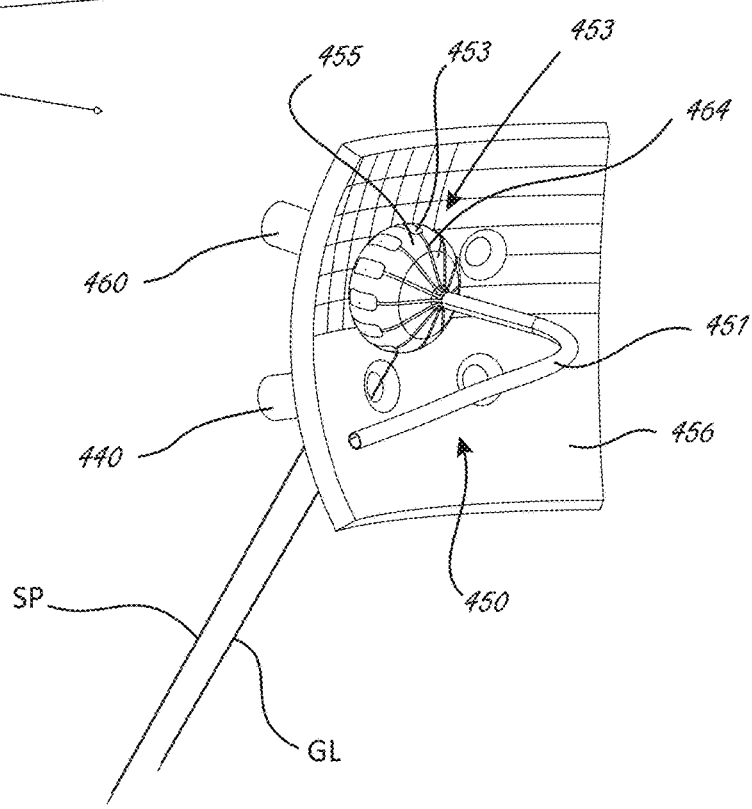

FIGS. 44A-44E illustrate, conceptually, position vectors and relative frames of reference, used in the process of characterizing a point P on the atrial wall, the point described by the position vector GS. FIG. 44A-44E illustrates a global reference frame "GF", with axes x, y, z, which provides the reference frame for the position and orientation of the locational element. FIG. 44A shows, and FIG. 44B shows in more detail, a distal region of an exemplary catheter 450, for which an expandable member is in contact with a surface of atrial wall 456 about an ostium of one of the pulmonary veins 460. Catheter 450 can be used in a process to create a patient map of the surface of the atrial wall, whether a 2D or 3D map. FIGS. 44A and 44B show a position vector "GL" for the locational element 457, as well as a position vector "GS" for a point on the atrial wall surface whose position within the global reference frame is desired. Three of these points can be used to characterize a surface to map into the global frame of reference.

Figure 44C:
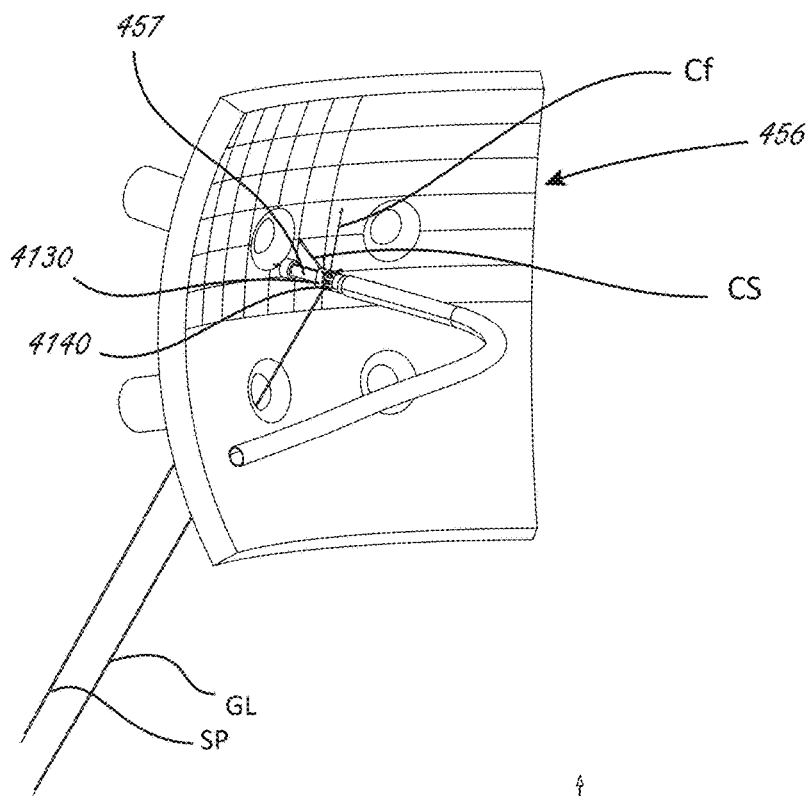
Figure 44D:
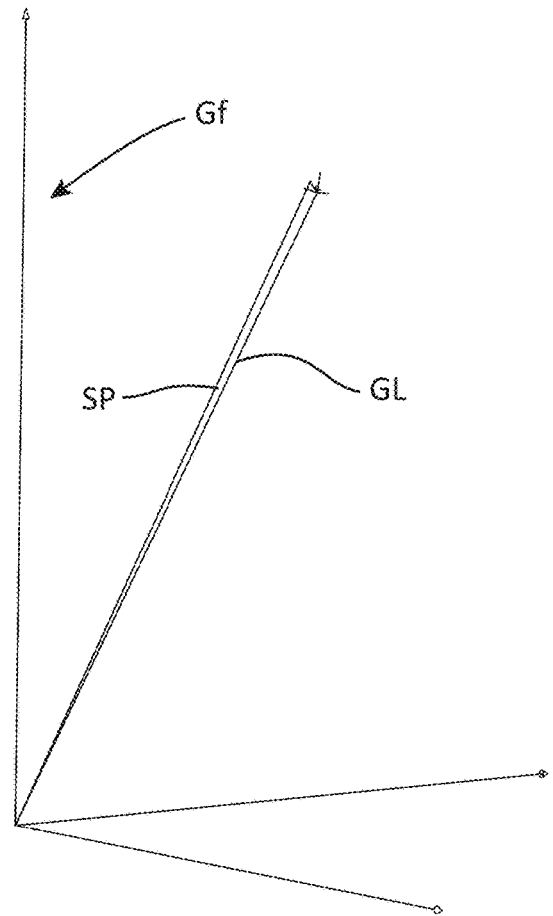
Figure 44E:
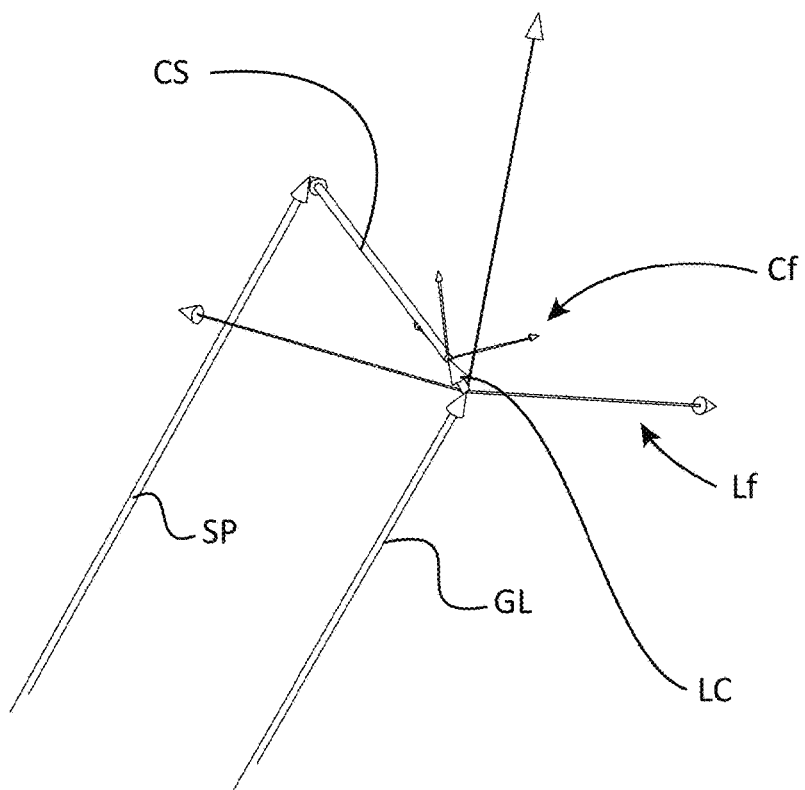

FIG. 44C illustrates the view of FIG. 44B, but the expandable member has been removed for clarity. Locational element 457 can be seen near the distal end of the catheter, the position and orientation of which can be characterized by the global mapping system which defines the global frame Gf. The visualization system includes three cameras (more or fewer can be used; any assembly herein or known can be used), whose position and orientation relative to the locational element are fixed. The visualizing system also includes one or more light sources (such as any of the lighting assemblies herein or known), which can also be seen secured to the catheter. The frame of reference "Cf" for a first camera is also shown, as is the position vector "CS" from the camera to the point of interest on the surface of the atrial wall. Each camera has a reference frame Cf associated with its field of view and is aligned such that one axis of the reference frame Cf is collinear with the optical axis of the camera. FIG. 44D shows just the references frames and the position vectors. FIG. 44E shows a close-up view of the position vector GL for the locational element, the locational element frame of reference "Lf," position vector "LC" from the locational element to the camera, camera frame of reference "Cf" the position vector from the camera to the point of interest on the atrial wall, the position vector GL for the locational element, and position vector SP for the point of interest on the wall.

A transformation of the coordinates of a position vector in one frame to another is described herein as $T^{Sf}_{Ef}(V)$, which describes a transformation from "Sf", the starting frame, to "Ef", the ending frame, on position vector "V". When using a system as described above, the position of a point GS(p) on a surface, can be characterized by summing the vector sum GS (which is to be determined)=GL+LC+CS. Given the system described, this vector sum will be described as $GS=GL+LC_{Gf}+CS_{Gf}$, given the measurement systems comprised in the system. With appropriate transformations, the equation can be written as: $GS=GL+LC_{Gf}+CS_{Gf}$, which can become $GL+T^{Lf}_{Gf}(LC)+T^{Cf}_{Gf}(CS))$, which can become $GL+T^{Lf}_{Gf}(LC)+T^{Lf}_{Gf}(T^{Cf}_{Lf}(CS))$. Such transformations are described in known literature in additional detail. The final equation can thus be used to determine the position vector GS, which is a characterization of the point in the global frame of reference.

Figure 45:
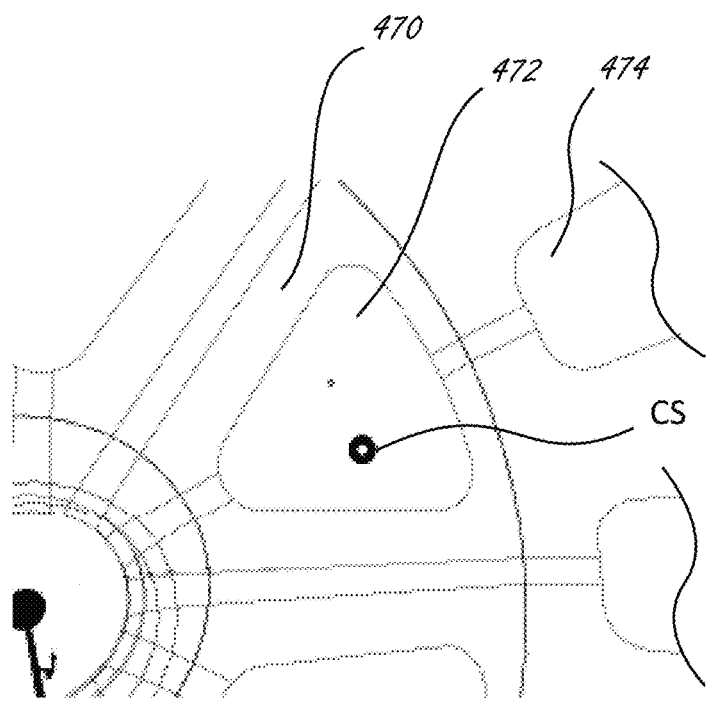
FIG. 45 illustrates an exemplary view from a camera from inside an expandable membrane of an exemplary visualization and ablation catheter.

FIG. 45 illustrates an exemplary view from a camera from inside an expandable membrane of an exemplary visualization and ablation catheter. The view includes expandable membrane 470, inner ablation electrode 472 and a portion of outer electrode 474, which are in electrical communication with individual conductive traces extending along a substrate, examples of which are described herein. CS illustrates the end point of the position vector from the camera to the point of interest.

The methods thus far take advantage of contact between a portion of the expandable member and at least a part of the patient (e.g., atrial wall). When the expandable member is in contact with the patient, the distance between the camera and the contacted part of the patient is estimated to be the same as the distance between the camera and the expandable member that is contacting that particular part of the patient. This is because the expandable member is directly adjacent and in contact with the particular part of the patient.

The distance between the camera and the expandable member may be known, or it may be estimated. In some methods the expandable member is filled with inflation fluid (which may be also irrigation fluid flowing through irrigation holes in the expandable member), and the shape of the expandable member stays generally the same when in use. When the shape can be estimated to stay generally the same, the distance between the camera and every location on the expandable member can be determined, assuming that there is a known expansion state or configuration of the expandable member. In some instances, the position of the distal end of the expandable member may be adjustable relative to the proximal end of the expandable member. In these embodiments, the distance between the camera and the expandable member can be determined based on the particular relative position between the distal and proximal ends of the balloon. Thus, when in use and moved into contact with tissue, the distance between the camera and the contacted tissue can always be estimated based on the known distance between the camera and the expandable member. The distance may vary slightly due to very slight changes in configuration, however.

One way in which to maintain the configuration of the expandable member when in use (e.g., when pressing up against atrial wall tissue), is to inflate the expandable membrane to or above a threshold internal fluid pressure, to ensure that the expandable member does not deform meaningful to prevent use of the known distances. For example, without limitation, in some embodiments if the internal fluid pressure is at least about 0.8 psi (e.g., at least about 1.0 psi), the configuration of the expandable member can stay the same, even when urged up against tissue.

In some embodiments herein the distal end of the expandable membrane is secured to distal end of an elongate device that may include a guidewire lumen therein. In some embodiments a hub is disposed at the distal end of the elongate device. The elongate device can be moved axially relative to distal end of the general catheter shaft, which can change the shape of the expandable member. The system can be configured so that some amount of travel in the elongate device (generally as a result of an actuator on the external handle) can be correlated to a change in shape in the expandable member. Alternatively, the system can be adapted such that a position of an external actuator on the handle can indicate the configuration or shape of the expandable member. Thus, the relative axial position of the elongate device can be correlated to a particular configuration of the expandable member. The relative axial position of the elongate device or handle component that controls it can be thus be used to determine the distance between the camera and the location on the expandable member.

Figure 46A:
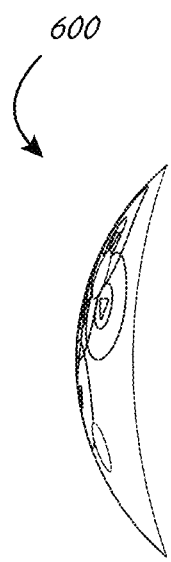
FIGS. 46A, 46B, 46C, and 46D illustrate exemplary patient maps in 3 space.
Figure 46B:
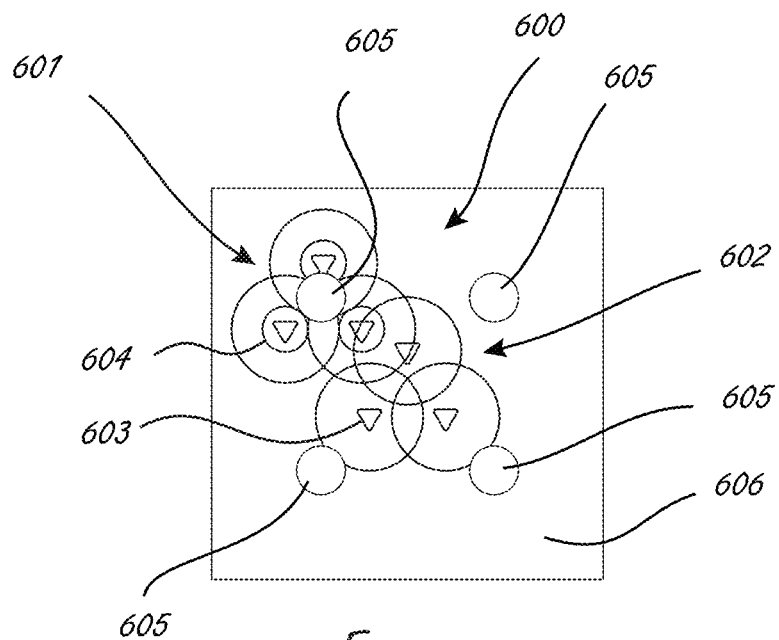
Figure 46C:
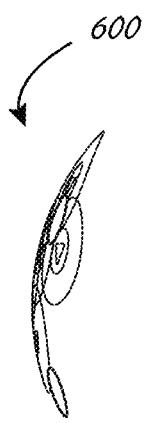
Figure 46D:
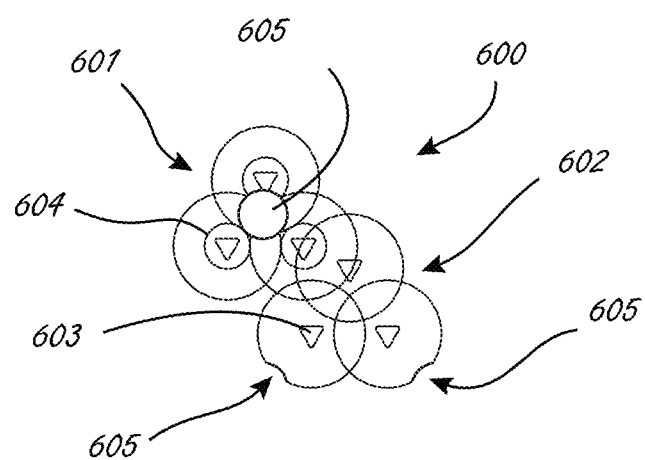

FIGS. 46A-46D illustrate exemplary patient maps 600 in 3 space created according to the methods herein, including combining a plurality of 2D images 601 and 602 (each of which comprises 3 images from 3 different cameras), captured by cameras, and tagged with information indicative of the location and orientation of a locational element. The methods used to create the patient maps in 3 space can utilize a known/estimated or a calculated distance from a camera. For example, the 3D models 600 shown in FIGS. 46A-46D can be created using the methods in FIGS. 44A-44E and the transformations between reference frames. FIGS. 46A and 46B illustrate two sets of camera images 601 and 602, each comprising three overlapping images from three different cameras, combined and shown relative to the anatomical landmarks in a left atrium when the images were captured. The triangles shown represent an overlap in camera images where a single electrode in each camera field of view overlap. The captured and combined images illustrate electrodes 603 (only one labeled for clarity), burned tissue region 604, and the fields of view from the cameras. The images frames are shown relative to anatomical landmarks including the pulmonary vein ostia 605, and the surface of the tissue 606 can also be seen generally. FIGS. 46A and 46B illustrate the combined images in 3 space, relative to the anatomical landmarks. FIGS. 46C and 46D illustrate the images combined into 3 space, wherein the anatomical references (in this embodiment the pulmonary veins) can be visualized as cutouts to the images. For example, the location of three pulmonary veins 605 can be seen in FIG. 46D, one of which is at the intersection of three images, while portions of two of them can visualized as cutouts in two of the fields of view.

FIGS. 46B and 46D illustrate a 2D projection of the patient map that was created in 3 space. The 2D representation can be displayed on a display or monitor, and be considered similar to FIG. 47D below.

The same procedure could be used to create a patient map of a larger portion of the surface of a left atrium.

The patient maps shown in FIGS. 46A-D can also be mapped onto images obtained of surfaces obtained from other imaging systems such as MRI or CT systems. For example, an MRI system can be used to create a 3D surface of a patient's left atrium, and a patient map herein can then be mapped onto the MRI 3D surface.

Figure 47A:
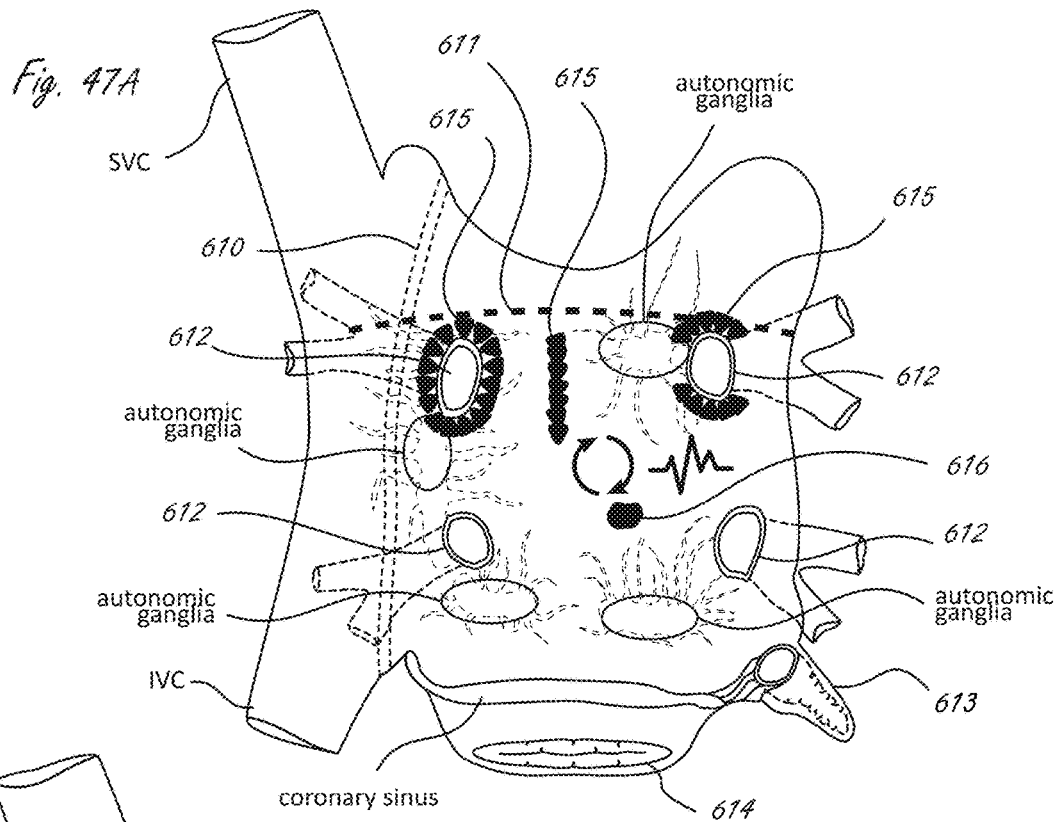
FIG. 47A illustrates exemplary landmarks that can be mapped into a patient map.

FIG. 47A illustrates an exemplary portion of a left atrium, identifying relative positions of anatomical landmarks (not all of which can actually be seen inside a left atrium) such as the phrenic nerve 610, Bachmann's bundle 611, four pulmonary veins 612, atrial appendage 613, and mitral valve 614. FIG. 45A also illustrates exemplary "created" landmarks that can optionally be mapped to any of the models herein, such burn landmarks 615, which illustrate where tissue has been ablated or otherwise modified by any suitable ablation catheter. For example, once tissue has been ablated according to any ablation process, the location of the ablated tissue can be mapped to the patient map, and thus presented visually to the physician. The software herein can thus identify for the physician what tissue has been ablated, and thus what tissue has not been ablated. The physician may then want to go back and ablate any of the non-ablated tissue. FIG. 47A also illustrates a created landmark 616 in the form of dye injected into heart tissue or applied to the surface of the tissue. In this manner a particular location within the tissue region can be marked, which can thus serve as an additional landmark in the modeling process. The landmark can even be an injury created during a procedure, such as an injury by a guide wire or other tool. The landmark can be a marking made intentionally on or to the tissue, but which does not harm the patient. The additional landmark can then be mapped into the model as if it were any other type of landmark. In some embodiments the hub of the expandable member includes an element that is adapted to deliver dye into the tissue, such as an actuatable needle in fluid communication with a dye reservoir, or port for needleless injection. When the device is positioned against tissue, the needle can be advanced into tissue, and dye can be injected through the needle and into the tissue, creating the landmark. Other anatomical features are also identified in FIG. 47A (e.g., superior and inferior vena cavas, coronary sinus, and autonomic ganglia).

Figure 47B:
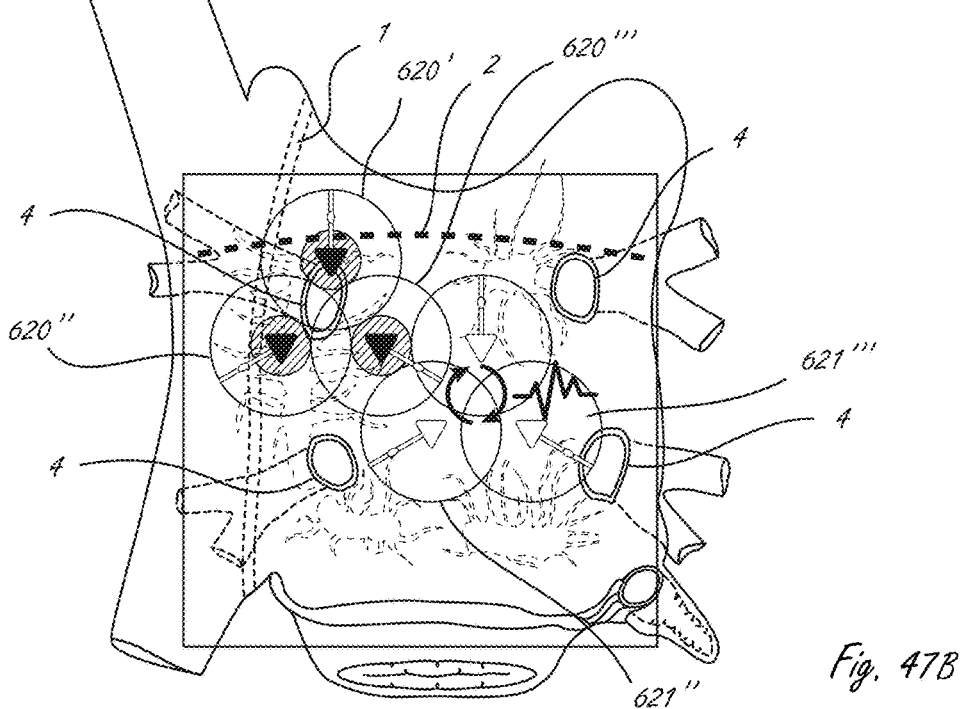
FIG. 47B represents fields of view from a plurality of camera relative to a left atrium and some exemplary landmarks.
Figures 47C, 47D:
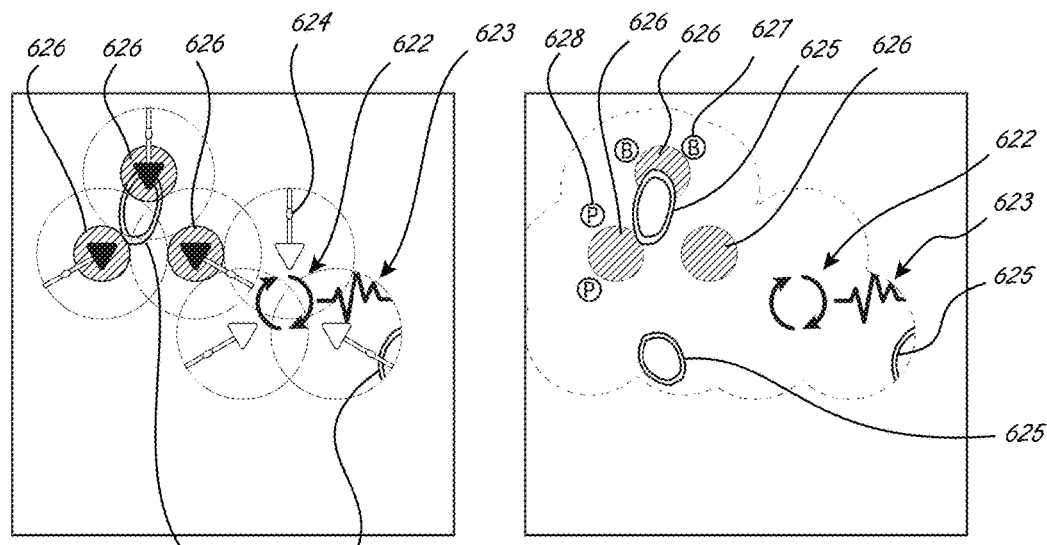
FIG. 47C illustrates an exemplary patient map that includes a plurality of captured and tagged images, and includes exemplary landmarks.
FIG. 47D illustrates an exemplary patient map that includes a plurality of captured and tagged images, and includes exemplary landmarks, while excluding some expandable member components from the field of view.

FIG. 47B illustrates two sets of images (620'-620''' and 621'-621''') obtained with a device having three cameras, wherein the sets of images were obtained when the device was in contact with the tissue. The two sets of images are combined using the methods herein. FIG. 47C shows the two sets of captured images combined, and includes the landmarks within the fields of view. FIG. 47C is an example of a patient map projected on a 2D plane and displayed. FIG. 47C also illustrates electrophysiological landmarks mapped onto the patient map, including rotor representation 622 and indicator of aberrant electrical activity 623, which can be sensed using any of the mapping electrodes 624 (only 1 labeled for clarity). Portions of ostia can also be seen.

FIG. 47D shows an exemplary displayed patient map as could be presented to a user, with a plurality of landmarks (and different types of landmarks) mapped to the patient map. Portions of three ostia 625 were in the fields of view. Burn landmarks 626 have been added to the patient map, which indicate locations of where tissue was ablated. Anatomical landmarks 627 (shown as "B" icons) are also included, which indicate the location of Bachmann's bundle, as well as landmarks 628 (shown as "P" icons), which indicate the location of the phrenic nerve.

Creating a patient map requires tagging at least two images for inclusion in the map. The images that will be tagged can be tagged automatically, or can be tagged based on user input. For example, the system can automatically tag all images in which contact has been made and use any of these (or all) of these images to create a map. The system can automatically capture images periodically or non-periodically. Alternatively, the system can be adapted to receive user input (e.g., pushing a button) to cause the tagging of the image to be used in creating the patient map. Any number of automatic or nonautomatic ways can be used to indicate what images should be used in the map creation.

The maps created herein may be displayed in real-time, or the maps can be stored for later visualization and analysis.

In some embodiments the method includes exciting tissue at a particular location using one or more electrodes on the expandable membrane, and then monitoring the response, and based on the response, the method could then map that location. As an example, the device can be positioned against tissue in order to attempt to excite Bachmann's bundle 611 (see FIG. 47A). When a contraction in the ventricle is detected, the location of Bachmann's bundle can be mapped to the model. Alternatively, an excitation could attempt to over excite Bachmann's bundle to inhibit or interfere with a contraction. When it is detected that the contraction has been inhibited or interfered with, the location can be mapped to the model. Alternatively, the device can be used to excite the phrenic nerve, and the method then includes monitoring for a diaphragm contraction. If the diaphragm contracts, the location of the phrenic nerve can be mapped to the model.

Figures 48A, 48B:
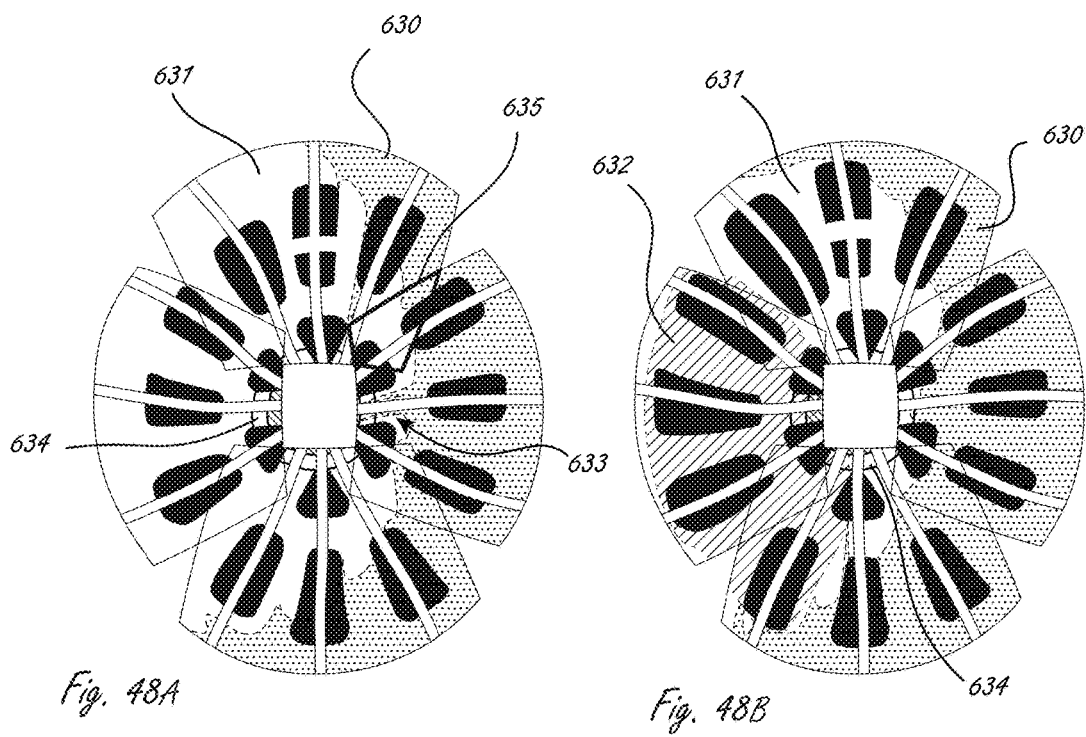
FIG. 48A illustrates visualization system images, with indicators to distinguish between the presence of blood and the lack of blood adjacent the expandable member.
FIG. 48B illustrates the view from 48A after an ablation procedure, with an additional indicator of a burned region of tissue.

FIGS. 48A and 48B illustrate an additional exemplary created landmark that can be mapped to any of the patient maps herein. In this example, computer implemented methods (e.g., algorithms) detect and indicates where contact has been made between the expandable member and tissue. Any type of indicator can then be mapped to the map to visually indicate where contact has been made. The methods can be adapted to detect the image color in the field of view in non-electrode and non-flex circuit regions. A white region indicates a lack of blood flow, and thus indicates that contact is being made against the tissue. A red color indicates blood flow, and thus a lack of contact between the device and the tissue. There can be degrees of red and white around any particular electrode, which may indicate partial contact between the device and tissue. The methods then map the region of contact (or the region of non-contact) to the patient map, which provides a visual indicator mapped on the patient map for the physician to understand where contact between the device and tissue has been made, and where contact between the device and tissue has not been made.

FIG. 48A illustrates images prior to tissue ablation, and FIG. 48B illustrates the captured images after an ablation. In this embodiment the device includes four cameras, the images from which have combined. The dotted area indicates where blood is present adjacent the expandable member (due to lack of sufficient contact between the balloon and the tissue, thus blood is present between the balloon and tissue). White region 631 indicates where the balloon is contacting the tissue, removing blood from the field of view, and appears white (or at least different than the red color indicating blood) in the image. Region 632 in FIG. 48B (shown as lined) indicates where tissue has been burned, or ablated, using the electrodes that are in contact with the tissue (as indicated by the lack of an indication of blood).

The location of region 632 can then be mapped onto a patient map, and displayed so the physician can understand that that tissue has been burned. FIG. 48A also illustrates another anatomical landmark 633, which as shown is a rivulet of blood (seen as the contrast between red and white in the images). This rivulet of blood is blood flowing from the pulmonary vein (into the left atrium) that is adjacent the device. The location of the ostium is shown generally at 634. The presence of the rivulet of blood can be used as an indicator of the location of the ostia, even if the ostia cannot be seen. The particular blood flow can thus provide an indication where a different anatomical landmark is location. The presence and orientation of blood flow 633 can thus be used as a way to map an ostia onto any of the patient maps herein, or simply as a helpful indicator to the physician of the location of an ostia. FIG. 48A also indicates an overlap region 635 wherein images from two different cameras are overlapped to present the larger combined image.

In some embodiments that utilize a locational element, the distance between the camera and the expandable member may not be known, and it may need to be calculated, or estimated. For example, if the expandable member does not maintain a substantially constant shape (e.g., fluid pressure within is not above a threshold), the distance may vary and a way of estimating the distance can enhance the accuracy of the created patient map. One concept utilizes a marker's known dimensions and the visualization system's ability to capture an image of the marker to determine a distance between the camera and a tissue region of interest. When the expandable membrane and associated marker are placed into contact with tissue, the distance between the contacted tissue and the camera is virtually the same as the distance between the marker and the camera. Determining the distance between the camera and marker thus provides the desired distance between the camera and the contacted tissue. The distance between the camera and marker (e.g., an electrode carried by the balloon, flex circuit component, etc.) can be determined by, after contacting tissue, quantifying the visualized dimensions, and comparing them to the known marker dimension relative to the field of view. If the marker's relative dimensions in the captured field of view stay the same, the marker would be at the known distance from the camera, and thus the tissue region would be at the known distance from the camera. If, for example, a particular dimension of the marker in pixels in the captured image were larger than its expected dimension in pixels, the marker (and tissue) or part of it would be closer to the camera than if the balloon were in the predetermined inflation state, likely due to the balloon being distorted inward by collapsing the balloon against the tissue. The dimensions of the marker in the captured image could also, for example, indicate if the marker was skewed due to engagement with a tissue surface that is not coplanar with the image plane. This could be an indicator a curvature in the tissue surface. The marker dimensions in the captured image can thus help determine the distance between the marker and camera, and the distance between the camera and the tissue region.

And once the distance between the camera and contacted tissue is determined, the known relationship between the camera field of view and the global frame of reference (characterized from the camera's fixed position and orientation relative to the locational element) can be used to place the tissue region into the global frame of reference. The process can be repeated for a plurality of tissue regions, and a patient map can then be created by combining the plurality of imaged tissue regions into the global frame of reference, using, for example, known mathematical relations implemented in software.

In embodiments in which the distance is not known and is being estimated, CS is an unknown position vector on the right side of the equation. GL can be sensed by the tracking system, and LC is fixed by the design of the catheter. CS can be estimated (via calculation) using the known dimensions of the marker. FIGS. 49A-49C illustrate an exemplary process using an exemplary marker to estimate CS. When the balloon surface in contact with the tissue surface is relatively flat and close to parallel to the image plane of the visualization system, the distance between the image plane of the visualization system and a marker within the field of view can be ascertained if the dimensions of the marker and the field of view of the visualizing system are known. In embodiments described herein, the marker can be any one or more of the following; the ablation element (e.g., electrode) or a feature of the ablation element or its supporting flex circuit, a portion of the guidewire shaft, a feature printed on or incorporated into the surface of the balloon or outer surface of the guidewire shaft, an element carried by the guidewire shaft, and an element carried by the camera housing.

For the case as described above the distance "d" to a scaling element on the surface of a balloon will be approximated by the following relation:

$$d(x_m, pix_{tot}, pix_{ref}, \alpha) := \frac{x_m \cdot \frac{pix_{tot}}{pix_{ref}}}{2 \tan\left(\frac{\alpha}{2}\right)} \quad (7)$$

Where $x_m$ is a known dimension of a visualization element, $pix_{tot}$ is the total number of pixels across the camera's image plane parallel to the known length feature on the image plane of the camera, $pix_{ref}$ is the number of pixels in the camera's image plane which span the known length feature on the image plane of the camera, and a is the angle comprised in the field of view. This applies where the pixels are evenly spaced and the horizontal and vertical pixel counts are equal.

The balloon is in contact with the point of interest, and thus the calculated distance between the camera and the marker can then be used as an estimation of the distance between the camera and the point, or CS. CS can then be used to characterize the position vector GS of the point, in the global frame of reference. This procedure can be repeated for as many points or surface regions as desired to create a patient map.

When combining image frames to create patient maps, some of the reference features (e.g., markers on the device or anatomical references (e.g., pulmonary vein ostia)) may not be scaled precisely due to, for example, differences in distance between the camera and the reference feature when the particular image is captured. For example, the distances between a camera and features can depend on how much contact is made between the expandable membrane and tissue. In some embodiments the patient mapping can thus include automatically scaling one or more reference features in the images to create a patient map in which reference features are to scale, or as close to scale as possible.

Systems herein can be adapted with a plurality of visualization modes. For example, the system can be adapted to generated maps in one or both of 2D planes and 3 spaces.

The user interface can allow the user (e.g., physician) to choose between the modes. Alternatively, the user interface can be adapted to display both 2D and 3D models simultaneously.

This disclosure also includes methods of combining (which may also be referred to as stitching) images together to create a composite image. In some embodiments the images can be captured as the visualization system is moved within and relative to the patient. The images can be stitched together by utilizing common features in the images. Any of the landmarks herein can be used as a common feature to combine the images together. For example, natural landmarks such as an ostium that show up in multiple images can be used to stitch a plurality of images together that visualize the ostium. Other landmarks such as created landmarks can be used as a feature common to a plurality of images to combine the images. Electrophysiological landmarks can similarly be used as a common feature to combine images. For example, the method can use timing relationships of monitored signals to help stitch images together. For example, referencing FIG. 31, the phase between signals can be used to help stitch the images together.

When combining, or stitching images together, the methods can be used with a locational element and global frame of reference as set above, but the methods need not include the use of a locational element. The use of a locational element may make it easier to create patient maps by having a known sensed position and orientation in a global frame, but it may not be absolutely necessary if landmarks can be used to effectively create a useable map. Thus, the disclosure also includes methods and systems that create maps of combined images that utilize any type of landmark, without the use of a locational element.

In many instances the surface to be mapped will be in motion during the mapping procedure. This is the case for instance when mapping the surface of the left atrium and the heart is beating. In such cases it is useful to capture a signal correlated with the motion, such as in this case an ECG, and temporally correlate the ECG with the data captured during the mapping process with the time at which it was acquired. One way to accomplish this correlation is to tag both sets of data with a timestamp and use the timestamp to accomplish the correlation.

What is claimed is:

1. A method of using a cardiac visualization catheter to create a patient map, the method comprising:
    positioning an ablation catheter within a patient adjacent tissue to be mapped, the ablation catheter comprising an expandable member that includes an expandable membrane,
        a camera disposed within the expandable membrane, the camera having a field of view, the camera orientated such that the camera field of view includes a portion of the expandable membrane when the expandable membrane is expanded, and
        a magnetic sensor with a fixed position and orientation relative to the camera, wherein the position and orientation of the magnetic sensor are defined in a global frame of reference and detectable by a magnetic sensor detector;
    delivering a fluid into the expandable membrane to at least partially inflate the expandable membrane;
    contacting the patient with at least a portion of the expandable membrane;
    capturing, with the camera, a plurality of different 2D images of the patient's anatomy adjacent the expandable member, each of which visualizes at least one part of the patient that is in contact with the expandable membrane;

tagging each of the plurality of different 2D images with information indicative of the position and orientation of the magnetic sensor when each of the plurality of different 2D images was captured;

creating a patient map, wherein creating the patient map comprises placing each of the plurality of different 2D images at a corresponding tagged position and orientation into a 3D space; and displaying the patient map.

2. The method of claim 1, wherein the ablation catheter includes a plurality of cameras disposed within the expandable membrane, each of the plurality of cameras having a different field of view, the magnetic sensor having a fixed position and orientation relative to each of the cameras, and wherein capturing a plurality of different 2D images with the camera comprises capturing a plurality of different 2D images with the plurality of cameras, and wherein the tagging step comprises tagging the plurality of different 2D images with information indicative of the position and orientation of the magnetic sensor when each of the plurality of 2D images was captured.

3. The method of claim 1 wherein creating the patient map comprises projecting the plurality of different 2D images onto a 2D plane, and wherein displaying the patient map comprises displaying the 2D plane.

4. The method of claim 1, wherein the patient map comprises a 2D patient map projected on a surface defined in a 3D volume where the surface is non planar.

5. The method of claim 1, further comprising mapping at least one natural landmark into the patient map.

6. The method of claim 5 wherein mapping at least one natural landmark into the patient map comprises mapping at least one pulmonary vein ostium into the patient map.

7. The method of claim 1, further comprising mapping at least one electrical landmark into the patient map.

8. The method of claim 7, wherein mapping at least one electrical landmark into the patient map comprises mapping at least one electrical landmark selected from the group consisting of: an electrophysiological landmark, a rotor, a nerve cell cluster, a nerve disposed on an inner wall of the heart, and a nerve extending adjacent the heart.

9. The method of claim 7, wherein mapping at least one electrical landmark into the patient map comprises sensing electrical activity of tissue in the heart, and mapping a location of aberrant electrical activity.

10. The method of claim 1, further comprising mapping at least one created landmark into the patient map.

11. The method of claim 10 wherein mapping at least one created landmark into the patient map comprises mapping a zone indicative of where the expandable membrane has made contact with tissue, or has not made contact with tissue.

12. The method of claim 11, further comprising distinguishing a color in the plurality of images that indicates that contact with tissue has been made from a color in the plurality of images that indicates that contact with tissue has not been made.

13. The method of claim 10, wherein mapping at least one created landmark into the patient map comprises mapping into the patient map a region of tissue into which ablation energy has been delivered.

14. The method of claim 10 further comprising injecting a dye into the tissue, and mapping the location of the dye into the patient map.

15. The method of claim 1, wherein the camera has a reference frame, the camera reference frame in a fixed position and orientation relative to the magnetic sensor, and wherein tagging each of the plurality of different images with information indicative of the position and orientation of the magnetic sensor when each of the plurality of images was captured comprises determining a position vector in the camera field of view in the global frame of reference.

16. The method of claim 15 wherein determining the position vector comprises using a known distance between the camera and a first scaling element carried by the expandable membrane.

17. The method of claim 15 wherein determining the position vector comprises estimating by calculating a distance between the camera and a point on the tissue.

18. The method of claim 17 wherein estimating by calculating a distance between the camera and a point on the tissue uses a change in a known dimension of a marker carried by the expandable member within the image.

19. The method of claim 1, wherein delivering fluid into the expandable membrane includes creating a fluid pressure within the membrane that is greater than a threshold, the created fluid pressure creating a substantially constant distance between the camera and the expandable member when the expandable member is pressed against atrial tissue.

20. The method of claim 19, wherein pressing the expandable member against atrial tissue causes the atrial tissue to deform around the expandable member due to the created fluid pressure.

* * * * *